(12) United States Patent
Jacobson et al.

(10) Patent No.: US 6,333,148 B1
(45) Date of Patent: Dec. 25, 2001

(54) GENES ENCODING SEVERAL POLY (ADP-RIBOSE) GLYCOHYDROLASE (PARG) ENZYMES, THE PROTEINS AND FRAGMENTS THEREOF, AND ANTIBODIES IMMUNOREACTIVE THEREWITH

(75) Inventors: Myron K. Jacobson; Elaine L. Jacobson, both of Lexington, KY (US); Jean-Christophe Amé, Obernai (FR); Winston Lin, Lexington, KY (US)

(73) Assignee: University of Kentucky Research, Lexington, KY (US)

( * ) Notice: Subject to any disclaimer, the term of this patent is extended or adjusted under 35 U.S.C. 154(b) by 0 days.

(21) Appl. No.: 09/302,812

(22) Filed: Apr. 30, 1999

Related U.S. Application Data

(60) Provisional application No. 60/083,768, filed on May 1, 1998.

(51) Int. Cl.[7] .............................. C12Q 1/68; C12Q 1/00; C12Q 1/34; C07K 14/00; C12N 9/22
(52) U.S. Cl. .................................. 435/4; 435/6; 435/18; 435/183; 435/199; 530/350
(58) Field of Search ............................. 435/4, 6, 7.1, 18, 435/183, 195, 199, 350; 530/827

(56) References Cited

U.S. PATENT DOCUMENTS 5,272,057  12/1993  Smulson et al. .
5,587,384  12/1996  Zhang et al. .

OTHER PUBLICATIONS

Slama et al. "Specific inhibition of poly(ADP–ribose) glycohydrolase by adenosine diphosphate (hydroxymethyl) pyrrolidinediol" J. Med. Chem. vol. 38, pp. 389–393, 1995.*

Uchida et al. "Preferential degradation of protein–bound (ADP–ribose)n by nuclear poly(ADP–ribose) glycohydrolase from human placenta" The Journal of Biological Chemistry, vol. 268, No. 5, pp. 3194–3200, Feb. 1993.*

Lin et al., "Isolation and Characterization of the cDNA Encoding Bovine Poly(ADP–ribose) Glycohydrolase" *Journal of Biological Chemistry*, 272:18:11895–11901 (1997).

* cited by examiner

Primary Examiner—John S. Brusca
Assistant Examiner—Karen A Lacourciere
(74) Attorney, Agent, or Firm—Fulbright & Jaworski, LLP

(57) ABSTRACT

The isolation and characterization of cDNAs encoding poly (ADP-ribose) glycohydrolase (PARG) enzymes and the amino acid sequences of PARGs from several species are described. PARG is involved in the cellular response to DNA damage and its proper function is associated with the body's response to neoplastic disorder inducing agents and oxidative stress. Expression vectors containing the cDNAs and cells transformed with the vectors are described. Probes and primers that hybridize with the cDNAs are described. Expression of the cDNA in *E. coli* results in an enzymatically active protein of about 111 kDa and an active fragment of about 59 kDa. Methods for inhibiting PARG expression or overexpressing PARG in a subject for therapeutic benefit are described. Exemplary of PARG inhibitors are anti-sense oligonucleotides. The invention has implications for treatment of neoplastic disorder, heart attack, stroke, and neurodegenerative diseases. Methods for detecting a mutant PARG allele are also described. Antibodies immunoreactive with PARGs and fragments thereof are described.

8 Claims, 21 Drawing Sheets

FIGURE 5

| | | | |
|---|---|---|---|
| bPARG | (422) | ED....KRKEQCEMKHQRTE..RKIPKYIPPH | SEQ ID NO: 19 |
| hPARG | (421) | ED....RRKEQWETKHQRTE..RKIPKYVPPH | SEQ ID NO: 20 |
| mPARG | (413) | ED....RRKEQCEVRHQRTE..RKIPKYIPPN | SEQ ID NO: 21 |
| CePARG | (29) | HQVPTMKRRKLTEHGNTTESLLLKEDPEEPKS | SEQ ID NO: 22 |
| hPARP | (205) | EG....KRKGD.EVDG.VDEVAKKKSKKEKDK | SEQ ID NO: 23 |
| mPARP | (205) | EG....KRKGD.EVDG.TDEVAKKKSRKETDK | SEQ ID NO: 24 |
| bPARP | (208) | EG....KRKGD.EVDG.IDEVTKKKSKKEKDK | SEQ ID NO: 25 |
| aPARP | (205) | EG....KRKGE.EVDG..NVVAKKKSRKEKEK | SEQ ID NO: 26 |
| XlPARP | (204) | EG....KRKAD.EVDG.HSAATKKKIKKEKEK | SEQ ID NO: 27 |
| DmPARP | (202) | EELPDTKRAKM.ELSDTNEEGEKKQR...... | SEQ ID NO: 28 |
| SpPARP | (205) | EGVSSAKKAKI.EKIDEEDAASIKELTEKIKK | SEQ ID NO: 29 |

FIGURE 16
Multiple Alignment of Amino Acid Sequences of PARG from Different Species

FIGURE 18
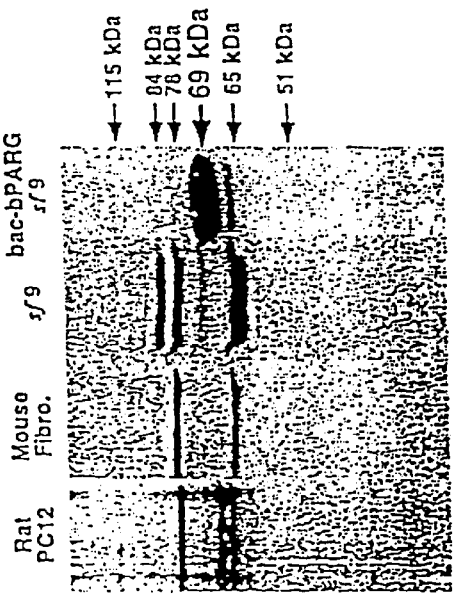
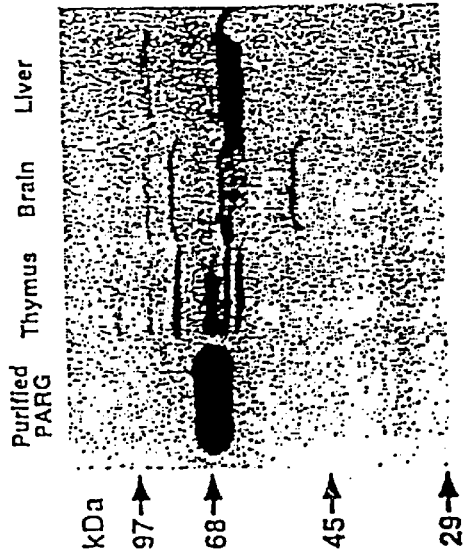

SEQUENCE LISTING

```
<160> NUMBER OF SEQ ID NOS: 38

<210> SEQ ID NO 1
<211> LENGTH: 4070
<212> TYPE: DNA
<213> ORGANISM: Bos taurus
<220> FEATURE:

<400> SEQUENCE: 1
accggaaagt gaacgaagcc cgaatcagaa cggctcatcc tgaggctggt agggtgccgg      60
tggaagaggg aaggcaggcg tctggatagg gcctggttcg ggaggctgtc agagcaggag     120
ctgcagaagc agtcagcggc agaggggca tggtgccggg aggcaccgag gaggggcgc      180
```

-continued

```
agtccgtccc tcccagggtt agtgaatgag gctctacgcc cgggctggcc cggagactca     240
gtgctgcggg tcccagcatg agtgcgggcc ccggctgtga gccctgcacc aagcgacccc     300
gctgggacgc cgctgcaact tctccgccgg ccgcctcgga cgcccggagc ttccccggca     360
ggcagaggcg cgtcctcgat tccaaggacg ctccggtgca gttcagggtc ccgccgtcct     420
cgtcaggctg cgccctgggc cgggcgggac agcaccgagg cagcgccacc tctcttgttt     480
tcaaacagaa gactataacc agttggatgg acactaaagg aatcaagaca gttgaatcag     540
aaagtttgca tagtaaagaa acaacaata caagagaaga atccatgatg agttctgtac      600
aaaaagataa cttttatcaa cataacatgg aaaaattaga aatgtttct cagctaggtt      660 ttgataagtc accagttgaa aaaggtacac agtatttgaa gcagcatcag actgcggcta     720
tgtgtaagtg gcagaatgaa gggccacact cagaacggct tttggaaagt gaacctccag     780
cggtaactct ggtaccagag cagttcagta atgctaatgt cgatcagtcg tccccaaagg     840
atgatcacag tgacacaaat agtgaggaga gtagagataa tcagcagttt ttgacacatg     900
taaagcttgc gaatgcaaag cagacgatgg aagatgaaca gggcagagaa gccagaagcc     960
accagaagtg tggcaaggct tgccatcctg cagaagcctg tgcagggtgt cagcaggagg    1020
agacagacgt ggtgtccgag agcccccttgt cggacactgg ctctgaggat gttggtactg    1080
gactgaaaaa tgccaacaga ttgaatagac aagaaagtag tctaggaaat tctcctccat    1140
ttgagaaaga aagtgaacct gagtcaccaa tggatgtaga taattccaaa aatagttgtc    1200
aggattcaga agcagatgaa gagacaagtc caggttttga tgaacaggaa gatagcagtt    1260
ctgctcaaac agcaaataaa ccttcaaggt tccaaccaag agaagctgac actgagttga    1320
ggaagcggtc ctctgctaag ggaggtgaga ttcgattaca tttccaattt gaaggaggag    1380
agagtcgagc tggaatgaat gatgtgaatg ccaaacgacc tggaagtact tctagcctga    1440
atgtagagtg cagaaattct aagcaacatg ggagaaagga ttctaaaatc acagatcatt    1500
tcatgagagt gcccaaagca gaggacaaaa gaaaagaaca atgtgaaatg aaacatcaaa    1560
gaacagaaag gaagatccct aaatacattc cacctcacct ttctccagat aagaaatggc    1620
ttggaactcc tattgaggag atgaggagaa tgccaaggtg tgggatccgg ctgcctccct    1680
tgagaccatc tgccaatcac acagtgacta ttcgggtaga tcttttgcga ataggagaag    1740
ttcctaaacc tttcccaaca cattttaaag atttgtggga caacaagcat gttaagatgc    1800
cttgttcaga acaaaacttg taccctgtgg aagatgagaa tggtgagcga gctgcaggca    1860
gccggtggga actcattcag actgcacttc tcaacaggct cactcggccc agaacctga    1920 aggatgctat tctgaagtac aatgtggcat attctaagaa atgggacttt acagctttga    1980
ttgatttctg ggataaggta ctagaagaag cagaagctca acacttgtat cagtccatct    2040
tgcctgatat ggtgaaaatt gcactctgtc tgccaaatat ttgtacccag ccaataccac    2100
tcctgaaaca gaagatgaat cattccatca caatgtcaca ggaacagatt gccagtcttt    2160
tagctaatgc tttcttctgc acgtttccac gacgcaatgc caagatgaaa tcagagtatt    2220
ccagttatcc agatattaac ttcaatcggt tgtttgaagg acgttcatca aggaaaccag    2280
agaagcttaa aacgctcttc tgctactttta gaagagtcac agagaaaaaa cccactgggt    2340
tggtgacatt cacaagacag agtcttgaag attttccaga gtgggaaaga tgtgaaaaac    2400
tcctgactcg actgcatgtc acttacgaag gtaccataga aggaaacggc cagggcatgc    2460
tacaggtgga ttttgcaaac cgtttcgttg gaggtggtgt aaccagtgca ggacttgtgc    2520
```

-continued

```
aagaagaaat ccgcttttta atcaaccctg agttgattgt ttcacggctc ttcactgagg    2580
tgctggatca caatgaatgt cttatcatca caggtactga gcagtacagt gaatacacag    2640
gctatgccga acataccgc tgggcccgga gccatgaaga caggagcgaa agggacgact    2700
ggcagaggcg cacgactgag atcgtcgcca tcgacgccct ccacttcaga cgctacctcg    2760
accagtttgt gcccgagaag atcagacggg agcttaacaa ggcttactgt ggatttcttc    2820
gtcctggagt tcttcagag aacctgtctg cagtggctac aggaaactgg ggctgtggtg    2880
cctttggggg tgatgctaga ctaaaagcct aatacagat cctggcagct gctgtagctg    2940
agcgagacgt ggtttatttc acctttgggg actcagaact gatgagagac atttacagca    3000
tgcatacatt cctcactgag aggaaactga ctgttggaga agtatataag ctgctgctac    3060
gatattacaa tgaagaatgc agaaactgct ccaccccgg accagacatc aagctttatc    3120
cattcatata ccatgcagtt gagtcctgta cacagaccac caaccagccg ggacaaagga    3180
cgggggcctg aggagccaag tgactagacg ctccccactt gtgtaacaag aaggtgtgac    3240
gtgtgaactg acatgatatc catgtgtata taatccgcgt ttgtaggcaa ggatgcagtc    3300
ccttccgccc atgcagctgt cagtacatct gcgcctcctc catcccgact tacatagact    3360
gagacatact ttgtttcttt tttttctat ttcagccctg attcttttat ttttctttct    3420
tttgcccatc agacttcttg tgaaatttca tcagagtttg tgctcagcct ggcaggtgtc    3480 tttttttgatg cctaaatata caaatcacct ctgcagctag cagatgccac ggaaggtggt    3540
ggaaccctag gagctgtaac tgagtctgct gcagatctcc ctctgagcct ctcacccta    3600 ccctattatc attgtggtgg tggaggtttt ttgattttg aaataagagt tgggtttgtt    3660
aaataataca gatctcctag gttaagagtt ttatatttaa gaatactttt caaaaagtta    3720
ttttgagata tcacctttat ttgtaatggt aatttgcctg tccctttcc cctgatcaat    3780 ttgtattgac tgtttttgga aattgaccca atgaaagga aatatgagaa taagagtttc    3840
ccaaatggtg tttaaaaaca aacaggttca agacacgcga aggacctcgt ttcctgggat    3900 ttttttttctt tttctttttt tgaattagga ttattgtttg ttccttggtg cttgagacat    3960
attcatataa ccaaagttta ggaactggga acttcgtggt gatttgtaca tattgaagtt    4020
tctctggtac tcaaaggtta tgtagttaat aaatttcat taacaaaaaa                4070
```

<210> SEQ ID NO 2
<211> LENGTH: 977
<212> TYPE: PRT
<213> ORGANISM: Bos taurus
<220> FEATURE:

<400> SEQUENCE: 2

```
Met Ser Ala Gly Pro Gly Cys Glu Pro Cys Thr Lys Arg Pro Arg Trp
1               5                   10                  15

Asp Ala Ala Ala Thr Ser Pro Pro Ala Ala Ser Asp Ala Arg Ser Phe
                20                  25                  30

Pro Gly Arg Gln Arg Arg Val Leu Asp Ser Lys Asp Ala Pro Val Gln
            35                  40                  45

Phe Arg Val Pro Pro Ser Ser Gly Cys Ala Leu Gly Arg Ala Gly
        50                  55                  60

Gln His Arg Gly Ser Ala Thr Ser Leu Val Phe Lys Gln Lys Thr Ile
65                  70                  75                  80

Thr Ser Trp Met Asp Thr Lys Gly Ile Lys Thr Val Glu Ser Glu Ser
                85                  90                  95
```

```
Leu His Ser Lys Glu Asn Asn Asn Thr Arg Glu Glu Ser Met Met Ser
            100                 105                 110

Ser Val Gln Lys Asp Asn Phe Tyr Gln His Asn Met Glu Lys Leu Glu
            115                 120                 125

Asn Val Ser Gln Leu Gly Phe Asp Lys Ser Pro Val Glu Lys Gly Thr
            130                 135                 140

Gln Tyr Leu Lys Gln His Gln Thr Ala Ala Met Cys Lys Trp Gln Asn
145                 150                 155                 160

Glu Gly Pro His Ser Glu Arg Leu Leu Glu Ser Glu Pro Pro Ala Val
                165                 170                 175

Thr Leu Val Pro Glu Gln Phe Ser Asn Ala Asn Val Asp Gln Ser Ser
            180                 185                 190

Pro Lys Asp Asp His Ser Asp Thr Asn Ser Glu Glu Ser Arg Asp Asn
            195                 200                 205

Gln Gln Phe Leu Thr His Val Lys Leu Ala Asn Ala Lys Gln Thr Met
            210                 215                 220

Glu Asp Glu Gln Gly Arg Glu Ala Arg Ser His Gln Lys Cys Gly Lys
225                 230                 235                 240

Ala Cys His Pro Ala Glu Ala Cys Ala Gly Cys Gln Gln Glu Glu Thr
                245                 250                 255

Asp Val Val Ser Glu Ser Pro Leu Ser Asp Thr Gly Ser Glu Asp Val
            260                 265                 270

Gly Thr Gly Leu Lys Asn Ala Asn Arg Leu Asn Arg Gln Glu Ser Ser
            275                 280                 285

Leu Gly Asn Ser Pro Pro Phe Glu Lys Glu Ser Glu Pro Glu Ser Pro
            290                 295                 300

Met Asp Val Asp Asn Ser Lys Asn Ser Cys Gln Asp Ser Glu Ala Asp
305                 310                 315                 320

Glu Glu Thr Ser Pro Gly Phe Asp Glu Gln Glu Asp Ser Ser Ser Ala
                325                 330                 335

Gln Thr Ala Asn Lys Pro Ser Arg Phe Gln Pro Arg Glu Ala Asp Thr
            340                 345                 350

Glu Leu Arg Lys Arg Ser Ser Ala Lys Gly Gly Glu Ile Arg Leu His
            355                 360                 365

Phe Gln Phe Glu Gly Gly Glu Ser Arg Ala Gly Met Asn Asp Val Asn
            370                 375                 380

Ala Lys Arg Pro Gly Ser Thr Ser Ser Leu Asn Val Glu Cys Arg Asn
385                 390                 395                 400

Ser Lys Gln His Gly Arg Lys Asp Ser Lys Ile Thr Asp His Phe Met
                405                 410                 415

Arg Val Pro Lys Ala Glu Asp Lys Arg Lys Glu Gln Cys Glu Met Lys
            420                 425                 430

His Gln Arg Thr Glu Arg Lys Ile Pro Lys Tyr Ile Pro Pro His Leu
            435                 440                 445

Ser Pro Asp Lys Lys Trp Leu Gly Thr Pro Ile Glu Glu Met Arg Arg
            450                 455                 460

Met Pro Arg Cys Gly Ile Arg Leu Pro Pro Leu Arg Pro Ser Ala Asn
465                 470                 475                 480

His Thr Val Thr Ile Arg Val Asp Leu Leu Arg Ile Gly Glu Val Pro
                485                 490                 495

Lys Pro Phe Pro Thr His Phe Lys Asp Leu Trp Asp Asn Lys His Val
            500                 505                 510

Lys Met Pro Cys Ser Glu Gln Asn Leu Tyr Pro Val Glu Asp Glu Asn
```

-continued

```
            515                 520                 525
Gly Glu Arg Ala Ala Gly Ser Arg Trp Glu Leu Ile Gln Thr Ala Leu
            530                 535                 540
Leu Asn Arg Leu Thr Arg Pro Gln Asn Leu Lys Asp Ala Ile Leu Lys
545                 550                 555                 560
Tyr Asn Val Ala Tyr Ser Lys Lys Trp Asp Phe Thr Ala Leu Ile Asp
                565                 570                 575
Phe Trp Asp Lys Val Leu Glu Glu Ala Glu Ala Gln His Leu Tyr Gln
                580                 585                 590
Ser Ile Leu Pro Asp Met Val Lys Ile Ala Leu Cys Leu Pro Asn Ile
            595                 600                 605
Cys Thr Gln Pro Ile Pro Leu Leu Lys Gln Lys Met Asn His Ser Ile
610                 615                 620
Thr Met Ser Gln Glu Gln Ile Ala Ser Leu Leu Ala Asn Ala Phe Phe
625                 630                 635                 640
Cys Thr Phe Pro Arg Arg Asn Ala Lys Met Lys Ser Glu Tyr Ser Ser
                645                 650                 655
Tyr Pro Asp Ile Asn Phe Asn Arg Leu Phe Glu Gly Arg Ser Ser Arg
                660                 665                 670
Lys Pro Glu Lys Leu Lys Thr Leu Phe Cys Tyr Phe Arg Arg Val Thr
            675                 680                 685
Glu Lys Lys Pro Thr Gly Leu Val Thr Phe Thr Arg Gln Ser Leu Glu
            690                 695                 700
Asp Phe Pro Glu Trp Glu Arg Cys Glu Lys Leu Leu Thr Arg Leu His
705                 710                 715                 720
Val Thr Tyr Glu Gly Thr Ile Glu Gly Asn Gly Gln Gly Met Leu Gln
                725                 730                 735
Val Asp Phe Ala Asn Arg Phe Val Gly Gly Val Thr Ser Ala Gly
                740                 745                 750
Leu Val Gln Glu Glu Ile Arg Phe Leu Ile Asn Pro Glu Leu Ile Val
            755                 760                 765
Ser Arg Leu Phe Thr Glu Val Leu Asp His Asn Glu Cys Leu Ile Ile
            770                 775                 780
Thr Gly Thr Glu Gln Tyr Ser Glu Tyr Thr Gly Tyr Ala Glu Thr Tyr
785                 790                 795                 800
Arg Trp Ala Arg Ser His Glu Asp Arg Ser Glu Arg Asp Asp Trp Gln
                805                 810                 815
Arg Arg Thr Thr Glu Ile Val Ala Ile Asp Ala Leu His Phe Arg Arg
            820                 825                 830
Tyr Leu Asp Gln Phe Val Pro Glu Lys Ile Arg Arg Glu Leu Asn Lys
            835                 840                 845
Ala Tyr Cys Gly Phe Leu Arg Pro Gly Val Ser Ser Glu Asn Leu Ser
850                 855                 860
Ala Val Ala Thr Gly Asn Trp Gly Cys Gly Ala Phe Gly Gly Asp Ala
865                 870                 875                 880
Arg Leu Lys Ala Leu Ile Gln Ile Leu Ala Ala Val Ala Glu Arg
                885                 890                 895
Asp Val Val Tyr Phe Thr Phe Gly Asp Ser Glu Leu Met Arg Asp Ile
                900                 905                 910
Tyr Ser Met His Thr Phe Leu Thr Glu Arg Lys Leu Thr Val Gly Glu
            915                 920                 925
Val Tyr Lys Leu Leu Leu Arg Tyr Tyr Asn Glu Glu Cys Arg Asn Cys
930                 935                 940
```

```
Ser Thr Pro Gly Pro Asp Ile Lys Leu Tyr Pro Phe Ile Tyr His Ala
945                 950                 955                 960

Val Glu Ser Cys Thr Gln Thr Thr Asn Gln Pro Gly Gln Arg Thr Gly
                965                 970                 975

Ala

<210> SEQ ID NO 3
<211> LENGTH: 4069
<212> TYPE: DNA
<213> ORGANISM: Homo sapiens
<220> FEATURE:

<400> SEQUENCE: 3
ggcgtctggg aagtgaggag cgtctctgcc tggcagaggc tgcaatctct gcactttggg      60
gggccaaggc aggcgctgag aaggacgcgc agtccatctc tctcaggtta gtgaaatgag     120
gctctccgcg gggccggccc ggggacagtg cgctgctggt cccagcatga atgcgggccc     180
cggctgtgaa ccctgcacca aagcgacccg ctggggcgcc gctacaactt cgccggctgc     240
ttcggacgcc cggagctttc cgagcaggca gaggcgcgtc ctcgacccca aggacgctca     300
cgtgcagttc agggtcccac cgtcctcgcc agcctgcgtc ccagggcagg cgggacagca     360
cagaggcagc gccacctcgc ttgttttcaa acaaaagact attaccagtt ggatggacac     420
taaaggaatc aagacagcgg aatcagaaag tttggatagt aaagaaaaca caatacaag      480 aatagaatcc atgatgagtt ctgtacaaaa agataacttt taccaacata atgtagaaaa     540
attagtaaat gtttctcagc taagtcttga taagtcactc actgaaaaaa gtacacagta     600
tttgaaccag catcagactg cagcaatgtg taagtggcaa aatgaaggga acacacgga      660 gcagcttttg gaaagtgaac ctcaaacagt aaccctggta ccagagcagt ttagtaatgc     720
taacattgat cggtcacctc aaaatgatga tcacagtgac acagatagtg aagagaatag     780
agacaatcaa cagtttctca aactgtaaa gcttgcaaat gcaaagcaga ctacggaaga     840
tgaacacgcc agagaagcca aaagccacca gaagtgcagc aagtcttgcc atcctgggga     900
agactgtgca agttgtcagc aagatgagat agacgtggtg ccaaagagtc cattgtcaga     960
tgttggctct gaggatgttg gtactgggtc aaaaaatgac aacaaattga ttagacaaga    1020
aagttgccta ggaaattctc ctccatttga aaggaaagt gaacccgaat caccgatgga    1080
tgtggataat tctaaaaata gttgtcaaga ctcagaagca gatgaggaga caagtccagg    1140
ttttgatgaa caagaagatg gtagttcctc ccaaacagca ataaaccctt caaggttcca    1200
agcaagagac gctgacattg aatttaggaa acggtactct actaagggcg gtgaagttag    1260
attacatttc caatttgaag gagagagag tcgcactgga atgaatgatt taaatgctaa    1320
actacctgga aatatttcta gcctgaatgt agaatgcaga aattctaagc aacatggaaa    1380
aaaggattct aaaatcacag atcatttgat gagactgccc aaagcagagg acagaagaaa    1440
agaacagtgg gaaaccaaac atcaaagaac agaaaggaag atccctaaat acgttccacc    1500
tcacctttct ccagataaga agtggcttgg aactcccatt gaggagatga aagaatgcc    1560 tcggtgtggg atccggctgc ctctcttgag accatctgcc aatcacacag taactattcg    1620
ggtagatctt ttgcgagcag gagaagttcc taaaccttt ccaacacatt ataaagattt    1680
gtgggataac aagcatgtta aaatgccttg ttcagaacaa atttgtacc agtggaaga    1740 tgagaatggt gagcgaactg cggggagccg gtgggagctc attcagactg cacttctcaa    1800 caatttaca cgaccccaaa acttgaagga tgctattctg aaatacaatg tggcatattc    1860
```

```
taagaaatgg gactttacag ctttgatcga tttctgggat aaggtacttg aagaagcaga    1920
agctcaacat ttatatcagt ccatcttgcc tgatatggtg aaaattgcac tctgtctgcc    1980
aaatatttgc acccagccaa taccactcct gaaacagaag atgaatcatt ccatcacaat    2040
gtcgcaggaa cagattgcca gtcttttagc taatgctttc ttctgcacat ttccacgacg    2100
aaatgctaag atgaaatcgg agtattctag ttacccagac attaacttca atcgattgtt    2160
tgagggacgt tcatcaagga aaccggagaa acttaaaacg ctcttctgct actttagaag    2220
agtcacagag aaaaaaccta ctgggttggt gacatttaca agacagagtc ttgaagattt    2280
tccagaatgg gaaagatgtg aaaaacccct gacacgattg catgtcactt acgaaggtac    2340
catagaagaa aatggccaag gcatgctaca ggtggatttt gcaaatcgtt ttgttggagg    2400
tggtgtaacc agtgcaggac ttgtgcaaga agaaatccgc ttttttaatca atcctgagtt    2460 gattatttca cggctcttca ctgaggtgct ggatcacaat gaatgtctaa ttatcacagg    2520
tactgagcag tacagtgaat acacaggcta tgctgagaca tatcgttggt cccggagcca    2580
cgaagatggg agtgaaaggg acgactgcga gcggcgctgc actgagatcg ttgccatcga    2640
tgctcttcac ttcagacgct acctcgatca gtttgtgcct gagaaaatga gacgcgagct    2700
gaacaaggct tactgtggat ttctccgtcc tggagtttct tcagagaatc tttctgcagt    2760
ggccacagga aactggggct gtggtgcctt tgggggtgat gccaggttaa aagccttaat    2820
acagatattg gcagctgctg cagctgagcg agatgtggtt tatttcacct ttggggactc    2880
agaattgatg agagacattt acagcatgca cattttcctt actgaaagga aactcactgt    2940
tggagatgtg tataagctgt tgctacgata ctacaatgaa gaatgcagaa actgttccac    3000
ccctggacca gacatcaagc tttatccatt catataccat gctgtcgagt cctgtgcaga    3060
gaccgctgac cattcagggc aaaggacagg gacctgagga gccgagcgaa tagcatctcc    3120
tcccacctcc caccagagac gtcctgtttg agctgtcagg tgtaatatat gaattgactt    3180
aagttaatat aaatgtgtac ataatccaca tttgtagtca aggacgcaat ctcttccaca    3240
catgtgcagt tgtcagttgg tacatctaaa ctccctccat cctgactcac gtggacttag    3300
atatgttttg tttctatttt cttctatttc agttttcat tctttgatgt ttatttcttt    3360
tgtccatcag atctcttgtg aaatcccatg gaaggttgtg ctcagctgtc gggtctcttt    3420
cttcctgccc atatattata ccagttgctt ctgcagcccg cagatgccca gcgatgccca    3480
ggaaacaagt tgaaatccca ggaatctctt taactgtattt tgctaaaaat ctccctgtga    3540
gccttccact caactcttaa tatgcttgca ttgtttaagt ttttaaattc tgaaaattaa    3600
taattagggt tttttttcata tgtgttgcat aatgcaaacc tcctaggtta aaatagtttc    3660
tttatttaag atagaataat ttccagaaat tgtacttttg aggtatcatt tttatctgta    3720
atggtttgtc tgtctttttt cctctgatca gtatttttt ataccagttt tggagactgc    3780
ctgagatgaa aggaaatgtg gaataaaagg aggttttcct gatgtggtgt aagaaaaca    3840 gattccaaga gaattgaaga tttttttgt tccttggta ctttttcttt tttaaattag    3900
gactaatgtt tcttttgtgg tgcttgaggc atattcatat aaccaaagtt tgagaactgg    3960
gaacttcatg ctgatttgta catattgaag tttctctggt attcaaggt tatatagtga    4020 atgaattttc attaataaat cactttgtca gaaaaaaaaa aaaaaaaa                4069
```

```
<210> SEQ ID NO 4
<211> LENGTH: 976
<212> TYPE: PRT
```

```
<213> ORGANISM: Homo sapiens
<220> FEATURE:

<400> SEQUENCE: 4

Met Asn Ala Gly Pro Gly Cys Glu Pro Cys Thr Lys Ala Thr Arg Trp
1               5                   10                  15

Gly Ala Ala Thr Thr Ser Pro Ala Ala Ser Asp Ala Arg Ser Phe Pro
                20                  25                  30

Ser Arg Gln Arg Arg Val Leu Asp Pro Lys Asp Ala His Val Gln Phe
            35                  40                  45

Arg Val Pro Pro Ser Ser Pro Ala Cys Val Pro Gly Gln Ala Gly Gln
        50                  55                  60

His Arg Gly Ser Ala Thr Ser Leu Val Phe Lys Gln Lys Thr Ile Thr
65                  70                  75                  80

Ser Trp Met Asp Thr Lys Gly Ile Lys Thr Ala Glu Ser Glu Ser Leu
                85                  90                  95

Asp Ser Lys Glu Asn Asn Thr Arg Ile Glu Ser Met Met Ser Ser
                100                 105                 110

Val Gln Lys Asp Asn Phe Tyr Gln His Asn Val Glu Lys Leu Val Asn
            115                 120                 125

Val Ser Gln Leu Ser Leu Asp Lys Ser Leu Thr Glu Lys Ser Thr Gln
130                 135                 140

Tyr Leu Asn Gln His Gln Thr Ala Ala Met Cys Lys Trp Gln Asn Glu
145                 150                 155                 160

Gly Lys His Thr Glu Gln Leu Leu Glu Ser Glu Pro Gln Thr Val Thr
                165                 170                 175

Leu Val Pro Glu Gln Phe Ser Asn Ala Asn Ile Asp Arg Ser Pro Gln
                180                 185                 190

Asn Asp Asp His Ser Asp Thr Asp Ser Glu Glu Asn Arg Asp Asn Gln
            195                 200                 205

Gln Phe Leu Thr Thr Val Lys Leu Ala Asn Ala Lys Gln Thr Thr Glu
        210                 215                 220

Asp Glu His Ala Arg Glu Ala Lys Ser His Gln Lys Cys Ser Lys Ser
225                 230                 235                 240

Cys His Pro Gly Glu Asp Cys Ala Ser Cys Gln Gln Asp Glu Ile Asp
                245                 250                 255

Val Val Pro Lys Ser Pro Leu Ser Asp Val Gly Ser Glu Asp Val Gly
                260                 265                 270

Thr Gly Ser Lys Asn Asp Asn Lys Leu Ile Arg Gln Glu Ser Cys Leu
            275                 280                 285

Gly Asn Ser Pro Pro Phe Glu Lys Glu Ser Glu Pro Glu Ser Pro Met
        290                 295                 300

Asp Val Asp Asn Ser Lys Asn Ser Cys Gln Asp Ser Glu Ala Asp Glu
305                 310                 315                 320

Glu Thr Ser Pro Gly Phe Asp Glu Gln Glu Asp Gly Ser Ser Ser Gln
                325                 330                 335

Thr Ala Asn Lys Pro Ser Arg Phe Gln Ala Arg Asp Ala Asp Ile Glu
                340                 345                 350

Phe Arg Lys Arg Tyr Ser Thr Lys Gly Gly Glu Val Arg Leu His Phe
            355                 360                 365

Gln Phe Glu Gly Gly Glu Ser Arg Thr Gly Met Asn Asp Leu Asn Ala
        370                 375                 380

Lys Leu Pro Gly Asn Ile Ser Ser Leu Asn Val Glu Cys Arg Asn Ser
385                 390                 395                 400
```

```
Lys Gln His Gly Lys Lys Asp Ser Lys Ile Thr Asp His Leu Met Arg
            405                 410                 415
Leu Pro Lys Ala Glu Asp Arg Arg Lys Glu Gln Trp Glu Thr Lys His
            420                 425                 430
Gln Arg Thr Glu Arg Lys Ile Pro Lys Tyr Val Pro Pro His Leu Ser
            435                 440                 445
Pro Asp Lys Lys Trp Leu Gly Thr Pro Ile Glu Glu Met Arg Arg Met
            450                 455                 460
Pro Arg Cys Gly Ile Arg Leu Pro Leu Leu Arg Pro Ser Ala Asn His
465                 470                 475                 480
Thr Val Thr Ile Arg Val Asp Leu Leu Arg Ala Gly Glu Val Pro Lys
            485                 490                 495
Pro Phe Pro Thr His Tyr Lys Asp Leu Trp Asp Asn Lys His Val Lys
            500                 505                 510
Met Pro Cys Ser Glu Gln Asn Leu Tyr Pro Val Glu Asp Glu Asn Gly
            515                 520                 525
Glu Arg Thr Ala Gly Ser Arg Trp Glu Leu Ile Gln Thr Ala Leu Leu
            530                 535                 540
Asn Lys Phe Thr Arg Pro Gln Asn Leu Lys Asp Ala Ile Leu Lys Tyr
545                 550                 555                 560
Asn Val Ala Tyr Ser Lys Lys Trp Asp Phe Thr Ala Leu Ile Asp Phe
            565                 570                 575
Trp Asp Lys Val Leu Glu Glu Ala Glu Ala Gln His Leu Tyr Gln Ser
            580                 585                 590
Ile Leu Pro Asp Met Val Lys Ile Ala Leu Cys Leu Pro Asn Ile Cys
            595                 600                 605
Thr Gln Pro Ile Pro Leu Leu Lys Gln Lys Met Asn His Ser Ile Thr
            610                 615                 620
Met Ser Gln Glu Gln Ile Ala Ser Leu Leu Ala Asn Ala Phe Phe Cys
625                 630                 635                 640
Thr Phe Pro Arg Arg Asn Ala Lys Met Lys Ser Glu Tyr Ser Ser Tyr
            645                 650                 655
Pro Asp Ile Asn Phe Asn Arg Leu Phe Glu Gly Arg Ser Ser Arg Lys
            660                 665                 670
Pro Glu Lys Leu Lys Thr Leu Phe Cys Tyr Phe Arg Arg Val Thr Glu
            675                 680                 685
Lys Lys Pro Thr Gly Leu Val Thr Phe Thr Arg Gln Ser Leu Glu Asp
            690                 695                 700
Phe Pro Glu Trp Glu Arg Cys Glu Lys Pro Leu Thr Arg Leu His Val
705                 710                 715                 720
Thr Tyr Glu Gly Thr Ile Glu Glu Asn Gly Gln Gly Met Leu Gln Val
            725                 730                 735
Asp Phe Ala Asn Arg Phe Val Gly Gly Val Thr Ser Ala Gly Leu
            740                 745                 750
Val Gln Glu Glu Ile Arg Phe Leu Ile Asn Pro Glu Leu Ile Ile Ser
            755                 760                 765
Arg Leu Phe Thr Glu Val Leu Asp His Asn Glu Cys Leu Ile Ile Thr
            770                 775                 780
Gly Thr Glu Gln Tyr Ser Glu Tyr Thr Gly Tyr Ala Glu Thr Tyr Arg
785                 790                 795                 800
Trp Ser Arg Ser His Glu Asp Gly Ser Glu Arg Asp Asp Cys Glu Arg
            805                 810                 815
```

-continued

```
Arg Cys Thr Glu Ile Val Ala Ile Asp Ala Leu His Phe Arg Arg Tyr
            820                 825                 830

Leu Asp Gln Phe Val Pro Glu Lys Met Arg Arg Glu Leu Asn Lys Ala
        835                 840                 845

Tyr Cys Gly Phe Leu Arg Pro Gly Val Ser Ser Glu Asn Leu Ser Ala
    850                 855                 860

Val Ala Thr Gly Asn Trp Gly Cys Gly Ala Phe Gly Gly Asp Ala Arg
865                 870                 875                 880

Leu Lys Ala Leu Ile Gln Ile Leu Ala Ala Ala Ala Glu Arg Asp
                885                 890                 895

Val Val Tyr Phe Thr Phe Gly Asp Ser Glu Leu Met Arg Asp Ile Tyr
            900                 905                 910

Ser Met His Ile Phe Leu Thr Glu Arg Lys Leu Thr Val Gly Asp Val
        915                 920                 925

Tyr Lys Leu Leu Leu Arg Tyr Tyr Asn Glu Glu Cys Arg Asn Cys Ser
    930                 935                 940

Thr Pro Gly Pro Asp Ile Lys Leu Tyr Pro Phe Ile Tyr His Ala Val
945                 950                 955                 960

Glu Ser Cys Ala Glu Thr Ala Asp His Ser Gly Gln Arg Thr Gly Thr
                965                 970                 975
```

<210> SEQ ID NO 5
<211> LENGTH: 3814
<212> TYPE: DNA
<213> ORGANISM: Mus musculus
<220> FEATURE:

<400> SEQUENCE: 5

```
gggggactgt gtgctgcggg tcccagcatg agtgcgggcc ccggctggga gccctgcacg      60
aaagcgcgct ggggcgccgc tggaacttct gcgccgactg cctcggactc ccggagcttc     120
cctggcaggc agaggcgtgt tctcgacccc aaggacgctc ccgtccagtt cagggtccct     180
ccgtcctcgc cagcctgcgt ctcggggcgg gcgggaccgc acagaggcaa cgccacctcg     240
tttgttttca acaaaagac tattactact tggatggata ctaaaggacc caagacagct     300
gaatcagaaa gtaaagaaaa caacaataca agaattgact ccatgatgag ttctgtgcag     360
aaagataact tttacccaca taaggtggaa aaattggaaa atgttcctca gctaaatctt     420
gataaatcac ccacagaaaa gagttcacag tatttgaacc aacagcagac tgcgagtgtg     480
tgcaagtggc agaatgaagg gaagcatgca gaacagcttt tggcaagtga gcctcccgcg     540
gggactccgc taccaaagca gcttagtaat gctaacattg gtcagtcacc ccacactgat     600
gaccacagtg acacagatca tgaagaagac agagacaatc agcagtttct tacacctata     660
aaacttgcaa atacaaagcc aacagtagga gatgggcagg ccagaagcaa ctgtaagtgc     720
agtggatctc gccagtctgt gaaagactgt acaggctgtc aacaggagga ggtggatgtg     780
ctaccagaga gtcctttgtc agatgttggt gccgaggaca ttggaactgg accaaaaaat     840
gacaacaaat tgactggaca agaaagcagc ctaggtgatt cgcctccatt tgagaaagaa     900
agtgagcctg agtcaccaat ggatgtagac aactcgagaa acagttgtca agattcagaa     960
gcagatgaag aaacaagtcc agtctttgat gagcaagatg atcgttcctc ccaaacagca    1020
aataaacttt caagttgcca agcaagagaa gctgatggcg atcttaggaa acggtatttg    1080
actaagggaa gtgaagttag attgcatttc caatttgaag agaaaataa tgctgggacc    1140
agtgacttaa atgccaagcc atctggaaac tcttctagcc ttaatgtaga gtgtagaagt    1200
```

-continued

```
tccaagcagc atggaaaaag ggattctaaa attacagatc atttcatgag aatttccaag      1260
tcagaggaca gaagaaaaga acaatgtgaa gtcagacatc aaagaacaga aaggaagatt      1320
ccaaaataca tcccacctaa cctccctcca gagaagaagt ggctgggaac tcctattgag      1380
gaaatgagaa aaatgcctcg gtgtgggatc catttgcctt ccttaagacc atctgcaagt      1440
cacacagtga ctgttcgggt agaccttctg agagcaggag aggttccgaa acctttcca      1500 acacattaca aagatttgtg ggataacaaa catgtgaaaa tgccttgttc ggaacaaaac      1560
ttgtaccctg tggaagatga aatggtgag cgaactgcag ggagtaggtg ggagctcatt      1620
cagactgcac ttctcaacaa attcacacga ccccagaact tgaaggatgc gattctgaaa      1680
tacaatgtgg catattctaa gaatgggac tttacagctt tggttgattt ctgggataag      1740
gtacttgaag aagcagaggc ccaacattta tatcagtcca ttttacctga catggtgaaa      1800
attgcactct gtctgccaaa tatttgcacc cagccaatac cactcctgaa acagaagatg      1860
aatcattctg tcacgatgtc acaggaacag atcgccagtc ttttagctaa tgctttcttc      1920
tgcacatttc cccgacggaa tgccaagatg aaatcggagt attctagtta cccagacatt      1980
aacttcaatc ggttgtttga aggacgttca tcaaggaaac cagaaaaact gaaaacactc      2040
ttctgctact ttcgaagagt cacagagaaa aaacctacag gattggtgac atttacaaga      2100
cagagtcttg aagattttcc agaatgggaa aggtgtgaaa agcctctgac acgcttacac      2160
gtcacttacg agggtaccat agaaggcaac ggccgaggca tgctacaggt ggattttgca      2220
aatcgttttg ttgaggtgg tgtgactggt gcgggacttg tacaagaaga aatcagattt      2280
ttaatcaatc ctgaattgat tgtttcacgg ctgttcactg aggtgctgga tcacaatgag      2340
tgtcttatta tcacaggtac tgaacagtac agtgaataca caggctatgc tgaaacttat      2400
cgttgggccc gaagccatga agatgggagt gaaaaggacg attggcagcg gcgctgcacg      2460
gagatcgttc ccattgacgc acttcacttc agacgctacc tcgatcagtt tgtgcctgag      2520
aaagtgagac gtgagcttaa caaggcttac tgcggattcc tccgtcctgg agttccttct      2580
gaaaatcttt ctgcagtggc cacgggaaac tggggctgtg tgcctttgg gggtgacgct      2640 agattaaaag ccttaataca gatcctggca gctgctgcgg ctgaacgtga cgtggtttat      2700
ttcacctttg gggactcaga gttgatgaga gacatttaca gcatgcacac tttccttacc      2760
gagaggaagc tggatgttgg aaaagtgtac aagttattgc ttagatacta caatgaagaa      2820
tgcagaaact gttccacccc tggaccagac atcaagcttt atccattcat ataccatgct      2880
gttgagtcaa gtgcagagac cactgacatg ccaggacaga aggcaggcac ctgaggaaca      2940
agtgactagg acctcctctc aaagagacat cctatttgaa atgtggggtg tgatgtctga      3000
attgactgaa tctgatctaa gtgtgtatat aatccacatt tgtaatcaag gatgcagtct      3060
cttctgcata tgcagttgtt tcttgttcat cctggtggac atgcctttag acatggcttc      3120
ttcaattttt cttctccttc agtctttatt ctttgatttt tttttccaa cttgatttct      3180 tgggaaaact caagaaaggt tgcactcagc ttctagatct ttctcttcct gtctgtgtgt      3240
tgtccagact gctttggtgg ctagcagata ccatcacact tggaggaagt tacaaatcca      3300
gaaatctgag tttgctgcag atttacctgt gagcttctca ctcccaaccc ttgttaggct      3360
tgtgttgtct acatttcaa ttttggaagt tgaagttttt cttatgttac ttaatgctag      3420
tatcttttag gctaaaacta ttttctattt aaggcagact aatttccagt ttctcttttg      3480
aaacatcatc cctataagta acggtttttt tcgtcctttt ttccccagcg ctattttaga      3540
agctggccaa gaggaaagaa aatgtagaat aaaaggattt tcctcggatg ctataaagaa      3600
```

```
gccaggttca agagcgttgg ggttttttgtt tttttcaaga cttgtttttc ctttgcagct    3660
agggtgagtg cttgttctgt ggtgctgagg gcatagtcct gtaaccaaag gtctttgctg    3720
gagacttgat gctgatttgt acatatggaa gtttctctgg caggaaatat tagagttaat    3780
aaatttcatt aataaatcat ttgtcagaaa aaaa                                3814
```

<210> SEQ ID NO 6
<211> LENGTH: 968
<212> TYPE: PRT
<213> ORGANISM: Mus musculus
<220> FEATURE:

<400> SEQUENCE: 6

```
Met Ser Ala Gly Pro Gly Trp Glu Pro Cys Thr Lys Ala Arg Trp Gly
1               5                   10                  15

Ala Ala Gly Thr Ser Ala Pro Thr Ala Ser Asp Ser Arg Ser Phe Pro
            20                  25                  30

Gly Arg Gln Arg Arg Val Leu Asp Pro Lys Asp Ala Pro Val Gln Phe
        35                  40                  45

Arg Val Pro Pro Ser Ser Pro Ala Cys Val Ser Gly Arg Ala Gly Pro
    50                  55                  60

His Arg Gly Asn Ala Thr Ser Phe Val Phe Lys Gln Lys Thr Ile Thr
65                  70                  75                  80

Thr Trp Met Asp Thr Lys Gly Pro Lys Thr Ala Glu Ser Glu Ser Lys
                85                  90                  95

Glu Asn Asn Asn Thr Arg Ile Asp Ser Met Met Ser Ser Val Gln Lys
            100                 105                 110

Asp Asn Phe Tyr Pro His Lys Val Glu Lys Leu Glu Asn Val Pro Gln
        115                 120                 125

Leu Asn Leu Asp Lys Ser Pro Thr Glu Lys Ser Ser Gln Tyr Leu Asn
    130                 135                 140

Gln Gln Gln Thr Ala Ser Val Cys Lys Trp Gln Asn Glu Gly Lys His
145                 150                 155                 160

Ala Glu Gln Leu Leu Ala Ser Glu Pro Pro Ala Gly Thr Pro Leu Pro
                165                 170                 175

Lys Gln Leu Ser Asn Ala Asn Ile Gly Gln Ser Pro His Thr Asp Asp
            180                 185                 190

His Ser Asp Thr Asp His Glu Glu Asp Arg Asp Asn Gln Gln Phe Leu
        195                 200                 205

Thr Pro Ile Lys Leu Ala Asn Thr Lys Pro Thr Val Gly Asp Gly Gln
    210                 215                 220

Ala Arg Ser Asn Cys Lys Cys Ser Gly Ser Arg Gln Ser Val Lys Asp
225                 230                 235                 240

Cys Thr Gly Cys Gln Gln Glu Glu Val Asp Val Leu Pro Glu Ser Pro
                245                 250                 255

Leu Ser Asp Val Gly Ala Glu Asp Ile Gly Thr Gly Pro Lys Asn Asp
            260                 265                 270

Asn Lys Leu Thr Gly Gln Glu Ser Ser Leu Gly Asp Ser Pro Pro Phe
        275                 280                 285

Glu Lys Glu Ser Glu Pro Glu Ser Pro Met Asp Val Asp Asn Ser Arg
    290                 295                 300

Asn Ser Cys Gln Asp Ser Glu Ala Asp Glu Glu Thr Ser Pro Val Phe
305                 310                 315                 320

Asp Glu Gln Asp Asp Arg Ser Ser Gln Thr Ala Asn Lys Leu Ser Ser
```

-continued

```
                    325                 330                 335
    Cys Gln Ala Arg Glu Ala Asp Gly Asp Leu Arg Lys Arg Tyr Leu Thr
                340                 345                 350
    Lys Gly Ser Glu Val Arg Leu His Phe Gln Phe Glu Gly Glu Asn Asn
                355                 360                 365
    Ala Gly Thr Ser Asp Leu Asn Ala Lys Pro Ser Gly Asn Ser Ser Ser
                370                 375                 380
    Leu Asn Val Glu Cys Arg Ser Ser Lys Gln His Gly Lys Arg Asp Ser
385                 390                 395                 400
    Lys Ile Thr Asp His Phe Met Arg Ile Ser Lys Ser Glu Asp Arg Arg
                    405                 410                 415
    Lys Glu Gln Cys Glu Val Arg His Gln Arg Thr Glu Arg Lys Ile Pro
                420                 425                 430
    Lys Tyr Ile Pro Pro Asn Leu Pro Pro Glu Lys Lys Trp Leu Gly Thr
                435                 440                 445
    Pro Ile Glu Glu Met Arg Lys Met Pro Arg Cys Gly Ile His Leu Pro
                450                 455                 460
    Ser Leu Arg Pro Ser Ala Ser His Thr Val Thr Val Arg Val Asp Leu
465                 470                 475                 480
    Leu Arg Ala Gly Glu Val Pro Lys Pro Phe Pro Thr His Tyr Lys Asp
                    485                 490                 495
    Leu Trp Asp Asn Lys His Val Lys Met Pro Cys Ser Glu Gln Asn Leu
                500                 505                 510
    Tyr Pro Val Glu Asp Glu Asn Gly Glu Arg Thr Ala Gly Ser Arg Trp
                515                 520                 525
    Glu Leu Ile Gln Thr Ala Leu Leu Asn Lys Phe Thr Arg Pro Gln Asn
                530                 535                 540
    Leu Lys Asp Ala Ile Leu Lys Tyr Asn Val Ala Tyr Ser Lys Lys Trp
545                 550                 555                 560
    Asp Phe Thr Ala Leu Val Asp Phe Trp Asp Lys Val Leu Glu Glu Ala
                    565                 570                 575
    Glu Ala Gln His Leu Tyr Gln Ser Ile Leu Pro Asp Met Val Lys Ile
                580                 585                 590
    Ala Leu Cys Leu Pro Asn Ile Cys Thr Gln Pro Ile Pro Leu Leu Lys
                595                 600                 605
    Gln Lys Met Asn His Ser Val Thr Met Ser Gln Glu Gln Ile Ala Ser
                610                 615                 620
    Leu Leu Ala Asn Ala Phe Phe Cys Thr Phe Pro Arg Arg Asn Ala Lys
625                 630                 635                 640
    Met Lys Ser Glu Tyr Ser Ser Tyr Pro Asp Ile Asn Phe Asn Arg Leu
                    645                 650                 655
    Phe Glu Gly Arg Ser Ser Arg Lys Pro Glu Lys Leu Lys Thr Leu Phe
                660                 665                 670
    Cys Tyr Phe Arg Arg Val Thr Glu Lys Lys Pro Thr Gly Leu Val Thr
                675                 680                 685
    Phe Thr Arg Gln Ser Leu Glu Asp Phe Pro Glu Trp Glu Arg Cys Glu
                690                 695                 700
    Lys Pro Leu Thr Arg Leu His Val Thr Tyr Glu Gly Thr Ile Glu Gly
705                 710                 715                 720
    Asn Gly Arg Gly Met Leu Gln Val Asp Phe Ala Asn Arg Phe Val Gly
                    725                 730                 735
    Gly Gly Val Thr Gly Ala Gly Leu Val Gln Glu Glu Ile Arg Phe Leu
                740                 745                 750
```

Ile Asn Pro Glu Leu Ile Val Ser Arg Leu Phe Thr Glu Val Leu Asp
        755                 760                 765

His Asn Glu Cys Leu Ile Ile Thr Gly Thr Glu Gln Tyr Ser Glu Tyr
        770                 775                 780

Thr Gly Tyr Ala Glu Thr Tyr Arg Trp Ala Arg Ser His Glu Asp Gly
785                 790                 795                 800

Ser Glu Lys Asp Asp Trp Gln Arg Arg Cys Thr Glu Ile Val Ala Ile
            805                 810                 815

Asp Ala Leu His Phe Arg Arg Tyr Leu Asp Gln Phe Val Pro Glu Lys
            820                 825                 830

Val Arg Arg Glu Leu Asn Lys Ala Tyr Cys Gly Phe Leu Arg Pro Gly
            835                 840                 845

Val Pro Ser Glu Asn Leu Ser Ala Val Ala Thr Gly Asn Trp Gly Cys
        850                 855                 860

Gly Ala Phe Gly Gly Asp Ala Arg Leu Lys Ala Leu Ile Gln Ile Leu
865                 870                 875                 880

Ala Ala Ala Ala Ala Glu Arg Asp Val Val Tyr Phe Thr Phe Gly Asp
                885                 890                 895

Ser Glu Leu Met Arg Asp Ile Tyr Ser Met His Thr Phe Leu Thr Glu
        900                 905                 910

Arg Lys Leu Asp Val Gly Lys Val Tyr Lys Leu Leu Arg Tyr Tyr
        915                 920                 925

Asn Glu Glu Cys Arg Asn Cys Ser Thr Pro Gly Pro Asp Ile Lys Leu
        930                 935                 940

Tyr Pro Phe Ile Tyr His Ala Val Glu Ser Ser Ala Glu Thr Thr Asp
945                 950                 955                 960

Met Pro Gly Gln Lys Ala Gly Thr
                965

<210> SEQ ID NO 7
<211> LENGTH: 2781
<212> TYPE: DNA
<213> ORGANISM: Drosophila melanogaster
<220> FEATURE:

<400> SEQUENCE: 7
tcgaagtgtg tggtatttat aaagtgcgat attcatcaca gctatcgctc atcccaaaa     60 caccggtatg caagaattca ggtcacactt gattttccg atattccaaa aggtttacca    120
atctacggca atcgccgca gagcaagtgc atccgtgctg accaatcgac tcggcaaggc    180
tttgtgctta aactgcgcca ggatgtcgaa gtcgccggat ggcgggattt ccgaaataga    240
aacggaggag gagccggaaa atctggcgaa ctccctagat gattcgtggc gtggagtttc    300
catggaggct atacatcgta atcggcagcc tttcgaattg agaatttgc caccagtgac    360 tgccggcaat ctccaccggg ttatgtacca gctgccaatt cgtgaaacac cgccacgccc    420
ctacaaatca ccgggaaagt gggactccga gcatgtgcgt ctgccctgtg cgcccgagtc    480
gaaatatccg agggagaatc cggatggcag caccaccatc gattttcgct gggaaatgat    540
cgaacgagcc cttctgcagc ccataaagac gtgtgaggaa ctgcaggcgg cgataatatc    600
atataatacc acctataggg atcagtggca ctttcgtgcc cttcatcaac ttctcgacga    660
ggaactggac gagagcgaaa cacgggtttt cttcgaggat ctattgccgc gcattatccg    720
attggcattg cggctaccgg acttgattca atcgccagtt ccgctgctca agcaccacaa    780
gaacgcctca ttgagcctga gccaacagca gatctcctgc ctgttggcca atgccttctt    840

```
gtgcacgttt ccccgaagaa acaccctcaa gaggaagtcc gagtacagca cttttccaga    900
catcaacttt aacaggcttt accaatcgac gggaccggca gttctggaga agcttaaatg    960
cattatgcac tattttcgtc gcgtgtgtcc cacagagcgg gatgccagca atgtgcccac   1020
cggtgtggta acctttgttc gtcggagcgg attgccggaa catctgatcg actggagcca   1080
aagtgcggcg ccgttgggtg atgtgccatt gcacgtggat gccagggaa caatcgagga    1140 tgagggcatt ggactgctgc aagtagactt tgccaacaaa tatttgggtg cggtgtctt    1200 gggacatggc tgcgttcagg aggagatacg ctttgttatc tgtccggagc tattggtggg   1260
taaactcttt acggagtgtc tgcgaccatt cgaggccctg gtgatgttgg gcgccgaaag   1320
gtatagtaac tatacgggat atgccggaag cttcgagtgg tccggcaact ttgaggattc   1380
aacgccaaga gatagctcag gtcgtcgaca acggccatt gtggcaatcg atgccctaca    1440
ttttgcccag tcacatcatc aatatcgcga ggatctcatg gaaagggagc tgaacaaggc   1500
gtacattgga tttgttcact ggatggtgac gccgccaccg ggtgtggcaa ctggtaactg   1560
gggttgcggc gcattcggcg gtgactccta tctgaaagcc ctgctgcaac ttatggtctg   1620
cgcccagttg ggcagacctt tggcctacta acctttgga aatgtggagt ttagggatga    1680
ttttcatgaa atgtggctgt tgtttcgaaa tgacgggact acggtgcagc agctttggag   1740
tattttaagg tcgtacagta ggcttattaa ggagaagagc tccaaggagc gcgtgagaa    1800 taaggcatcc aaaaagaagc tatatgattt tattaaagag gaacttaaga aggtcagaga   1860
tgtgcccgga gagggagcat ccgccgaagc tggaagctct agagtagctg gattaggcga   1920
aggaaaatca gaaacatcag cgaaatcctc gccagaactc aacaagcaac ccgcccgacc   1980
gcaaatcacc ataacgcaac aaagtaccga tctattgccc gcgcaattat cgcaagataa   2040
ctctaattct tcggaagatc aggcccttct tatgctgtcg gacgatgagg aggccaatgc   2100
catgatggag gccgctagtc tggaggctaa aagcagcgta gaaataagca acagcagcac   2160
aacgtccaaa acgagcagta cagccacgaa atcaatgggt tcaggtggcc gccagttgag   2220
tctgctcgag atgctggaca cccattatga aaagggttcg gcctcgaaga ggccacgaaa   2280
atcacccaac tgcagcaagg ctgagggttc agcaaagagt cgtaaggaga tcgatgtgac   2340
cgacaaggac gaaaaggacg atattgttga ctaggtgata ttgcactaca ggattgttac   2400 tgccccaaa aattgaagag gtataaaatg tattgtagat aactttaagg acatatttag    2460
ggcattttaa agtaggatca ttgtaagtcg aataaagtga atttttttt ttttttaat     2520 tatactattc taatctgcaa agacaatttt actgttaaat ttgtataaca ttcgaattaa   2580
ttaatataat ttgttatatc atgcaaatct agctttatt atgcgaaatt tgtagttaaa    2640
gccagtaaag tttctttta tttaaccgaa accttttgtt tatttatt gaccacaaca      2700 agaacatcaa caacaacaac cacgaaaaaa aagcgaatat atatttgttt gttcgtatat   2760
atatatatat ctaagcagat c                                             2781
```

<210> SEQ ID NO 8
<211> LENGTH: 768
<212> TYPE: PRT
<213> ORGANISM: Drosophila melanogaster
<220> FEATURE:

<400> SEQUENCE: 8

```
Met Gln Glu Phe Arg Ser His Leu Ile Phe Pro Ile Phe Gln Lys Val
1               5                   10                  15
```

-continued

```
Tyr Gln Ser Thr Ala Asn Arg Arg Ala Ser Ala Ser Val Leu Thr
             20                  25                  30

Asn Arg Leu Gly Lys Ala Leu Cys Leu Asn Cys Ala Arg Met Ser Lys
         35                  40                  45

Ser Pro Asp Gly Gly Ile Ser Glu Ile Glu Thr Glu Glu Pro Glu
 50                  55                  60

Asn Leu Ala Asn Ser Leu Asp Asp Ser Trp Arg Gly Val Ser Met Glu
 65                  70                  75                  80

Ala Ile His Arg Asn Arg Gln Pro Phe Glu Leu Glu Asn Leu Pro Pro
                 85                  90                  95

Val Thr Ala Gly Asn Leu His Arg Val Met Tyr Gln Leu Pro Ile Arg
                100                 105                 110

Glu Thr Pro Pro Arg Pro Tyr Lys Ser Pro Gly Lys Trp Asp Ser Glu
            115                 120                 125

His Val Arg Leu Pro Cys Ala Pro Glu Ser Lys Tyr Pro Arg Glu Asn
        130                 135                 140

Pro Asp Gly Ser Thr Thr Ile Asp Phe Arg Trp Glu Met Ile Glu Arg
145                 150                 155                 160

Ala Leu Leu Gln Pro Ile Lys Thr Cys Glu Glu Leu Gln Ala Ala Ile
                165                 170                 175

Ile Ser Tyr Asn Thr Thr Tyr Arg Asp Gln Trp His Phe Arg Ala Leu
            180                 185                 190

His Gln Leu Leu Asp Glu Glu Leu Asp Glu Ser Glu Thr Arg Val Phe
        195                 200                 205

Phe Glu Asp Leu Leu Pro Arg Ile Arg Leu Ala Leu Arg Leu Pro
    210                 215                 220

Asp Leu Ile Gln Ser Pro Val Pro Leu Leu Lys His His Lys Asn Ala
225                 230                 235                 240

Ser Leu Ser Leu Ser Gln Gln Ile Ser Cys Leu Leu Ala Asn Ala
                245                 250                 255

Phe Leu Cys Thr Phe Pro Arg Arg Asn Thr Leu Lys Arg Lys Ser Glu
            260                 265                 270

Tyr Ser Thr Phe Pro Asp Ile Asn Phe Asn Arg Leu Tyr Gln Ser Thr
        275                 280                 285

Gly Pro Ala Val Leu Glu Lys Leu Lys Cys Ile Met His Tyr Phe Arg
    290                 295                 300

Arg Val Cys Pro Thr Glu Arg Asp Ala Ser Asn Val Pro Thr Gly Val
305                 310                 315                 320

Val Thr Phe Val Arg Arg Ser Gly Leu Pro Glu His Leu Ile Asp Trp
                325                 330                 335

Ser Gln Ser Ala Ala Pro Leu Gly Asp Val Pro Leu His Val Asp Ala
            340                 345                 350

Glu Gly Thr Ile Glu Asp Glu Gly Ile Gly Leu Leu Gln Val Asp Phe
        355                 360                 365

Ala Asn Lys Tyr Leu Gly Gly Val Leu Gly His Gly Cys Val Gln
    370                 375                 380

Glu Glu Ile Arg Phe Val Ile Cys Pro Glu Leu Leu Val Gly Lys Leu
385                 390                 395                 400

Phe Thr Glu Cys Leu Arg Pro Phe Glu Ala Leu Val Met Leu Gly Ala
                405                 410                 415

Glu Arg Tyr Ser Asn Tyr Thr Gly Tyr Ala Gly Ser Phe Glu Trp Ser
            420                 425                 430

Gly Asn Phe Glu Asp Ser Thr Pro Arg Asp Ser Ser Gly Arg Arg Gln
```

```
              435                 440                 445
Thr Ala Ile Val Ala Ile Asp Ala Leu His Phe Ala Gln Ser His His
450                 455                 460
Gln Tyr Arg Glu Asp Leu Met Glu Arg Glu Leu Asn Lys Ala Tyr Ile
465                 470                 475                 480
Gly Phe Val His Trp Met Val Thr Pro Pro Gly Val Ala Thr Gly
                485                 490                 495
Asn Trp Gly Cys Gly Ala Phe Gly Gly Asp Ser Tyr Leu Lys Ala Leu
                500                 505                 510
Leu Gln Leu Met Val Cys Ala Gln Leu Gly Arg Pro Leu Ala Tyr Tyr
                515                 520                 525
Thr Phe Gly Asn Val Glu Phe Arg Asp Asp Phe His Glu Met Trp Leu
530                 535                 540
Leu Phe Arg Asn Asp Gly Thr Thr Val Gln Gln Leu Trp Ser Ile Leu
545                 550                 555                 560
Arg Ser Tyr Ser Arg Leu Ile Lys Glu Lys Ser Lys Glu Pro Arg
                565                 570                 575
Glu Asn Lys Ala Ser Lys Lys Leu Tyr Asp Phe Ile Lys Glu Glu
                580                 585                 590
Leu Lys Lys Val Arg Asp Val Pro Gly Glu Gly Ala Ser Ala Glu Ala
                595                 600                 605
Gly Ser Ser Arg Val Ala Gly Leu Gly Glu Gly Lys Ser Glu Thr Ser
610                 615                 620
Ala Lys Ser Ser Pro Glu Leu Asn Lys Gln Pro Ala Arg Pro Gln Ile
625                 630                 635                 640
Thr Ile Thr Gln Gln Ser Thr Asp Leu Leu Pro Ala Gln Leu Ser Gln
                645                 650                 655
Asp Asn Ser Asn Ser Ser Glu Asp Gln Ala Leu Leu Met Leu Ser Asp
                660                 665                 670
Asp Glu Glu Ala Asn Ala Met Met Glu Ala Ala Ser Leu Glu Ala Lys
                675                 680                 685
Ser Ser Val Glu Ile Ser Asn Ser Ser Thr Thr Ser Lys Thr Ser Ser
                690                 695                 700
Thr Ala Thr Lys Ser Met Gly Ser Gly Gly Arg Gln Leu Ser Leu Leu
705                 710                 715                 720
Glu Met Leu Asp Thr His Tyr Glu Lys Gly Ser Ala Ser Lys Arg Pro
                725                 730                 735
Arg Lys Ser Pro Asn Cys Ser Lys Ala Glu Gly Ser Ala Lys Ser Arg
                740                 745                 750
Lys Glu Ile Asp Val Thr Asp Lys Asp Glu Lys Asp Asp Ile Val Asp
                755                 760                 765
```

<210> SEQ ID NO 9
<211> LENGTH: 2181
<212> TYPE: DNA
<213> ORGANISM: Caenorhabditis elegans
<220> FEATURE:

<400> SEQUENCE: 9

| | | |
|---|---|---|
| atgagcaaga agtttatcga actgggtgat cctgtcactc aagacgagaa agactacgaa | 60 |
| gactatgtcg gagttggttt cgcgcatcaa gtcccgacaa tgaaaaggcg gaagttgaca | 120 |
| gaacatggaa atactacaga atcaaaagaa gatcctgaag agccaaaaag ccgtgacgta | 180 |
| tttgtctcct cgcagtcaag tgatgagagt caagaagatt cggctgaaaa tccggagatc | 240 |

-continued

| | |
|---|---|
| gctaaagaag tgtcagaaaa ttgtgaaaat ctgacagaaa ctctcaaaat ttctaatatt | 300 |
| gagagtttgg acaatgttac tgaaagatct gaacacactc ttgataatca caaaagtact | 360 |
| gaaccaatgg aagaagatgt aaacaacaag tccaatattg acgttgcgat taattctgac | 420 |
| gaggatgatg aacttgttct ggaagagaat aataaagaaa tgagggatgg agaacaagta | 480 |
| caacagttgt cacaggattt attcgctgat gatcaagagc taattgaata tccaggaatt | 540 |
| atgaaagaca ctacaactca actggatata acagattctg aagtggagac tgctcaaaaa | 600 |
| atggaaatga ttgaagaaac tgaagcagat tcgacatttg taggcgagga ttcaaaagct | 660 |
| acgaaaactg tgaggacatc cagttcaagt ttcctgtcaa ctgtttcaac atgcgaagcc | 720 |
| cctgcaaaag gacgagcaag aatgtatcaa aaagagttgg aaaagcatgt gattgcattt | 780 |
| actgagggaa atctcacact acaaccagat ttgaacaaag ttgatcccga cagaaactat | 840 |
| cgatattgta caattccgaa ctttccagct tcccaaggaa aacttcgaga gataatcga | 900 |
| tatgcccaa aaatcgtttt gcctcaaaga tggcgagaat ttgattcgag gggccgtaga | 960 |
| agagactcat atttctattt caaacgtaag ctcgatggaa tttgaaatg ctacaaaaca | 1020 |
| actggatatt ttatgtttgt tggacttttg cacaacatgt gggaatttga cccagacatc | 1080 |
| acatataaac tgccagcact ggaaatgtat acaaagaga gtcggaact tgttggtaga | 1140 |
| gaagaggttt tggaaaaatt tgcacgagtt gcccgcatcg caaaaactgc tgaagatatt | 1200 |
| ctgccagagc gaattatcg tcttgttggt gacgtcgaat cagctacctt gagccacaag | 1260 |
| caatgtgctg cacttgttgc gagaatgttt tttgcccgac cggacagtcc tttcagtttc | 1320 |
| tgccgaattc tctcgtctga taaatctatt tgtgtggaga aacttaaatt cctgttcact | 1380 |
| tatttcgaca aaatgtcaat ggatccaccg gatggtgccg tcagttttag acttacaaaa | 1440 |
| atggataaag atacgttcaa cgaagagtgg aaagataaaa aattacgttc tcttcctgaa | 1500 |
| gttgaattct ttgatgaaat gcttattgaa gacacagctc tctgtacaca gttgattttt | 1560 |
| gcgaacgaac atcttggtgg cggagttta atcatgggt ctgttcagga ggagatccgt | 1620 |
| ttcttgatgt gtccagaaat gatggttgga atgttgttgt gcgagaaaat gaacaactg | 1680 |
| gaagcgattt caattgttgg agcttacgtt ttcagttctt atactggtta tggtcatact | 1740 |
| ctaaaatggg cagaacttca accaaatcat tctcgtcaga atacaaacga atttcgagat | 1800 |
| cgttttggac gtcttcgggt agaaactatt gcaatcgatg caattctgtt caaaggatca | 1860 |
| aaattagatt gtcagacgga gcagttaaac aaagcaaata tcattaggga aatgaagaaa | 1920 |
| gcatctatcg gattcatgag ccagggaccg aaattcacaa atattccaat tgttactgga | 1980 |
| tggtggggat gtggagcatt taatggggac aagccactga agttcataat ccaagtaatt | 2040 |
| gctgccggag tcgctgatcg tccacttcat ttctgttcat ttggagaacc cgagcttgcc | 2100 |
| gcaaagtgca agaaaattat agaacgaatg aaacagaagg acgtaacact tggtaagtca | 2160 |
| tgttttcaa tcttcagttg a | 2181 |

<210> SEQ ID NO 10
<211> LENGTH: 726
<212> TYPE: PRT
<213> ORGANISM: Caenorhabditis elegans
<220> FEATURE:

<400> SEQUENCE: 10

Met Ser Lys Lys Phe Ile Glu Leu Gly Asp Pro Val Thr Gln Asp Glu
1               5                   10                  15

Lys Asp Tyr Glu Asp Tyr Val Gly Val Gly Phe Ala His Gln Val Pro

-continued

```
                 20                  25                  30
Thr Met Lys Arg Arg Lys Leu Thr Glu His Gly Asn Thr Glu Ser
         35                  40                  45
Lys Glu Asp Pro Glu Pro Lys Ser Arg Asp Val Phe Val Ser Ser
 50                  55                  60
Gln Ser Ser Asp Glu Ser Gln Glu Asp Ser Ala Glu Asn Pro Glu Ile
 65                  70                  75                  80
Ala Lys Glu Val Ser Glu Asn Cys Glu Asn Leu Thr Glu Thr Leu Lys
                 85                  90                  95
Ile Ser Asn Ile Glu Ser Leu Asp Asn Val Thr Glu Arg Ser Glu His
             100                 105                 110
Thr Leu Asp Asn His Lys Ser Thr Glu Pro Met Glu Glu Asp Val Asn
         115                 120                 125
Asn Lys Ser Asn Ile Asp Val Ala Ile Asn Ser Asp Glu Asp Asp Glu
 130                 135                 140
Leu Val Leu Glu Glu Asn Asn Lys Glu Met Arg Asp Gly Glu Gln Val
 145                 150                 155                 160
Gln Gln Leu Ser Gln Asp Leu Phe Ala Asp Asp Gln Glu Leu Ile Glu
             165                 170                 175
Tyr Pro Gly Ile Met Lys Asp Thr Thr Thr Gln Leu Asp Ile Thr Asp
             180                 185                 190
Ser Glu Val Glu Thr Ala Gln Lys Met Glu Met Ile Glu Glu Thr Glu
             195                 200                 205
Ala Asp Ser Thr Phe Val Gly Glu Asp Ser Lys Ala Thr Lys Thr Val
         210                 215                 220
Arg Thr Ser Ser Ser Phe Leu Ser Thr Val Ser Thr Cys Glu Ala
 225                 230                 235                 240
Pro Ala Lys Gly Arg Ala Arg Met Tyr Gln Lys Glu Leu Glu Lys His
             245                 250                 255
Val Ile Ala Phe Thr Glu Gly Asn Leu Thr Leu Gln Pro Asp Leu Asn
             260                 265                 270
Lys Val Asp Pro Asp Arg Asn Tyr Arg Tyr Cys Thr Ile Pro Asn Phe
         275                 280                 285
Pro Ala Ser Gln Gly Lys Leu Arg Glu Asp Asn Arg Tyr Gly Pro Lys
         290                 295                 300
Ile Val Leu Pro Gln Arg Trp Arg Glu Phe Asp Ser Arg Gly Arg Arg
 305                 310                 315                 320
Arg Asp Ser Tyr Phe Tyr Lys Arg Lys Leu Asp Gly Tyr Leu Lys
             325                 330                 335
Cys Tyr Lys Thr Thr Gly Tyr Phe Met Phe Val Gly Leu Leu His Asn
             340                 345                 350
Met Trp Glu Phe Asp Pro Asp Ile Thr Tyr Lys Leu Pro Ala Leu Glu
         355                 360                 365
Met Tyr Tyr Lys Glu Met Ser Glu Leu Val Gly Arg Glu Val Leu
 370                 375                 380
Glu Lys Phe Ala Arg Val Ala Arg Ile Ala Lys Thr Ala Glu Asp Ile
 385                 390                 395                 400
Leu Pro Glu Arg Ile Tyr Arg Leu Val Gly Asp Val Glu Ser Ala Thr
             405                 410                 415
Leu Ser His Lys Gln Cys Ala Ala Leu Val Ala Arg Met Phe Phe Ala
             420                 425                 430
Arg Pro Asp Ser Pro Phe Ser Phe Cys Arg Ile Leu Ser Ser Asp Lys
         435                 440                 445
```

```
Ser Ile Cys Val Glu Lys Leu Lys Phe Leu Phe Thr Tyr Phe Asp Lys
    450                 455                 460

Met Ser Met Asp Pro Pro Asp Gly Ala Val Ser Phe Arg Leu Thr Lys
465                 470                 475                 480

Met Asp Lys Asp Thr Phe Asn Glu Glu Trp Lys Asp Lys Lys Leu Arg
                485                 490                 495

Ser Leu Pro Glu Val Glu Phe Phe Asp Glu Met Leu Ile Glu Asp Thr
            500                 505                 510

Ala Leu Cys Thr Gln Val Asp Phe Ala Asn Glu His Leu Gly Gly Gly
        515                 520                 525

Val Leu Asn His Gly Ser Val Gln Glu Glu Ile Arg Phe Leu Met Cys
    530                 535                 540

Pro Glu Met Met Val Gly Met Leu Leu Cys Glu Lys Met Lys Gln Leu
545                 550                 555                 560

Glu Ala Ile Ser Ile Val Gly Ala Tyr Val Phe Ser Ser Tyr Thr Gly
                565                 570                 575

Tyr Gly His Thr Leu Lys Trp Ala Glu Leu Gln Pro Asn His Ser Arg
            580                 585                 590

Gln Asn Thr Asn Glu Phe Arg Asp Arg Phe Gly Arg Leu Arg Val Glu
        595                 600                 605

Thr Ile Ala Ile Asp Ala Ile Leu Phe Lys Gly Ser Lys Leu Asp Cys
610                 615                 620

Gln Thr Glu Gln Leu Asn Lys Ala Asn Ile Ile Arg Glu Met Lys Lys
625                 630                 635                 640

Ala Ser Ile Gly Phe Met Ser Gln Gly Pro Lys Phe Thr Asn Ile Pro
                645                 650                 655

Ile Val Thr Gly Trp Trp Gly Cys Gly Ala Phe Asn Gly Asp Lys Pro
            660                 665                 670

Leu Lys Phe Ile Ile Gln Val Ile Ala Ala Gly Val Ala Asp Arg Pro
        675                 680                 685

Leu His Phe Cys Ser Phe Gly Glu Pro Glu Leu Ala Ala Lys Cys Lys
    690                 695                 700

Lys Ile Ile Glu Arg Met Lys Gln Lys Asp Val Thr Leu Gly Lys Ser
705                 710                 715                 720

Cys Phe Ser Ile Phe Ser
                725

<210> SEQ ID NO 11
<211> LENGTH: 31
<212> TYPE: PRT
<213> ORGANISM: Bos taurus
<220> FEATURE:

<400> SEQUENCE: 11

Leu Phe Thr Glu Val Leu Asp His Asn Glu Cys Leu Ile Ile Thr Gly
1               5                   10                  15

Thr Glu Gln Tyr Ser Glu Tyr Thr Gly Tyr Ala Glu Thr Tyr Arg
            20                  25                  30

<210> SEQ ID NO 12
<211> LENGTH: 29
<212> TYPE: PRT
<213> ORGANISM: Bos taurus
<220> FEATURE:

<400> SEQUENCE: 12
```

```
Ala Tyr Cys Gly Phe Leu Arg Pro Gly Val Ser Ser Glu Asn Leu Ser
1               5                   10                  15

Ala Val Ala Thr Gly Asn Xaa Gly Cys Gly Ala Phe Gly
                20              25
```

<210> SEQ ID NO 13
<211> LENGTH: 11
<212> TYPE: PRT
<213> ORGANISM: Bos taurus
<220> FEATURE:

<400> SEQUENCE: 13

```
Phe Leu Ile Asn Pro Glu Leu Ile Val Ser Arg
1               5                   10
```

<210> SEQ ID NO 14
<211> LENGTH: 16
<212> TYPE: PRT
<213> ORGANISM: Bos taurus
<220> FEATURE:

<400> SEQUENCE: 14

```
Ile Ala Leu Xaa Leu Pro Asn Ile Xaa Thr Gln Pro Ile Pro Leu Leu
1               5                   10                  15
```

<210> SEQ ID NO 15
<211> LENGTH: 17
<212> TYPE: DNA
<213> ORGANISM: Bos taurus
<220> FEATURE:

<400> SEQUENCE: 15
gaycayaayg artgyyt                                              17

<210> SEQ ID NO 16
<211> LENGTH: 17
<212> TYPE: DNA
<213> ORGANISM: Bos taurus
<220> FEATURE:

<400> SEQUENCE: 16
ckrtangtyt cngcrta                                              17

<210> SEQ ID NO 17
<211> LENGTH: 24
<212> TYPE: DNA
<213> ORGANISM: Bos taurus
<220> FEATURE:

<400> SEQUENCE: 17
atcatcacag gtactgagca gtac                                      24

<210> SEQ ID NO 18
<211> LENGTH: 24
<212> TYPE: DNA
<213> ORGANISM: Bos taurus
<220> FEATURE:

<400> SEQUENCE: 18
gcctgtgtat tcactgtact gctc                                      24

<210> SEQ ID NO 19
<211> LENGTH: 26
<212> TYPE: PRT
<213> ORGANISM: Bos taurus

```
<220> FEATURE:

<400> SEQUENCE: 19

Glu Asp Lys Arg Lys Glu Gln Cys Glu Met Lys His Gln Arg Thr Glu
1               5                   10                  15

Arg Lys Ile Pro Lys Tyr Ile Pro Pro His
            20                  25

<210> SEQ ID NO 20
<211> LENGTH: 26
<212> TYPE: PRT
<213> ORGANISM: Homo sapiens
<220> FEATURE:

<400> SEQUENCE: 20

Glu Asp Arg Arg Lys Glu Gln Trp Glu Thr Lys His Gln Arg Thr Glu
1               5                   10                  15

Arg Lys Ile Pro Lys Tyr Val Pro Pro His
            20                  25

<210> SEQ ID NO 21
<211> LENGTH: 26
<212> TYPE: PRT
<213> ORGANISM: Mus Musculus
<220> FEATURE:

<400> SEQUENCE: 21

Glu Asp Arg Arg Lys Glu Gln Cys Glu Val Arg His Gln Arg Thr Glu
1               5                   10                  15

Arg Lys Ile Pro Lys Tyr Ile Pro Pro Asn
            20                  25

<210> SEQ ID NO 22
<211> LENGTH: 32
<212> TYPE: PRT
<213> ORGANISM: Caenorhabotitis elegans
<220> FEATURE:

<400> SEQUENCE: 22

His Gln Val Pro Thr Met Lys Arg Arg Lys Leu Thr Glu His Gly Asn
1               5                   10                  15

Thr Thr Glu Ser Leu Leu Leu Lys Glu Asp Pro Pro Glu Pro Lys Ser
            20                  25                  30

<210> SEQ ID NO 23
<211> LENGTH: 26
<212> TYPE: PRT
<213> ORGANISM: Homo sapiens
<220> FEATURE:

<400> SEQUENCE: 23

Glu Gly Lys Arg Lys Gly Asp Glu Val Asp Gly Val Asp Glu Val Ala
1               5                   10                  15

Lys Lys Lys Ser Lys Lys Glu Lys Asp Lys
            20                  25

<210> SEQ ID NO 24
<211> LENGTH: 26
<212> TYPE: PRT
<213> ORGANISM: Mus musculus
<220> FEATURE:

<400> SEQUENCE: 24
```

```
Glu Gly Lys Arg Lys Gly Asp Glu Val Asp Gly Thr Asp Glu Val Ala
1               5                   10                  15

Lys Lys Lys Ser Arg Lys Glu Thr Asp Lys
                20                  25

<210> SEQ ID NO 25
<211> LENGTH: 26
<212> TYPE: PRT
<213> ORGANISM: Bos taurus
<220> FEATURE:

<400> SEQUENCE: 25

Glu Gly Lys Arg Lys Gly Asp Glu Val Asp Gly Ile Asp Glu Val Thr
1               5                   10                  15

Lys Lys Lys Ser Lys Lys Glu Lys Asp Lys
                20                  25

<210> SEQ ID NO 26
<211> LENGTH: 25
<212> TYPE: PRT
<213> ORGANISM: Galus galus
<220> FEATURE:

<400> SEQUENCE: 26

Glu Gly Lys Arg Lys Gly Glu Glu Val Asp Gly Asn Val Val Ala Lys
1               5                   10                  15

Lys Lys Ser Arg Lys Glu Lys Glu Lys
                20                  25

<210> SEQ ID NO 27
<211> LENGTH: 26
<212> TYPE: PRT
<213> ORGANISM: Xenopus laevis
<220> FEATURE:

<400> SEQUENCE: 27

Glu Gly Lys Arg Lys Ala Asp Glu Val Asp Gly His Ser Ala Ala Thr
1               5                   10                  15

Lys Lys Lys Ile Lys Lys Glu Lys Glu Lys
                20                  25

<210> SEQ ID NO 28
<211> LENGTH: 25
<212> TYPE: PRT
<213> ORGANISM: Drosophila melanoguster
<220> FEATURE:

<400> SEQUENCE: 28

Glu Glu Leu Pro Asp Thr Lys Arg Ala Lys Met Glu Leu Ser Asp Thr
1               5                   10                  15

Asn Glu Glu Gly Glu Lys Lys Gln Arg
                20                  25

<210> SEQ ID NO 29
<211> LENGTH: 31
<212> TYPE: PRT
<213> ORGANISM: Sarcophaga peregrina
<220> FEATURE:

<400> SEQUENCE: 29

Glu Gly Val Ser Ser Ala Lys Lys Ala Lys Ile Glu Lys Ile Asp Glu
1               5                   10                  15

Glu Asp Ala Ala Ser Ile Lys Glu Leu Thr Glu Lys Ile Lys Lys
```

<210> SEQ ID NO 30
<211> LENGTH: 28
<212> TYPE: DNA
<213> ORGANISM: Bos taurus
<220> FEATURE:

<400> SEQUENCE: 30
gctgcgggtc tcgacgatga gtgcgggc                              28

<210> SEQ ID NO 31
<211> LENGTH: 29
<212> TYPE: DNA
<213> ORGANISM: Bos taurus
<220> FEATURE:

<400> SEQUENCE: 31
gcgtctagaa ttcacttggc tcctcaggc                             29

<210> SEQ ID NO 32
<211> LENGTH: 38
<212> TYPE: DNA
<213> ORGANISM: Bos taurus
<220> FEATURE:

<400> SEQUENCE: 32
ccggaattcg ggttttttgt taatgaaaat ttattaac                   38

<210> SEQ ID NO 33
<211> LENGTH: 29
<212> TYPE: DNA
<213> ORGANISM: Bos taurus
<220> FEATURE:

<400> SEQUENCE: 33
tcagagcaga tgaactcgag cagtccagg                             29

<210> SEQ ID NO 34
<211> LENGTH: 61
<212> TYPE: DNA
<213> ORGANISM: Bos taurus
<220> FEATURE:

<400> SEQUENCE: 34
ccaatttgaa ggaggaattc ccgccgccac catgaatgat gtgaatgcca aacgacctgg   60
a                                                                  61

<210> SEQ ID NO 35
<211> LENGTH: 22
<212> TYPE: DNA
<213> ORGANISM: Artificial sequence
<220> FEATURE: Kozak consensus sequence
<223> OTHER INFORMATION: Synthesized by oligonucleotide synthesizer

<400> SEQUENCE: 35
gaattcccgc cgccaccatg aa                                    22

<210> SEQ ID NO 36
<211> LENGTH: 674
<212> TYPE: DNA
<213> ORGANISM: Homo sapiens
<220> FEATURE:

<400> SEQUENCE: 36

```
agaagaaaat ggccaaggca tgctacaggt ggattttgca atcgttttg ttggaggtgg      60 tgtaaccagt gcaggacttg tgcaagaaga atccgctttt taatcaatc ctgagttgat     120 tatttcacgg ctcttcactg aggtgctgga tcacaatgaa tgtctaatta tcacaggtac    180
tgagcagtac agtgaataca caggctatgc tgagacatat cgttggtccc ggagccacga    240
agatgggagt gaaagggacg actgcgagcg gcgctgcact gagatcgttg ccatcgatgc    300
tcttcacttc agacgctacc tcgatcagtt tgtgcctgag aaaatgagac gcgagctgaa    360
caaggcttac tgtggatttc tccgtcctgg agtttcttca gagaatcttt ctgcagtggc    420
cacaggaaac tggggctgtg gtgcctttgg gggtgatgcc aggttaaaag ccttaataca    480
gatattggca gctgctgcag ctgagcgaga tgtggtttat tcacctttg gggactcaga     540 attgatgaga gacatttaca gcatgcacat tttccttact gaaaggaaac tcactgttgg    600
agatgtgtat aagctgttgc tacgatacta caatgaagaa tgcagaaact gttccacccc    660
tggaccagac atca                                                      674

<210> SEQ ID NO 37
<211> LENGTH: 200
<212> TYPE: DNA
<213> ORGANISM: Homo sapiens
<220> FEATURE:

<400> SEQUENCE: 37
aaaaatagtt gtcaagactc agaagcagat gaggagacaa gtccaggttt tgatgaacaa     60
gaagatggta gttcctccca acagcaaat aaaccttcaa ggttccaagc aagagacgct     120
gacattgaat ttaggaaacg gtactctact aagggcggtg aagttagatt acatttccaa    180
tttgaaggag gagagagtcg                                                200

<210> SEQ ID NO 38
<211> LENGTH: 29793
<212> TYPE: DNA
<213> ORGANISM: Caenorhabaditis elegans
<220> FEATURE:

<400> SEQUENCE: 38
gatctcgaag taaaaactca cgcagaaaga gctcctcctc ctttagcatg agaatccaac     60
tttgtaatga taacactggc aacatcaaca gtttgagaga agcacgtgc ttgggcttca     120 caagcttgtc aatagaagc atccatcaca aaaacaacat tatctggtgt aactgcgttg    180
gaaacttgga gcatttcttc gaaaagtgaa gcttcttgct tgtgacgacc tgatgtatca    240
acaatgatga tttcgaaccc ttcttgctgc aaaacaaata ttattaaacc attttctgt    300 gataaattac cgtgaatttt tctactcctt cggcggcaat ttttacgggg tcaatttcag    360
agtatgatcc atagaaggga atacgagctt ttgtggcatt ttgctttaat tgatcaaaag    420
ctccagcacg gaatgtatcg gcacagatca gacatgtttt ccatccttt ctttggtagt     480 aatacgccat ctgaacttga aaagtgttga aagttgttg gaagtttact aattaaaaaa    540
tataatgttt gatggtgtgt gagctttcta ttgtaattca tggaacgaac cttggtacaa    600
gtcgtagttt taccggaacc ttgaagacca acaaacatga aaacgttgcg acgtcctttt    660
gttggtgtga aaggagttac accaggatcc acaagcttca gcagttcatt gaatactgtc    720
ttctgaatgt accgacgttt gtttgctcct ccgacgatct cttcgaaatt aatcgctttt    780
ctgaaaatat ttattaaatt taaatcttaa atagcgtaaa aatttacttc acgttgtcct    840
```

-continued

```
taagttgctt tacaagacga atatgaacat cagattcaat aagagctgta cagacttctt    900
tcagcatcaa atccagctcc ccctcattga taacggtgct ctgaccgagc tttccgatcg    960
catttcggat tttccgcccc aaatcggcca aaaccatttt gaactgaaat ttgaaatgct   1020
ttaatttgtt taagcataga attaaacgcg ttttaaatcg agagcaccat aaaaacagtt   1080
tggagaaaaa tcgataattc ttgtaggaga ttcagtccct gtggttttct tcggcttcct   1140
aatcattttt tgacgacata gtggtatttc acataggtt ttttcaagac acaacagatt   1200
tttcacaaag agtagagaag aaatggaaaa ctgtagattt cttctcgaag agccgagaaa   1260
ggcaaggtat tggaagttta aaaggtaat gtttctttat tcttttttca aaacaataat   1320
aaatggaaaa tatatattta tagataacaa tttcagacag ttaaaatcac gtgaaaaatt   1380
caaatttcaa cacaaaaatt gacgagtgga accccgttgt tgcgccttga agagtaacgc   1440
ttgcgcgttt gacgatttta ttgacgcgtt tctggtgcat gcgggaaatt ttttatttc    1500
aacttttttc ctgtttgttt atcctttttt aattgaattc tcatgatttg aaagctttga   1560
aaaatattat tttgctcaaa aacatgcgtt ttgtaaaaca ttgattagat tcaaggcaat   1620
taatggattt ttgcacgttc caaaaaaaag gaaattcatt ttttgaaaat tttgataatt   1680
taataatgaa aaatgttcca tagatttatt caatgccatc cttctctata atctcgaact   1740
tccgcatcct tcaactgtgg tagaggtatt tgcaatacca tatagtcgta ataataaact   1800
ttagtgaaca aatccaagac atcagctctt gagtaaatga atgatttata aaaactgctg   1860
attttctcgt aggaagaaag agaatcagct aataatccgt cgttgtctat tctgtcaggc   1920
cgcttaaatg ttaaaaaata aaaacgtttt aagctaattt tgtatgtcta gaaactctaa   1980
ctcacaagca tttctgcata cgccggatta gttggttttg caaaaagcga gtaatctaca   2040
aaagtgaatt tttgattcat ctcttccatt tcacaaaacc aattttgtgg tacgtatttc   2100
atatgatctt catccacttt tttagttttt gaatgtattt gtgtgagttg tgtccagatt   2160
tgaataagat aacatctcag atccaacttg caattgaagc aagaacgatc ttctctgaaa   2220
ttttatatga ccttaaactt tatacttttg tagtttcgtc gatatctgat cgttcagttg   2280
tataggtatg tacatctcta ggtttatgtg ctacacgaaa atataatttg ttttacctaa   2340
cacacgcatc cataaaatga tctacaaatc gttcaattgg atcctgtctt ggaaataata   2400
atttccaatt cgtaaagttt gcattcaact catttctcg tttcaaatcg tcgatatccg   2460
caaaatatgt tagtgaatca ctatcacaca ctctgaaaag cacaatattc atatttcgta   2520
gttaataatg aacctcacga ttcatcatta aatttctctt ggagcccgca taatacttgc   2580
tgcccaatta aagtatcagt ttcacagatt gcagttctat catttccgat agcctcaaat   2640
aagatttaat cttaagcgag tgttctgatc aatttaaata tttgatactc accgcaagtt   2700
tcttcgaaac ttgttcgaaa gctggaattt tagaatatcc ttcaaaactt tttcctcgc    2760
cctcatcaag ccataataag ttttgatcag caatatattc gaataaatta gtctctgata   2820
aatctcgtat cacaatcttt ttttctactc taaagaatac aatttgata agaatgataa    2880
taattataat tataatagtt cgtcgctgag ttgatgaaga ccacataatt agtttaatgg   2940
caagctatgc aacttgttga atactaatag gacttagcaa atcttatctt gaacctttt    3000
cattcgaaag aaaaatgaga tcgaatctcg ttcaaactgt ggagtagtca gttaagaaac   3060
ttgtttctag tttgtgagga gacactggag aacgtgaaag tattacccat acgcaatatt   3120
tttgcggcga aaaatacggt acccggtctc gacacgacag ttttaaaac ttgtaaatag    3180
gtatgtaaaa gaaaacttta attttaaacg tgttgtttcg gaattttcat cgttttgtca   3240
```

```
tagttattct acaaataatt atttatgaaa aaaaaactaa aatataacta taataacacc     3300
tgaatattaa caaatcgatc gaaaaaaaac tatgaaaaaa atggatgaaa attccgcagc     3360
aacgagagtt tgaaatttca gtattcttta aaggcttacc gatttcaata aatagtgaca     3420
ctgaaaattg tagttttaaa actagttggt tagtatcatc aaatattcaa tccttcaaaa     3480
attcctcaat attaacgtat tttctctaat tgtcttcatt atctaaaaaa aagttgcaat     3540
atattttttcc aggcagaaat agactttcac aaaacacatc gacacttcga atgagcaaga    3600
agtttatcga actgggtgat cctgtcactc aagacgttag ttatagttttt tattacttga    3660
acattatcat cttttttacag gagaaagact acgaagacta tgtcggagtt ggtttcgcgc    3720
atcaagtccc gacaatgaaa aggcggaagt tgacagaaca tggaaatact acagaatcaa    3780
aagaagatcc tgaagagcca aaagccgtg  acgtatttgt ctcctcgcag tcaagtgatg    3840
agagtcaaga agattcggct gaaaatccgg agatcgctaa agaagtgtca gaaaattgtg    3900
aaaatctgac agaaactctc aaaatttcta atattgagag tttggacaat gttactgaaa    3960
gatctgaaca cactcttgat aatcacaaaa gtactgaacc aatggaagaa gatgtaaaca    4020
acaagtccaa tattgacgtt gcgattaatt ctgacgagga tgatgaactt gttctggaag    4080
agaataataa agaaatgagg gatggagaac aagtacaaca ggtcaggaaa ttttacaagt    4140
gaatgaaata agttaatcac caaaatgaat aaggacattt cccatcagaa aggtcttctg    4200
aattttaggt gtaatgttaa ttttttgctg tagtttttcc cattgtttga aatttttgcc    4260
aaaattagtt attgcatacc cttcatgttt ttgaagattg tttaggaatg agaaaacatt    4320
ttggacgctt ttattattag gacaccaaac acttttttgtt gaaaaaacag ctcgtttaaa   4380
aaaagctttt tccaaaaaat ctgacgcaag gcttgtgaat tttcgttttc ccctgatttt    4440
taaaatttct cctaaagttt tttgctaata tttttcgcta tcgcgtaatt tactagtgaa    4500
tcaacaaaaa atttttttttt tttcatagat tttttataag ttttttgaaaa catagattta   4560
aaacttaaac ttaaattttg acaaggcgag aggaaaaaat taaaaattgc tgaacattca    4620
gatgccggtt accttatttt tggttcaaaa atcccaatat tacgcgtctg ggttatagtc    4680
atttgccttt attaaattaa tggtgttcct tggaaaagta agttctgttt tgttttcagc    4740
ttatcacttc atcaaacgga aggaaaggtt gattaaggaa agtaaacata ttttatgttg    4800
ttcttgtcac ttcctccatt tcgcaataat ataactcgag aaatatagaa ttttgttcga    4860
agttttcttt ttccttcaac attttaaata ttgttagtat tacccagaaa aatagaaaaa    4920
atcgaagaaa tttgcaaaaa agcagacgta gaggctacgt acttcttaag cacgcccctt    4980
ttctttttaaa tttgttcggt cgtaccgaga tccggtacct tattttacaa cgttttctgt    5040
tccaaaaata ataatgtact gcagttgtca caggatttat tcgctgatga tcaagagcta    5100
attgaatatc caggaattat gaaagacact acaactcaac tggatataac agattctgaa    5160
gtggagactg ctcaaaaaat ggaaatgatt gaagaaactg aagcagattc gacatttgta    5220
ggcgaggatt caaaagtgag acaaaatcat tctgacaagg attcctgcga gcactcagtc    5280
aagagcgagt cacggcaact cggtccaaaa ccatttctaa ttagtaaact ctcaaaaacc    5340
acaactaaat agcttaaaac ctttgtaaat tagcttattt ttgctaatta gcaatgattt    5400
taagctaatt agttgtggtt tttgagagtt tactaattag aaatggtttt ggaccgagtt    5460
gccgtgactc gctcttgact gagcacaagc aaacttttgt ggatgttgag aatcagcggc    5520
aaagtggcac tactagtgac gaagttgacg cagattctca gattaatttg gtaagacaaa    5580
```

```
gaaaatataa attttattac ccagatgcat attttcatga ttctgatgca aaaaatacgg    5640
tacccgatct ggatactaca attttttgtaa aatgcgaaaa ggtttgcacc tttaaaaaga   5700
actgcaattt caaacacttg ttgctgtgga ttgtttatcg gtttttaata tttttttggtg  5760 agagtaaatg agaaaagcga gttcccgcat tatctgtgtg cgatttggaa tacagtactt   5820
ttcaaagacg cacaccattt tgcatataac aaacatttgt cgtgtcgaaa ccgggtaccg   5880
tgattttgca ttaaaagttg caaaatttca catagttttt ataatttagg ctacgaaaac   5940
tgtgaggaca tccagttcaa gtttcctgtc aactgtttca acatgcgaag cccctgcaaa   6000
aggacgagca agaatgtatc aaaaagagtt ggaaaagcat gtgattgcat ttactgaggg   6060
aaatctcaca ctacaaccag atttgaacaa agttgatccc gacagaaact atcgatattg   6120
tacaattccg aactttccag cttcccaagg aagtacgttg ttcaataaaa catactaggt   6180
atataattaa ttatttcaga acttcgagaa gataatcgat atggcccaaa aatcgttttg   6240
cctcaaagat ggcgagaatt tgattcggta catttctatt gaattaatta tatactactt   6300
actagaaaca ccatggagaa agaatgcaaa aaattgaatt ttaaaaacta attttttaat   6360
tttggctaaa ttttcagttt gaatttaatc caaaatgaaa actgcgacca atcaatgact   6420
tttcaaaatc acttttcaac caatcaaacg gagtgtgctg ggctcgaaga cgctgattgg   6480
ttcggaaatg ggcgtggttt ctcattttgg agggaattca aaaaaaggca tttggtcaca   6540
gttgaaaatc atgttttcaa aagatgcatt ttttattcct tctcgatttt ttttgatttt   6600
cttttgtggt atttctgaat ttaaaggtgg tgtagtcgaa ttttttttatt gctttattag   6660 actcaaaatt ttctgaaaac gccaaatttc ataatgaaac ttcttgaaaa ctcttcagca   6720
aaaagttatg acgctcaaa aaatggccta aaattagtta agattggaga tttgaccgac    6780
ttgtcaatgt cgcagcggct ggaaacaatt tttttttgaaa tcaccgtcaa atttttaagta 6840 tacaacttga ttattttgcg tttttaaactt tatttaggta tttaaaagtc gatggacggc   6900
gagttttggc tcaaaaaaat taaaaatctc gccgtccatc gatttttaaa taccttaatc   6960
aagaataaaa caaaggtag gcaacttgta tattcaaaat ttgacggtga ttgcaacttt    7020
taactaattt caggccattt tttgagccgt cataacttt ttctaaaaag ttttcaagaa    7080
gtttcattat gaaattcggt gttttcagac aattttgagt ctaataagga aataaaaaaa   7140
attcgagtac accaccttta agaaaatttt ggatttccgc tacgctaatc cacctttaat   7200 caaaatatt tgaagttatt caagttaaa gaattatatt ttcagagggg ccgtagaaga    7260
gactcatatt tctatttcaa acgtaagctc gatggatatt tgaaatgcta caaaacaact   7320
ggatatttta tgtttgttgt aagttttga aatacaattc gtttgaagat ttactctatt    7380
ttcagggact tttgcacaac atgtgggaat ttgacccaga catcacatat aaactgccag   7440
cactggaaat gtattacaaa gagatgtcgg aacttgttgg tagagaagag gttttggaaa   7500
aatttgcacg agttgcccgc atcgcaaaaa ctgctgaaga tattctgcca gaggtatgat   7560
ttatgagata tacagcattt cctctaatag tattgcatat aaacatttca ctttgaggtt   7620
atatcttggt ttatttaaa aatatcaata aatacaaaac aatagaaaaa tgataaaaaa   7680
acattttgtc agttgataat ttgggtatag tattcattca taatttgatt tttttagcga   7740
atttatcgtc ttgttggtga cgtcgaatca gctaccttga gccacaagca atgtgctgca   7800
cttgttgcga gaatgttttt tgcccgaccg gacagtcctt tcagtttctg ccggtgagta   7860
atacaagaat gctcatattt ttagaatcaa tatttgcaag gaactttaat cttacgtacg   7920
tcttaagatg agcatttcg cacatatctt acgcgcacga gtctcgacac gcgaacatcg    7980
```

```
agcttctgta actcgtatca atttacaagc cgttattaca tcagtttttta atgaatttta   8040 agaaaatcgt gcaaaagtag tgtcgagagc cattcgcgta agatatggtg agatttatca   8100
tttttagacg tctagtggat atctaacaaa actttataca tttttatttc agaattctct   8160
cgtctgataa atctatttgt gtggagaaac ttaaattcct gttcacttat ttcgacaaaa   8220
tgtcaatgga tccaccggat ggtgccgtca gttttagact tacaaaaatg gataaagata   8280
cgttcaacga agagtggaaa gataaaaaat tacgttctct tcctgaagtt gaattctttg   8340
atgaaatgct tattgaagac acagctctct gtacacaagt tgattttgcg aacgaacatc   8400
ttggtggcgg agttttaaat catgggtctg ttcaggtagt tatttaaagg aatataagaa   8460
tttgaagttt tattttttt atgcaggagg agatccgttt cttgatgtgt ccagaaatga   8520
tggttggaat gttgttgtgc gagaaaatga acaactgga agcgatttca attgttggag   8580
cttacgtttt cagttcttat actggttatg gtaagtctag actttcaaaa aaaactgttc   8640
caatatgtca atatatttca ggtcatactc taaatgggc agaacttcaa ccaaatcatt   8700
ctcgtcagaa tacaaacgaa tttcgagatc gttttggacg tcttcgggta gaaactattg   8760
caatcgatgc aattctgttc aaaggatcaa aattagattg tcagacggag cagttaaaca   8820
aagcaaatat cattagggaa atgaagaaag catctatcgg attcatgagc cagggaccga   8880
aattcacaaa tattccaatt gttactggat ggtggggatg tggagcattt aatggggaca   8940
agccactgaa gtgtatgtta tttcattcgt taaatattga agatggagga gagtgaatgg   9000
ggattttgct tcttttgcaa aatggcctcc ctatgtacct gaaaaaaaaa tgaaaaaatc   9060
gagaaatatt gaaaaccaaa caacgaattt ttcacaattt tgcctaaatt tttgaatttt   9120
cgccaaaatc ggaatcagcg attcgctcca cccatttttc cgccaatcat ttataatgtg   9180
cggagctcaa aaacactgat tggctagaaa gtgggcgtag cttcttattt cggaggaaat   9240 tcaaatagg aagttaatct aaattaaaac aatctcgtta aaaaatgttt ctttttttcaa   9300 tcttccctat ttgttaaat tttttcttttt aaagatcgtc taaaagctac cagtatctga   9360
ttcaattatc ggttttttc agtcataatc caagtaattg ctgccggagt cgctgatcgt   9420
ccacttcatt tctgttcatt tggagaaccc gagcttgccg caaagtgcaa gaaaattata   9480
gaacgaatga aacagaagga cgtaacactt ggtaagtcat gtttttcaat cttcagttga   9540
tttgaaaaag ttgtatcgag ttggaaacag cttttaatct aaattctgct aacttacagg   9600
catgctattc agtatgataa acaacaccgg cttgccacat aagcactttg aattctacgt   9660
cttcgataga atttctactt atctcagtag ttcggaagat gttgagtctt cgaaatcatc   9720
accttcagta tcccgagcat aattcgaatc gcccacacgg ccataaagac cggttccttt   9780
cgattaaatt ctgttaaata tgcatgctcc gtctttaaaa aatcagtccc cgtatttaa   9840 acgttttgat tttaatgttc atattattat ccgaaattag tatactcgcc gtcatgaaag   9900
cccgagatat ctagttcgca agtcagaaat ttttcggagc atcgtcgtga tatatgaata   9960
aatacattcc tgtttttcac aagtgtagtg tgaaaccaat ccatgcagac gtttatttct   10020
gaattaattt tgaaacagat ttcagagaca gtgaggttga cattagatat gggcaagtaa   10080
caataacagc agggcagtta ttatgattat ggatgctgat ataggaaagt cagaacagta   10140
taatcgacga gaataaaaag agatgagaag ataggcgaga ataaagaacg ttaacgaaaa   10200
tcactgaaga gctacatttc caacagaata agaaatgtag ttggaaatcc ctaatcaaac   10260
agaaaagcga gaaatcatga ctttcgagat aaagagattt atctgcaaac aattcttgaa   10320
```

```
cataaaatta aagcaccaca gactgtccaa attataaaat cagtttctcg ctacagtctg   10380
ggggtactct agttccattc aaaaacttct tgcaaacaaa gagaaataaa cagacttgta   10440
cgggacacat ataaaatcta agcatgcttt gaaaagcgga gaacatacga tctattcggg   10500
gatatacata tatatatata tatttcatct catctagagg atcaccatcg ttactcatca   10560
aattggttgg tgtggtggaa gttatgaaaa gagcaatttt aaccgaaaat caccaaaaca   10620
gaaaccaaat taatgtataa tcgacgagaa tcatgatgag atgatgattt gcttctagca   10680
gaagtttaga agcacatgct atcattcatg ctcacgatga cgataggttc gttatgcatt   10740
cttgaagcca atgacacttc cattgctcct tctcttgcgc tcacacaatt tccattctcg   10800
tcgtaaatcg ttcgactttc gaatatccac atcttaccgg gcggcacttt tggcctggtt   10860
tggcagatct gaaataaaat cttttcataa tttaaagtct gatatcccga gaaacaatag   10920
ctgaattgaa acagaagaat aaatctcacc tgaatatcca cgtttgcaag tgaagtttct   10980
ttcacaaacg gctgtgtttc ctcatagaga tcatctgaac cgtaggagaa tggacggagc   11040
aagtcgttca gcttcctcat gtgctgttca tttgccggtc tcacgtgctt ctttacggga   11100
gcagtggcgg cagcatacgc tgatttagat gctcgcatag tgtcattcct acgactttga   11160
ggcttccttt cattgttgta atgcggttgc atttggaacg gtgcgttttg aaatcctcgc   11220
atgacttgag acgattgatg atgcgatggt ggaggaatgt ctgcaagatt atagttatgt   11280
attaaaaatc aaaaatttgt gtggttccca ttttaaaata aaaaaaaaat atttttacgc   11340
actttgctga ggcaaccgat aactatttcc tcgctggcga ctacttctct tattgtgagc   11400
attatagctc atgttctcat gattgagttg acctgaacga tcaaggttaa aactaggcct   11460
aaaactagtc aaaattactg agtttctcct tccacgtcgt ctgtcgagca ggctccgagt   11520
acatttttac tggaaaacta taataaatta caaaaatcac gccgaaaatg gggaaaagaa   11580
ttgaaaaatt gaaggaacac agaacatttt ttcaatgcgt ctctcacgtt cgagactact   11640
gtattcgtgg tgagacccaa ctccctcata aaagcatgcg ccttagtttt tttaatttaa   11700
ttcatgttgc caatattggc caattaattt caagagactc tgattgaaag tgttataatt   11760
aaactacata tatttaagct ttcagcattt ttttcaatgc acttgagacg caaattgaat   11820
aatcaggcac gtaatgtgtt ttcgaggacg actataaatt gtacctttgc tatccagtgg   11880 gttcttaat tttcccattc caatcgattt tttctcccac tctggcagtt tctttgtcat   11940
cactggacga gggcattgga atgggagatg attcatgtga caatccacac atcctgcaat   12000
aatgacatta ttttttaaaa atgttaagat gatatgctta ccaggagtaa atatcatatc   12060
ctttctttta ttagttggct tagccttgcg gccacgttta ccatttgaca ttatagttac   12120
ctgaaaattc aaaaaattag atattcaaaa aggtataaat ataatataaa tgcgatttgg   12180
taaatacgga tgtaatgggc aacccattct atacaggaaa accaaaaaat tcccgcaaaa   12240
ttattttttt ccgaataaaa tgatctactt tgttttatgg tgccgctcta tgtgttatga   12300
cccttcgatt agtagataga aagaaaaag gaatgtacga gaatatcgtt tattatttat   12360
tatttgaaaa atcccagaga cataaaaaat cacacagaaa agggaaacag tatttctgac   12420
aatgttcaaa agtttggttt caatcagcac taataatgtg aaaggtaacc gtatcaatag   12480
tgatattttc ttattaaaaa actgttcgag actacaagaa ggcctgaaaa agcccgcaac   12540
gacgactaaa ttcgaaattt cgaattaggt tttaaagatc agaagatcgg cagaaaagta   12600
tctgataaaa atataagaaa tcggaatagg aatgcgatga ggaggtagaa atatggtgaa   12660
gagatacaga agaatgaggt aagatcggat gaacttgaag cacttttga gattttgat    12720
```

-continued

```
ggtgaagttg gtggatgtag acgtttcatg gaacatctga aaattaagat ttttctaaaa    12780
cacattttct atagaatata atagaatgcc aaatagagaa actagactta cttgaatttc    12840
tttcgatttc tgtctttcaa ccttctaact gaaatcaact ttcgacgtgt tctcggtgtt    12900
tcaacaacac catcaacaga acactcagca ccaaattcag catcggaatc atcagaagaa    12960
gactcatcgg aatccaaata gaaattggat ttagtattca tcaattcaaa agaatccaat    13020
gatactgtcg attcagcaag ttggactgaa cttgatggtt gactacgaac ccattgaggg    13080
cgtcgaggca gaagtcgaga gtatgaggat gcaacgtgga ttgatgatga cgtcaacaat    13140
ctttggtgtt gagatgaaga agtggctgat gcagatgttg acagacggaa tggagatgag    13200
tgaagagcaa aagacatct gaaaatttga acgttgttt atgtggacag tactgtaaag    13260
atcttacctt ggatcataac tacttgccct ctgttttctc ttctcttgac ttctacttaa    13320
aagcatttcc gtctcgattc tccggttact tgaaaatcca actccagaat tttcagcaca    13380
aagctgctct cccgaaccgt agactgttgc accacgttga ggggttgaca aggatctgaa    13440
atcagatgtt taaagcatgg caagtagagc aacaatgtta accaaaattt ctgaaacttt    13500
ttcgaatata gtcaaaaatt gacaataact cagtttcacc tatcatagtt ttggaagtca    13560
accaaaaatt tttgaaattt cataaaaatt ccaaactttc taaaaatttg gaagattgat    13620
atgattgata tgaaagtatt tatatatttt ttaacctggc agacgatact tcaccattaa    13680
agacacacat gtgagaagaa attattttac ttttagtaat ccaacgtttg cacttacctt    13740
ggagcatgca agcttttagt cattaaagct ggaattctag atggagttct tcttggtgtc    13800
gacattgttg aaataaacat tcgtggttca ttgattgatg atgacgtcat agaaccacgc    13860
ccagatgaca atggattacg gtagtcatca gaatcagtag attcattcaa ttttctagtc    13920
atttcttctg ttttctggaa aattaaattt taattaaaga tctaacaaaa atctggcact    13980
tacattaata agataatcaa catattctaa ctcattcatc gtttcattat tttctaattc    14040
tggcttcttc tcatcgaacc gttcggtggc attgtgtcgt tgcgggcttg accgtttttt    14100
gaatttctga aatgttttc atgcaatttt tgttcttatt tgtgtgtcat atacagtgaa    14160
aatcaaaaac tagtacaaac taattccgtt tagtaaataa aaaatcgatg taaaatctca    14220
gcaaagccaa gatcttggcg ggtccttata tccaagtttt gttgccattt tatttcagat    14280
attcttttcg aaagtcagaa aatttgaatt tagaatcgaa tggacccatt tcttgttttt    14340
ttttgttgca ttttttaact gtacttttt cgtcagcata tattttcact attaaaacag    14400
aatattcatg acaataattc cacaaaaaaa cgtactttaa tatcatagtc gattggttca    14460
gaattggaac gagaaccttc gacgcgtcga ttgtcagatt ctcgattgat ggacgacgtg    14520
ctgactgaaa atttctggat tgaaaaaata ttcaaatgaa aaaataaatg agaaactcaa    14580
agtctaaaaa atgaatgttg ttaataacga atatttctga tgagaagagg atagagaaaa    14640
aaaacgagtc taataaaatg catgtgatat cctgcataaa aatcccttct tttttcacta    14700
atccttcgct caattcattc aaatagaact ttgatttcta ttagagttga ggttgtttga    14760
acaattttaa taaattaaca ataagccata aaacctcgaa acgtaccatc atcattgagt    14820
ttgaaaaagt ggacggatcc gagtcagtca cctctggaac aaatcgttcc agagcactga    14880
aaacgacaac gttctcccca cagaatcgga ttgtctcctc gggaattgtc gcctcgacaa    14940
acgatcctga acctgaaaat tttcgatttt tgtaagctca atggatttta aactgaaaat    15000
gtagtcaaga agtcaagaaa aactgatgga gttctaaatt cggtgttagg ttttgaaaag    15060
```

-continued

```
atcgtcaaac aaacaaatgc ataaaactag gtagggaaca aatagtgaaa tagaaaaatg   15120
aaaggcgaca actgccggga gcaagagtac acacaaagaa aaaaagttgc ggaagagcac   15180
agagagcgtc agtccatcag aactgcatag ataaatagat aaagagaaac atgaaacata   15240
aggccacccg ggagagacga caggccagtt ttccggtgaa gatgagagtg cgagaattag   15300
ataagaaaac ggaaattgtg atgaaacttt ttcaatccaa acttctagaa ttataagaga   15360
cacctaaagt aattagataa gtgttttaag tgatatttta gattcactgt atcatgttta   15420 aaaagatat ttcaaaaata tatacctgat ataggaggcc tcctctgagc accgaattgt   15480
tctcgagctg tttccacgag catccgctca cacattgaca taggccgtcg acagccagga   15540
gttgccacct gaataaataa ttattcaatt taaacctaat ttagtaatgg taactttgta   15600
aatgatggtg gatagctcat ataaaatttg aattggttct aaagttatac aaattttaat   15660
ttcggtcaaa cttatgaact gtacttttga gttatactat tacaataata ttacccaaat   15720
tattgtattc agatttttgt aatcagtact aacagatttt aggcaacgtc ctgccagaaa   15780
catgggaata tatttgagca gttttagta agttgccaca gcttgtataa gggaattgta   15840
tcaaaatgta cttaatactt tctaagcact gacatagtga actacaaaag tcggtattat   15900
acaatgccac tacaaataaa aatattcaga attcgactga aaaatgagaa aaggaacaac   15960
tgaattggac acacgatgtc gtgattttca agaacacaaa aaaaagaaaa agaaatcgaa   16020
aatgttgttt gcctcttttt cttttttctat atgagctaga atctcgaatg catgcctaat   16080
ggagccactc gctctcgttt ctctaagtct cttctcacca gtcttttgtc caaaaattgc   16140
gatgtcgcag gcgtcccgtt tccgccgctc acggagacac cactatcggc accagatgat   16200
cgtgtaaaga caccgtcttc gttgacttca attgctgaaa taagaggaat tagttttgaa   16260
ttggaaatct gattaaataa aagtccccta ttcaatctaa ttaattttta aacacaaaac   16320
ttactattgt ttaatggtgt tgacgaatta gaagaagttg attgaaatgc gttaacattc   16380
cattcaaagc tatcttcatt ccattctgct cgttctttta tcctttcact cacgtctcga   16440
gggatgaagt tttcaacaat aagaagcctg aaaacttata ttattctatt aaaaaaaatg   16500
aacatcaaat cctaacgaaa gaaaattctt ctgggggaa aaggagagaa ttgtgagaat   16560
aaagaacctg cgctgtcggt atcaaattac actatttgaa ttcaaattag aatacgaaag   16620
aaagtgaaag aaatgaaaat gagtgagaat ctattaaatt gtaattgaga tatcactgaa   16680
cttacttcaa cttcaattcc ttgctcactt ccgcaattgt ctgatccaga tcttgtcgtt   16740
cgtcggaata tgctccagac acatcacgaa tctcattgcg agcctgaaac attcacaaac   16800
cttatcttga cacctggtac atctgaagtc aaacctgtct caactttatc aacatcttct   16860
ttaacttttt tgtctttgcc tccacctctg tccttaaatc cgaaaatgtt tgtttcaaat   16920
ccacagtatc ctcttcctgc cgttccaatg cttcaaccat ttctctttcc cttcgttttt   16980
gttcggcaag ttctcttctc ttcttttcca gttgtgcatg ttgttctttt gtccttgatt   17040
ctaaccttcc atcttcttca gatcctacga taagtcgact ttgaatgttt gctattcttt   17100
cagcaacccg tgcttgttct atccgttcct tttctaacag atcatgcttc tcttgaattt   17160
ctcttattaa tcgatccttt tcatgtttta tcagtgaatc atcttttttga attgcttcaa   17220 tatcatcttc aagttttgct cgttcagcat cataaaaact ttgagttgct ccatccctcg   17280
atcttgtctt tctctgcttc agttgctcac ggagcatttc aatttcttct tggaattctc   17340
gcagtaaagc atccttagga tcttcattaa ttttcggttg attcttgatg ttttttagctc   17400 gatttgcata tcgtaatgta ccaagtgtct cctcaaaatt gtaacttgca ggtccaatac   17460
```

```
aagcaaccat aactgtcttt gaatttccac cgagagaatc ttgaagaagt cgagtcagtt    17520
ttgaatctcg ataaggaata tgggcagatt tcgcatccac caatgcactg attacatttc    17580
caagagccga taatgaaaga ttgattttcg tagcttcttt aaatctttcg ccagttgctc    17640
ctgttttcga ttgccgttct gaaccagcta aatctacaag atttagtcga ccaactgtaa    17700
tatgactttc tccgtcttca ccaattcggg aacattcaac agtaatgata aagatagcgt    17760
gggaacgaga cgaatgctca ttcatgttgg ttcgcctgaa aattttagta aaatcaaatc    17820
caacggcgac cacagaaata acttaccccta cagaccgatg cccatttcct cgaatcatca    17880
cttcgtgtat ttcacctact gtccttgtta attttgactg aaactttgaa atttatagtc    17940
gtcttctatt tcagaaaact atcacttacc gttaaatctt tcacataaac tcctccatct    18000
ggacgttctt taatttctaa tttcttattc gattcggctt ctaataaatc tcgaagttcc    18060
tcctaaagat ttcattttg taaatcacac atcctaacgc cttacctgat aaatttccaa    18120
atagctagct ctaactaaat actcttgatt atgtgatgct gccatgtgct caaaaatatg    18180
gtcaatacac ttatagatga caccctcgttg ttctggatcc gatgattttc cttccattgt    18240
gtgagtcttt ccagttccag tttgaccata tgcaaaaatc gtggcattat atccgtttag    18300
aaccgaatca actagatctc gaaaggtttc ttcatataga tccgattgtg tggaactata    18360
aaatatatat ttttaaaaaa gagaactcat aaaatcataa acataaaatt gtggagaaat    18420
aattttgaaa aatactaata tttctatagc aggtgaaaaa aaagtgatgt actcctagaa    18480
ataaataatc ttacttttca tcataaattg catcgaatgt aaaatccttc gatggctcat    18540
cttgctcttt tggatttttc agctcaattt gcccacgttg tggtcgcata tgtactattc    18600
tgaaaatgat cgaaatttca aaatataaat atttcaaact ttacttactt tgaataatta    18660
tttgcaattt cttgtgaaga taacggtcga catctcacaa ttacctgtaa acataaataa    18720
atacatttat ttgaatttgg aaatgtataa aactggatta tgaaattttt aagctggtgg    18780
tttttgtatg agaagtaacg aaaaaaagta caatttactt agagtcttgt gattttctt     18840 tcaaatgcaa aactcaactg aatcataaat agtgatgctt cgaaaagttt ttagaggaaa    18900
attgtatttt tagtaaaaac taatatacgt tttggactta aaaaaaaatt atgttaaaac    18960
ttgaaaaatt acgtttatta gtgcttatat taaaatacgg tttcaaatta atttaaaatt    19020
aaaataactc acctttggt caaaatcaga cattttagaa actagcatgt actttattac     19080
gttgaatata acttatgttg gaaatggaa aatttgaaga caggtgaatt ttagttttttt    19140 ttctttttcg tacttctaaa aaatacttca tttattttac attttgagaa ctaatttttg    19200
aacatgtttc gaacaaaaa aaagattttg aaaacccccaa aaaaacttac tttgacagtc    19260
tcctgttttg aagattttt cattatttcc accatttttt gtcactaaat atttggctat     19320
caatgtaggt gtcaaggaaa attttggtgc attcctgatt tagtgagagt ggtctggaac    19380
ttaagaagat tagtttaatg tggaaaaata atcatattgt atcgagaaac ggaattttga    19440
agcaataacc gctagagaaa gtgactaaaa accagaaatt gtagtcgtgg aatttcaata    19500
tttttggttt tatgtcacat ctggacaatc ggaaaaatat gcatacattt gaatttttta    19560
gaaatatttt gaattaactt taaggaaaa aaatgcatta aaaagattga aaacatcatt     19620
gacgttgaaa aatggagaaa atttctaatt tctcatcaaa atattaaaat attaaagttc    19680
ttcaataata tgaaatgtg aataaaatgt ctaaataagc aaaaaaaaca gatcctattc     19740
attataaaat gttcacacaa gtgttacatt tcgtacaaag aagtactaaa acggatggac    19800
```

```
taaagtaata ttgtcactcc cgaaaagacg aggaagaagt aatcggaaga agatgtcgga    19860
agatgagtga tagtaaaaat acgaagagac gcagatagag agtttgagag aaggagactt    19920
ctggaggaat aaaaggtggt ttcaagatgg gggacagaga gggagagggt taaaagagca    19980
caaaatgtgc ataatatcga tcctgcgcag ttgagagacg cagacaatgt gaagaatgga    20040
gcatatgttt ctagtgaaca ctcagaagta gttgttcatg tgtccgaaac tttgaaaaca    20100 tatacattt aaacttgacg tttttgaatt ataaagggat ggaggtgctt caaaaagtaa     20160
tcatagacat gtgtagattt taaattaaaa cacaactaga cataggatga atcagaagct    20220
taccataaca ttgttgattt atttaaaaat gagaaaaagt aaaattccgg atagtcttct    20280
ttgaaaaaat tcacagagaa gttataatgt ttgatgatat tcactgattt gtaatacatt    20340
attagtagca tggcttctat gtatatagac tattttata tcacatacat gaaaaagggt     20400
taaggcatgc gccagggcct gaaaacgcat ctacctacca ggggagctct agctcttagt    20460
tattaattca agagactttt gaaacttgat tttttgagat tttattcaat gattggttta    20520
aaaaaaaaga ttatttgcaa aaattacaaa ttttaatgtc tatactctga catcggttta    20580
gaacaatttt agacaggctg caatgaaagc aatgaaataa aatttccttg aaattataat    20640
agagaatcag taaaatgttg cagattattt gaaaatgcat gcaagaattc gcagaaaatt    20700
cagtgaagca gaaaagtgcg acaggagacc gaagtctaaa aaagtgaatt atgaataaaa    20760
acaaatcatg tgactggata taattgaagg tcttgattcg gaaagataaa ttggagctct    20820
ttgcttaggc caggctctag atattttatt gaagcttttc agaaatgttc aaaattatca    20880
ggaacagttc tctttgcact ttctctatgg ctcaactacc agggcttttc cttttcttc     20940 aaaagtaga attttaaatt ataatttta aattaaata ccaagcaaaa aatcatatac      21000
tcatcatatc atgtgatcat atcatataat catatagggc tcgttctttt tttttcaaa    21060 aaattaaaaa tttactagaa ccaagcatat gacaataaaa tattttgaat tcactttaat   21120
gggaaaaaaa caagaaaatt tcattaacat tattgaaaac atcgttggca ataggaatgt    21180
agaaaatcaa atcaaaatca agtgagatta ggaaagaatc gaaattaggt agaattggaa    21240
aatctcgatt ttttaagttg gattcttaca cgattttttc gggatatttt tcattttttat   21300 tttgtagtat ttcagcctag acggctgaga attcttttca aaccttccaa tttcaaagag    21360
attcttccat aatttaatat aattttcatt cgatattagc atccattata tacgtatgat    21420
tcccctttta aaatcgattc tcctttttcaa ctgactcatc acttaagaat tgttgagtca   21480
tcaactgata gtgagcagac accaacaacc atctctttag tttccgttcc gtttatttta   21540
ttttggaatc taacatattc aagaaaatta acttgaaatt agaataaatg tttcttgcta    21600
gatttttttg tcataagtat ttcttatttg gattataatt ttcatctcga aatcgtagag   21660 agttttcac tatttttttt tgagttctaa acacttcctt cctcatcgat gatgaagttt     21720
ttgacaaatc aactagtttt ttactcatat ctcacatcaa tctatgattt tattcaaaaa    21780
cagttaaatt ttttaacga aattaaaatg gtcatcggac cgagcaaaag ctttcagaat    21840
caactgcttc tttaaattct ttaaaattca atcaacttttc cgtgtccaaa gtcacaaact   21900
acacctttca aaaatattt ctacattatt tgcccacatc ttggcacagt tttcttgcca    21960
ttcttcaata tttctcttctc tgcgtttccc acactcttat tttctgactg ttgacttttc   22020
cattgtatag actcaatttt actttcgttt tttcaattt tttttctgcg aagttcggtg    22080 ttaacctcc attttgcaat attaaaaatt tcaatattgc ccgttttggc ttgaatctat    22140
taaaattatg ctgtttttt ttcagaaagc accaaaacat gccagatgat attccaaaat    22200
```

```
tgccacgaca cagaggaaag aaaaatcagc cgaaaggttt gaaaaattta gaaaaatctg   22260
aagttacttt tttaattctt tagacacacc ttggaaacaa caaaaactgc ctgctttacg   22320
gcctcattat aacataactt cagcaattcc agttactctg ataacaggag tagccacgtt   22380
ggcaatggga attgctcttt atttcggaca taatggatgt gagttttag agtttattat   22440 cccaaaaaca aaaatatcaa ttactctttc ctggtaataa gtaagaaaaa gctaaagaaa   22500
acaaatttct tgtcaaaatt ttacattgta aaccgatagc aacaaaaaac aagtgtcata   22560
aaaactgtaa gaaaatcgat aattttgcta caatttcaca aagctaaaaa atatttttta   22620
ttttaccgtg ttagtaccgg aatgttctgc acttgagcct tactattagt tacacaaaat   22680
ggatcaattt tgagcaattt gttgtgaatc tgacaataat tagtcctatt gatatagctt   22740
taggccactc attcgtgttc gtaattttcg ttttccttga acttgtaaag gtacagtttt   22800
tgaaaacagg gatgtagtcc aagtagtcaa atattgattc ttgtagcatt agaacaagag   22860
attgtgtaca cggattgtgc tctttcaaat ggaacacaag cttcacgaat tatgagaact   22920
gaaatgggaa atcaaacatt taaatgtgca tatacaatta ctttgaatga cgattatact   22980
gtaagttgag ttttaatttt taaatcatca aagaaaacat atgtatattt ttgcgaagga   23040
aattttggat ctggtcttag gatgaaacga cattgtaaca ttttgattaa agagcccta   23100 gttggaagtg agtgtatctg gtaaaaacac aattcgaaaa tatttaacca aatatgtata   23160
aagcctaggt tgaacctgct ctgcagttcc taattttttca cattatttt cttcaaaata   23220 ttactatgat atttcaaagc ccggggtacc atcttaaaat catcatttgc aagtatcaca   23280
attaatgttc aacattacag ggcgaagtga agttttatta cggtctttcc aagttctatc   23340
aaaacaatcg attatacttc aactcacgaa acgatcaaca gctacgtgga aaagttactg   23400
aaactgacgg atgtgatcca ttagaatatg tggatgttaa tggaactaaa gttcccattg   23460
cgccgtgtgg gaaagtggct gattcaatgt ttaacggtgc atttcaattg attgcttaat   23520
ttcagtattg caacattttt catttttat aatacatcta acttcaaaat ttgttttttt   23580
ttcagatacc ttcgaattat tttatatcaa tgataaagcc tcaaacgcgg taacacgggt   23640
tccatggaca actcgtggag tactcggtgc aactgaaatg aaaagaaaat tcagaaatcc   23700
gattcgagcg gaaaaccaga cattatgtga tgtgtttgcg gttgaaatga ataagaaaa   23760 aaaataaatt aaactccatc ttttagggaa caatgcctcc gccatcatgg agatatccga   23820
tctgtcaatt gggactaaac agtattgatc cagatgttgg cattggtttc gagaacattg   23880
attttatggt ttggatgaag gttgcagctc ttccaaaatt cagaaaactg tatagaatac   23940
tgaatcgaca agttgatatg ttcagtaatg gattacctaa aggacaatat cagttgacca   24000
ttaattacag tatgtttatg ttaatgttga atttatgtat ttatgcaaaa aatttactgc   24060
aaaagttcac aataattcca cccaaacctg cttaaatatg gagatgcaag ttttttgttt   24120
cagataaaca gtggctccaa aaaaccaatc tttgttataa aacctcacaa aaatttctcg   24180
atatttcttt attatggttc aaactttga gaaaaaggg aaatttagaa aattctttca   24240
agcgaaattg tcaaaatttt tcaaaaccaa atttgatttt ccagatttat ttttttgtcga   24300 cttgacaata gtaaagaaaa aacaagttga atttttctat atgaattctt atagctgaac   24360 attttttgatc aatttgaaaa taatcaatag acaattttc tccatactac tgattttcag   24420
actatccagt ggatatgtat tcgggcgaca agtacttcgt tatagccaat gaaaactggg   24480
ttggacccag gaatctgttt ctaccagtaa tctatttggt tgttggaaca ttcttacttc   24540
```

-continued

```
tcgttactat tctcttcata ttgatttggt taaaacagag actgtcgagg gttcatccaa    24600
catgaattgg aaaaactaat tgaaaataga cggatgaact tcaaatttgt ttacaagagt    24660
tgaagtctca aaataagctg gtagcatgta ttgtacggga acagatttgt atactttgct    24720
ttgtaaataa aataaaatgt tattatatta gtctgtaatt ttatgtatag ttcaatttaa    24780
ttgaaataca taatacccccc ttcagtttat caattaaagc tccaactatc attcgctggt    24840
tgagattaat tgtcgagtga gggcatctga aatgtaaatt taaaattaca aaataaataa    24900
ttgtaagtgc tatcagatat aacaaatgat catttaatta aggaggaaaa acaaaacatt    24960
aatttaaaaa atttatcaaa aaacaaaaaa aaacggtcaa atattttttc aaacaaacaa    25020
agtaaagcta atttctatta aagttgatct aaatactggt tgtgtaggca tactatagtt    25080
gatttcaacg ggaagaaggc caaatcagca agtgtacatt gtgttctgaa aaattgaaat    25140
tcaacagttg aatataagta gaaactctac ctattgctaa catttattgc aattcttctg    25200
tgttttgaac aatatcgaga tcgctccatc catcggataa ttccgtatga tttgatgaca    25260
tctcatctac agcttccaat tctccaatta tctgatcctt cagtttcagc ttaatatcaa    25320 acgattttg aatttcctgg atatttgctt cataaactct cgagatttca gatttaactt    25380
gttgaatctc tttaaattgc tctgaaatct tcttctcaag aactcttttc tgataatata    25440
gctcagtgat ttctcgagtt cttttctttca taatcatttc agtattcatt tgttcttctt    25500
taacattttc ttcaagtttt tcaatctttc gtacataatc acagaaatga tcaaccacct    25560
gcaaccattg cgggtcattt cgcatagttt tgagtcctcc gggttgttca agaattgcga    25620
caagactttc tgtctgttca agtttcagtt tttctaatgt ttgctcaagt gggaattctc    25680
tgacctcctg gtttgcctct tcggaaggat cagaaatttt ttcagaatgg aacgtcaaaa    25740
tttcttgttc caaatgggga tatgttctac tagtcccttg actagaagtc tcactagaga    25800
ttttaagtgt cagttctcga acattacgct ccaatttcgg agaatttcca gattcagtgc    25860
tcacatgact ctttaatttg acaatctcat cattcttatc aaagatttga ttttccagtg    25920
cagagacctt cacttgacaa tcttttgtct tccatgacaa ttcatctgcc aacatcttga    25980
tcatgttctc attcgaatca atcgtttttt tcatatctttt tatcatgtct tcatcagttt    26040
tgattgtaac attttgcttt gaaatttcac gtttcacaga attcaaagca attttcaaag    26100
aattgttgaa attttcgagc atcaaacttt caacaccttc ggatttatca ttcttggcaa    26160
cattccgatc attatttagt tcagttgata tagaattggt atcatcaact gagaatactg    26220
ttaaattctg gtgttgaagt tccaaaaatt tctccatgac tttttcaata ctatccttct    26280
gataaacatt gaaggattct tgaagcattt taatctcttc attcttttttc ttgagttcgg    26340 aaaacagaat attctttctt ttttggaatt ccactgtcac taagagataa tcatctttgt    26400
tttccaaaga tgtaaccagc tgcgatggat tcaaactttc caagttttc gtaagatagt    26460 caacttcgtc ttcaagtttt tgaatgatct gtttgttgtc ttccatcttt tttgttataa    26520
gtataggatc cttgaaataa agagaaaacg tgactatgat cttgtcaata gtttccagca    26580
agtggaaaat gtcataataa tctccatcat ttaatacttt taatttgtcc aaaagttgat    26640
ccatcaactt ctcttgtttc ggtgtttcat caccaattaa tattccaccg taaccgttaa    26700
ccggatatgg cgacaaatca taaaattgtt tttgaagatc tcatatttta gttttgagaa    26760
ttgagaaatc ttcatttctc attatcaaca acttcttcaa tcttctagct tctgtctctg    26820
cttttatttg gaaatttcg aattgcattt cagctagtat tatctcatct tcttgttcat    26880
cgattaattt ctcaacttct tctttttaatt ttttgatatt ttgatctttt tctgccatag    26940
```

```
cattttgaaa atcttctagt gttgcaaact gatattcagt ggatgtactc gtggattctt  27000
gagtcgaaat ttcagtgttc ttgtttattc gttttacttc ggagcttctg actattttct  27060
ctggagtcca aaacttgtct acttccaaaa aatgtgtttt tttgcttctg aaaaacatat  27120
attaagtaac atctttaaga tattcaggtg cacttacatt tttgaaatat ttggtgacaa  27180
actttgaatt atcaatctga attcttctgc ggttccagtg aagcaagcat aattctgaaa  27240
ataaaaatta cagcttttga aaccaatgaa acgaaacaac tattgtattt aaaaaatgct  27300
cacttcaact ccattctctt ccaccgctgc ttcttttttc acacttttcc agtttatcaa  27360
ttaaaaattc aagtttctgt tgttcaggtg aaggctgaga tgctgtgaac gacatagttc  27420
tgaaaatagt taatttaaat gtagcagaaa atcttttct agaaagtaaa aaaaatcagt  27480
aaaaacaagt actaagagaa attgaataaa ccaatcacaa taatgacttc ttaacaagct  27540
gaaaaataat gcaatagcaa agaaaaacga gtagtttcgg taactccata gtacattatt  27600
tcgttattgg gatcatcata tcatttattg atgaggatat tatgagttaa ttctaataac  27660
ccgagagtaa aggcaaaaaa tagcatggag tgaaaaaacg gatcaagcaa agaaatcgtg  27720
ttaacttta taacatctag ttgacactgt cagaccaaaa acttaataaa attttcactt  27780
gtacataaca gctagctgaa actgtaattt aattttatat tccctcggtc aattctagct  27840
aaattagcga ttctgagcta agccttcatt tcaaaattaa caaaaaaaat gcaatgaaat  27900
tttcacttgt acataacagc tagctgaaac tgtaatttaa ttttatattc tctcggtcaa  27960
ttctagctaa attagcgatt ctgagctaag acttcatttc aaaaataaca aaaaaatga  28020
attgaaattt tcacttgtac ataacagcta gctgaaactg caatttaatt ttatattcct  28080
tcagtcaatt tcagctaaat tagcaatttt gagctaagtg ttgttgtttc ttaaaacaat  28140
gcaaattttg atggtttttc gtgttcagtg aacaaacaaa caaacaaaaa aattctggta  28200
aataaccaca agctgaaact gtgagataat ttttttagtga ccattgagtg actgctcata  28260
gacagtggct tggaattaag actagaatga ttatctctca tgataacata ttatacagag  28320
aagttgggaa gaatgtaggt cattgtaaag cgacagacag gtcgcattga tcaaagagaa  28380
tataagtcga actctttcgt ttggtaactt gagggccaat gttatttgct attagggaaa  28440
attaacattt aaggagcaaa ggattgcaaa caaaatgcga taagatatat gattatagta  28500
ttttatcttt tgtaagtgtt gccataattt cagtaacgaa aaaaataaca aggcaatttt  28560
agatgttagg aaaatcgaat ttgtctgact agccaacgaa tgttctcaat tgaagttatt  28620
gttcttttt aagatgtttt catacaaatt agtcagtttt cgaagcttca gccacactta  28680
tccgaattga gcaatttcaa aactattttt tgtaaaataa aatacatctc cgaaaattta  28740
catcgagttc ccaacaatac tgtatggata gaaaatacct accaatactg cacatgaaac  28800
gctctgaaaa taatcggaaa ggaaatgaga acctttaaa tataaaatga gcacaataag  28860
taatactaac tttattgaga aagaacataa ttgttatgag aatagttttt aaatgaggtg  28920
agaaacagaa tatccctgag aataagtgaa gatacttgaa aatttgtgaa atagtaataa  28980
gtaaatgtt ttcacattag tataaacaat gacagagtca cgcaaaagta cgggaaacat  29040
atgaagttta taatacagtg cagtacagaa aaggtacaaa gtttacaaga atacaattgt  29100
tttttaaaaa taatttttg ttgaaggctt aaggtaatac gattaaagag ctactttctt  29160
ccaatacgaa gttgaatta aaatttaaa ggaaaaagg aaaaaaatta aaaagcatat  29220
gaaaaatcgg ggcgcatttt tagtgcaaaa aattagatgg catttatttt atcccatcca  29280
```

```
tctgaatctt cactgtgtgt ggatttattg tcgtcatctt gatcgatcat tgtatcatca  29340
gcttctcctt cttgattgat aagaagacct tgcagttttt ccgaaagttc cgaaatcttc  29400
aaatccttct ctctcaatgc atcatgcatc ttctgaattt cagcggatcg ttcgctattt  29460
tgaataagtt ccatcagaca ctcaattttg ctatctttt ccatgatttc tcttttatga   29520
tttgcaatct gttcttcttt tgattcacat tctctctttg aattggctga aataaaagaa  29580
aatgcttaca gatgtgtgta aaacccctag aaaactttca caagcttacc tgtcaatact  29640
tcaaattgcc ccaataagtt gtgcttccac tcttcagttc gaagtttaag atcttcaact  29700
gatgtattaa gcgtggcttt ttcctgctga gtgtttgcaa gttgcatctc taacgccatg  29760
acggtcgagt tatgttgatc caaaatatga ctg                               29793
```

GENES ENCODING SEVERAL POLY (ADP-RIBOSE) GLYCOHYDROLASE (PARG) ENZYMES, THE PROTEINS AND FRAGMENTS THEREOF, AND ANTIBODIES IMMUNOREACTIVE THEREWITH

CROSS REFERENCE TO RELATED APPLICATION

This Application claims the benefits of US Provisional Application No. 60/083,768, filed May 1, 1998. The entire disclose of U.S. Provisional Application 60/083,768 is incorporated herein by reference.

STATEMENT REGARDING FEDERALLY SPONSORED RESEARCH OR DEVELOPMENT

The present invention was supported in part by the National Institutes of Health (Grant CA43894). The United States Government may have certain rights in the invention.

TECHNICAL FIELD

The present invention relates to poly(ADP-ribose) glycohydrolases (PARGs) and peptides having poly(ADP-ribose) glycohydrolase activity. In addition, the invention also relates to antibodies, including monoclonal antibodies and antibody fragments, that have specific interaction with epitopes present on poly(ADP-ribose) glycohydrolases. Methods of treatment and diagnosis using the poly(ADP-ribose) glycohydrolases, and antibodies specific for poly (ADP-ribose) glycohydrolases are disclosed. The present invention has implications for the treatment of neoplastic disorder, reperfusion following ischemia, neurological disorders, and related conditions.

BACKGROUND OF THE INVENTION

Genomic damage, if left unrepaired, can lead to malignant transformation, or cell death by senescence (aging), necrosis or apoptosis. Among the variables that can affect the ultimate biological consequence of DNA damage to a particular cell are (i) the amount, type, and location of the DNA damage and (ii) the efficiency and bioavailability of the cellular DNA repair mechanism.

The activation of poly(ADP-ribose) polymerase (PARP) by DNA strand breaks is often one of the first cellular responses to DNA damage. PARP catalyzes the conversion of nicotinamide adenine dinucleotide (NAD) to multi-branched polymers containing up to 200 ADP-ribose residues. Increases in polymer levels of more than 100-fold may occur within minutes of DNA damage. Once synthesized, polymers are rapidly turned over, being converted to free ADP-ribose by the action of poly(ADP-ribose) glycohydrolase (PARG) (1). An ADP-ribosyl protein lyase has been proposed to catalyze removal of protein-proximal ADP-ribose monomers (2). FIG. 1 illustrates these processes schematically.

The process of activating PARP upon DNA damage can rapidly lead to energy depletion because each ADP-ribose unit transferred by PARP consumes one molecule of NAD, which in turn, requires six molecules of ATP to regenerate NAD. Additionally, NAD is a key carrier of electrons needed to generate ATP via electron transport and oxidative phosphorylation or by glycolysis. The overactivation of PARP due to substantial DNA damage can significantly deplete the cellular pools of NAD and ATP (3). ADP-ribose polymer metabolism, and thus PARP and PARG have been linked to the enhancement of DNA repair (4), limitation of malignant transformation (5), enhancement of necrotic cell death (6), and involvement in programmed cell death (7). To date, studies of the structure and function of the enzymes of ADP-ribose polymer metabolism have been mainly limited to PARP (8). Little is known about the function and regulation of PARG.

BRIEF SUMMARY OF THE INVENTION

As embodied and broadly described herein, the present invention is directed to nucleic acids molecules, peptides, methods, vectors and antibodies that are related to the poly(ADP-ribose) glycohydrolase (PARG) enzyme.

One embodiment of the invention is directed to an isolated and purified nucleic acid molecule or nucleic acid molecule analog comprising a sequence that encodes a polypeptide having poly(ADP-ribose) glycohydrolase (PARG) activity. The nucleic acid molecule may encode the complete full-length PARG gene or a fragment of the PARG gene. The nucleic acid molecule may be DNA, RNA or peptide nucleic acid (PNA). The nucleic acid molecule can be linear, such as, for example, an isolated fragment or a linear phage DNA. In addition, the isolated nucleic acid molecule may be circular, such as for example in a plasmid. The nucleic acid molecule may also be a single stranded DNA or RNA such as the single stranded DNA or RNA in a single stranded DNA virus or single stranded RNA virus. The nucleic acid molecule may be of yeast, insect or mammalian origin.

The nucleic acid molecule of the invention, may be of mammalian origin, such as, for example of bovine or murine origin. In a preferred embodiment of the invention, the nucleic acid molecule may be of human origin. While the sequence of the nucleic acid molecule is of mammalian origin, the nucleic acid molecule may be replicated in another organism such as an insert in a viral genome, a plasmid in a bacterium or a 2-micron plasmid in a yeast.

Preferably, the nucleic acid molecule has, a high degree of sequence similarity with a sequence shown in SEQ ID NO: 1 (Genbank Accession Number U78975), SEQ ID NO: 3 (Genbank Accession Number AF005043), SEQ ID NO: 5 (Genbank Accession Number AF079557), SEQ ID NO: 7 (Genbank Accession Number AF079556) or SEQ ID NO: 9 (Genbank Accession Number CEF20C5). The high degree of sequence similarity may be, for example, about 70%, preferably about 80%, even more preferably about 90% and most preferably substantially identical such as for example about 100% identity.

The nucleic acid molecule that encodes a polypeptide having poly(ADP-ribose) glycohydrolase (PARG) activity may be single or double stranded nucleic acid molecule of any length such as, for example, about 20 bases in length, about 30 bases in length, about 40 bases in length, about 50 bases in length, about 100 bases in length, about 200 bases in length, about 500 bases in length, about 1000 bases in length, about 1500 bases in length, about 2000 bases in length, about 3000 bases in length. It is understood that "bases" in this patent application means "basepairs" when referring to double stranded nucleic acid molecules and bases when referring to single stranded nucleic acid molecules. In a preferred embodiment of the invention, the nucleic acid molecule may be at least about 1000 base or basepairs long and have at least about 80% sequence similarity with a sequence shown in SEQ ID NO: 1, SEQ ID NO: 3, SEQ ID NO: 5, SEQ ID NO: 7 or SEQ ID NO: 9.

In one embodiment of the invention, the nucleic acid molecule may have sequence similarity to one region of the PARG sequence. The region may be, for example, from about base residue 2113 to about residue 3105 of SEQ ID NO: 3. Alternatively, the region may be, from residue 1240 to about residue 3105 of SEQ ID NO: 3 or from residue 175 to about residue 3105 of SEQ ID NO: 3.

Another embodiment of the invention is directed to the expression and overexpression of PARG in a cell. Expression vectors may mediate the expression of a polypeptide with poly (ADP-ribose) glycohydrolase (PARG) enzyme activity. Expression systems and expression vectors are known in the art. For example, one expression vector may comprise a regulatory sequence which is operatively linked to a nucleotide sequence at least about 1000 base pairs in length, which has at least 70% sequence similarity with a sequence shown in SEQ ID NO: 1, SEQ ID NO: 3, SEQ ID NO: 5, SEQ ID NO: 7 or SEQ ID NO: 9. In a preferred embodiment, the sequence similarity is at least about 80% identity, more preferably at least about 90% identity and most preferably about 100% identity. The expression vector may be any expression vector that is capable of directing expression of a gene in a host cell including, prokaryotic, eukaryotic, mammalian and viral vector. Examples of such vectors include pCMV-Script cytomeglovirus expression vectors for expression in mammalian cells, pESP and pESC vectors for expression in *S. pombe* and *S. cerevesiae*, pET vectors for expression in bacteria, pSPUTK vectors for high-level transient expression, and pPbac and pMbac vectors for expression in fall army worm (SF9) cells. Such vectors are available commercially from suppliers such as, for example, Invitrogen (Carlsbad, Calif.) or Stratagene (La Jolla, Calif.). In the use of viral vectors, it is understood that defective viral vectors—vectors that are genetically engineered to deliver a gene or gene product to a host but which cannot replicate in a host is preferred. Procedures for the practice of in vitro and in vivo expression are well known to those of skill in the art and are further available with the specific expression products and cell lines from commercial suppliers.

Another embodiment of the invention is directed to a host cell transformed with a vector containing a nucleic acid molecule with a sequence that encodes a polypeptide having poly(ADP-ribose) glycohydrolase (PARG) activity. The host cell may be any eukaryotic or prokaryotic cell such as, for example a human, murine, rattus, bovine, insect, yeast or bacteria. Specific cell lines are well known to those of skill in the art and are available from suppliers such as the American Tissue Type Collection (ATCC, Manassas, Va.) and Stratagene (La Jolla, Calif.) and the like. A preferred embodiment of the invention is directed to cells transformed with the PARG expression vector which shows an elevated level of PARG relative to non-transformed cells. Especially preferred are cells transformed with an inducible PARG expression vector that have normal or slightly elevated PARG levels before induction and have significantly elevated PARG levels after induction.

An embodiment of the invention is directed to an isolated protein having poly(ADP-ribose) glycohydrolase (PARG) activity. The protein may comprise an amino acid sequence with at least 70% sequence similarity with a sequence shown in SEQ ID NO: 2 (Genbank Accession Number U78975), SEQ ID NO: 4 (Genbank Accession Number AF005043), SEQ ID NO: 6 (Genbank Accession Number AF079557), SEQ ID NO: 8 (Genbank Accession Number AF079556), or SEQ ID NO: 10 (Genbank Accession Number CEF20C5). The sequence similarity is preferably at least about 80%, more preferably at least about 90% and most preferably substantially identical with a sequence shown in SEQ ID NO: 2, SEQ ID NO: 4, SEQ ID NO: 6, SEQ ID NO: 8, or SEQ ID NO: 10. In a preferred embodiment of the invention, the preferred isolated protein having poly(ADP-ribose) glycohydrolase (PARG) activity and has a molecular weight greater than about 100 kDa.

Another embodiment of the invention is directed to an oligonucleotide which is greater than about 10 bases in length and less than about 1000 bases in length which is complementary to a sequence shown SEQ ID NO: 1, SEQ ID NO: 3, SEQ ID NO: 5, SEQ ID NO: 7, or SEQ ID NO: 9. The oligonucleotide may be, for example, greater than about 20 bases in length, greater than about 30 bases in length, greater than about 40 bases in length, greater than about 50 bases in length, greater than about 100 bases in length, greater than about 200 bases in length or greater than about 300 bases in length. The oligonucleotide, which may be optionally labeled with a detectable marker, may be DNA, RNA or PNA. A detectable marker may be, for example, a radioactive isotope such as $^{32}p$ or $^{125}I$, an epitope such as FLAG.

One preferred oligonucleotide is an antisense oligonucleotide directed to the mRNA of PARG. Antisense oligonucleotide as a method of suppression is well known to those in the art. For example, the phosphorothioate oligonucleotide, ISIS 2922, has been shown to be effective against cytomegloviris retinitis in AIDS patients (9). It is thus well known that oligonucleotides, when administered to animals and humans, can have a useful therapeutic effect. In a preferred embodiment, the oligonucleotide is at least about 10 nucleotides in length, such as, greater than about 20 bases in length, greater than about 30 bases in length, greater than about 40 bases in length, greater than about 50 bases in length, greater than about 100 bases in length, greater than about 200 bases in length or greater than about 300 bases in length. In another preferred embodiment, the oligonucleotide has a ribozyme activity.

Another embodiment of the invention is directed to an isolated polypeptide of at least 6 amino acid residues in length and having a molecular weight less than about 65 kDa, which has at least about 80% sequence similarity with a sequence shown in any one of SEQ ID NO: 2, SEQ ID NO: 4, SEQ ID NO: 6, SEQ ID NO: 8 or SEQ ID NO: 10. The polypeptide may be, for example, at least about 10 amino acids in length, at least about 20 amino acids in length, at least about 30 amino acids in length, at least about 40 amino acids in length, at least about 50 amino acids in length, at least about 75 amino acids in length, at least about 100 amino acids in length, at least about 150 amino acids in length, at least about 250 amino acids in length or at least about 500 amino acids in length or more.

In a preferred embodiment, the polypeptide has a molecular weight less than about 40 kDa and has at least about 90% sequence similarity with a sequence shown in any one of SEQ ID NO: 2, SEQ ID NO: 4, SEQ ID NO: 6, SEQ ID NO: 8 or SEQ ID NO: 10. The polypeptide preferably has poly(ADP-ribose) glycohydrolase (PARG) activity or is immunogenic and elicits antibodies immunoreactive with a poly(ADP-ribose) glycohydrolase (PARG) enzyme. In a more preferred embodiment, the polypeptide comprises an amino acid sequence substantially identical with SEQ ID NO: 4 from about residue 647 to about residue 977.

Another embodiment of the invention is directed to an isolated polypeptide of at least 10 amino acid residues in length and which has at least about 80% sequence similarity with a sequence shown in any one of SEQ ID NO: 2, SEQ ID NO: 4, SEQ ID NO: 6, SEQ ID NO: 8 or SEQ ID NO:

10. Preferably, the polypeptide is at least about 20 amino acids in length, such as, for example at least about 30 amino acids, about 40 amino acids, about 50 amino acids, about 100 amino acids, about 200 amino acids and about 500 amino acids in length.

Another embodiment of the invention is directed to an antibody immunoreactive with an isolated polypeptide of at least about 6 amino acid residues in length and having a molecular weight less than about 65 kDa, which has at least about 80% sequence similarity with a sequence shown in any one of SEQ ID NO: 2, SEQ ID NO: 4, SEQ ID NO: 6, SEQ ID NO: 8 or SEQ ID NO: 10. In a preferred embodiment, antibody is immunoreactive with a polypeptide with a molecular weight less than about 40 kDa and has at least about 90% sequence similarity with a sequence shown in any one of SEQ ID NO: 2, SEQ ID NO: 4, SEQ ID NO: 6, SEQ ID NO: 8 or SEQ ID NO: 10. In another preferred embodiment, the antibody is immunoreactive with a polypeptide comprising an amino acid sequence substantially identical with SEQ ID NO: 4 from about residue 647 to about residue 977.

Another embodiment of the invention is directed to a method of detecting a polypeptide having PARG activity comprising the steps of contacting the polypeptide with an antibody immunoreactive with an isolated polypeptide of at least about 6 amino acid residues in length and having a molecular weight less than about 65 kDa, which has at least about 80% sequence similarity with a sequence shown in any one of SEQ ID NO: 2, SEQ ID NO: 4, SEQ ID NO: 6, SEQ ID NO: 8 or SEQ ID NO: 10, and determining whether the antibody immunoreacts with the polypeptide.

Another embodiment of the invention is directed to a method of preventing, treating, or ameliorating a disease condition or disorder in an individual comprising the step of administering a therapeutically effective amount of a poly (ADP-ribose) glycohydrolase (PARG) inhibitor or activator to the individual. The disease condition or disorder may be any condition associated with responses to DNA damage, examples of which include a neoplastic disorder, a myocardial infarction, a vascular stroke or a neurodegenerative disorder. The PARG inhibitor or activator may be a small molecule inhibitor or activator of PARG or may be an antisense oligonucleotide that can hybridize in vivo to messenger RNA encoded by a PARG gene. PARG based treatment may be directed to new methods for preventing, treating or ameliorating disorders associated with DNA damage. These disorders include neoplastic disorders, inborn genetic errors, myocardial infarctions, vascular strokes, aging, and neurodegenerative disorders such as Alzheimer's disease, Huntington's disease, Parkinson's disease, and neurotoxicity generally.

Another embodiment of the invention is directed to the identification of novel PARG modulators which can activate or inhibit DNA repair and/or apoptosis. A PARG modulator is a compound that can activate or inhibit PARG. These modulators are preferably more efficacious and do not have the known side effects of present modulators. One method of identifying an agent that inhibits or activates poly(ADP-ribose) glycohydrolase (PARG) activity comprise the steps of providing a liquid medium that contains a polypeptide having PARG activity contacting the polypeptide with a candidate agent, in the presence of a reference compound having affinity for the polypeptide, under predetermined assay conditions, and determining the affinity of the candidate agent for the polypeptide relative to the reference compound. Thus, the modulation activity of the candidate agent relative to the reference compound is determined. In this method, the polypeptide may be immobilized on a solid support. Further, the polypeptide may be generated in vitro by culturing a cell transformed with a nucleic acid molecule encoding PARG under conditions effective to express the polypeptide.

Another embodiment of the invention is directed to a method of identifying a mutant PARG allele in an individual comprising the step of obtaining genomic material from the individual; digesting the genomic material with a restriction enzyme having a recognition site inclusive of the mutant allele; fractionating the restriction fragments obtained from the digestion; and comparing the fractionation pattern with that obtained for a normal allele, thereby determining the presence or absence of the mutant allele. The fractionating step may be performed with electrophoresis.

Another embodiment of the invention is directed to a method of identifying a mutant PARG allele in an individual comprising the steps of hybridizing an oligonucleotide with genomic material from the individual, which oligonucleotide hybridizes under predetermined hybridization conditions to a region immediately 5' of a predetermined mutation site in the PARG alleles with the 3' terminus of the oligonucleotide complementary to an unmutated PARG allele; extending the oligonucleotide using PCR amplification; and determining the degree to which extension occurs, thereby determining the presence or absence of the mutant allele. The PCR extension reaction may be performed at a temperature above about 50° C. The determination may be performed by conducting electrophoresis (using for example, acrylamide at about 4% to about 10% or agarose and low melting temperature agarose from about 0.8% to about 4%) on the products of PCR amplification.

Another embodiment of the invention is directed to a method of screening molecules for PARG modulating activity (inhibition or activation) comprising the steps of providing a purified PARG enzyme; assaying the enzyme in the presence of a molecule to be screened; and comparing the activity of the PARG enzyme in the presence of the molecule to the activity of the PARG enzyme in the absence of the molecule.

Another embodiment of the invention is directed to a method of gene therapy comprising the step of delivering an oligonucleotide having a sequence complementary to at least a portion of a polynucleotide encoding a PARG enzyme to a cell to be treated. In the method, the oligonucleotide may have a sequence complementary to a sequence encoding a C-terminal portion of a PARG enzyme. Further, in the gene therapy method, the oligonucleotide may further comprise a ribozyme.

Another embodiment of the invention is directed to a method of delivering to a cell surface, an oligonucleotide having a sequence complementary to at least a portion of a polynucleotide encoding a PARG enzyme to a cell to be treated. In the method, the oligonucleotide may have a sequence complementary to a sequence encoding a C-terminal portion of a PARG enzyme. Further, in the method, the oligonucleotide may further comprise a ribozyme. The portion of a polynucleotide encoding a PARG enzyme may be, for example, the polynucleotide encoding the N terminus third of PARG, the middle third of PARG, or the C terminus third of PARG. The portion of a polynucleotide may encode a smaller part of PARG such as the N terminus 10% of PARG, the C terminus 10% of PARG, or any 10% portion in between such as from 10% to 20%, from 20% to 30%, from 30% to 40%, from 40% to 50%, from 50% to 60%, from 60% to 70%, from 70% to 80%, from 80% to 90%. The percent value used means a percent of the linear amino acid sequence. Thus, for a 1000 amino acid protein, the N terminus 10 percent is from amino acid 1 to 100; 10% to 20% percent would be from amino acid 100 to 200 and so on. For a 970 amino acid protein, the N terminal 10% would be from amino acid 1 to 97; 10% to 20% would be from amino acids 98 to 194 amino acids.

Another embodiment of the invention is directed to a method of sensitizing a cell to a chemotherapeutic agent comprising the step of contacting the cell with a molecule that modulates the activity of a PARG enzyme. The molecule may be an oligonucleotide having a sequence complementary to at least a portion of a polynucleotide encoding a PARG enzyme. For example, the oligonucleotide may have a sequence complementary to a sequence encoding a C-terminal portion of a PARG enzyme. The portion of a polynucleotide encoding a PARG enzyme may be, for example, the polynucleotide encoding the N terminus third of PARG, the middle third of PARG, or the C terminus third of PARG. The portion of a polynucleotide may encode a smaller part of PARG such as the N terminus 10% of PARG, the C terminus 10% of PARG, or any 10% portion in between such as from 10% to 20%, from 20% to 30%, from 30% to 40%, from 40% to 50%, from 50% to 60%, from 60% to 70%, from 70% to 80%, from 80% to 90%. The oligonucleotide may further comprise a ribozyme. The method may be used, for example, as a method of treating a diseased cell characterized by the presence of DNA strand breaks. In the treatment, the cell is contacted with a molecule that modulates an enzymatic activity of a PARG enzyme.

Another embodiment of the invention is directed to a pharmaceutical composition comprising an oligonucleotide having a sequence complementary to at least a portion of a polynucleotide encoding a PARG enzyme. The produced molecule may be an oligonucleotide having a sequence complementary to at least a portion of a polynucleotide encoding a PARG enzyme. For example, the oligonucleotide may have a sequence complementary to a sequence encoding a C-terminal portion of a PARG enzyme. The oligonucleotide may comprise a ribozyme activity.

Another embodiment of the invention is directed to a virus that causes the production of an oligonucleotide having a sequence complementary to a polynucleotide encoding a PARG enzyme. This may be, for example, a viral vector which after the infection of a host cell, causes the production of an antisense RNA of PARG. The molecule may be an oligonucleotide having a sequence complementary to at least a portion of a polynucleotide encoding a PARG enzyme. For example, the oligonucleotide may have a sequence complementary to a sequence encoding a C-terminal portion of a PARG enzyme. The oligonucleotide may further comprise a ribozyme activity.

Other embodiments and advantages of the invention are set forth, in part, in the description that follows and, in part, will be obvious from this description and may be learned from the practice of the invention.

BRIEF DESCRIPTION OF THE DRAWINGS

FIG. 5 depicts an alignment of the putative bipartite NLS of bovine, human, and murine PARG and comparison with the bipartite NLS of PARP from different organisms.

FIG. 16 depicts an amino acid sequence alignment of bovine, murine, human, drosophila and C. elegans PARG enzymes.

FIG. 18(A–B) depicts western blots of natural and recombinant expressed PARG.

DETAILED DESCRIPTION OF THE INVENTION

DEFINITIONS

Figure 1:
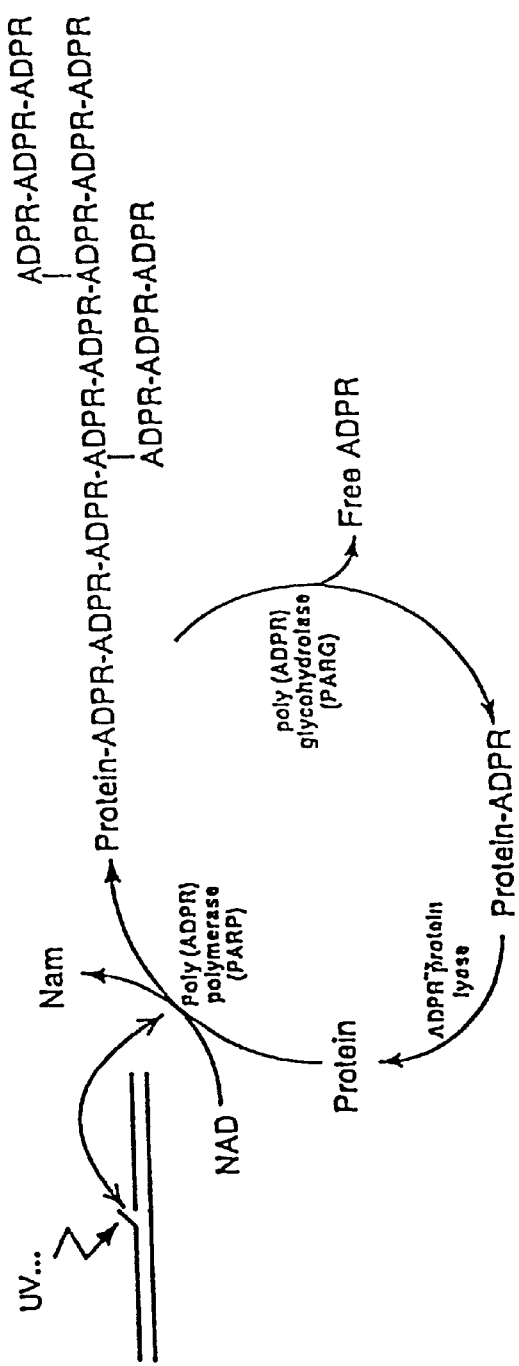
FIG. 1 depicts the cellular biochemical process that occurs after DNA damage.

| List of Abbreviations: | |
| --- | --- |
| ADP | adenosine diphosphate |
| ADPR | ADP-ribose |
| AMP | adenosine monophosphate |
| ASPCR | allele-specific PCR |
| bp | base pair(s) |
| bPARG | bovine PARG |
| CePARG | *C. elegans* PARG |
| dPARG | *Drosophila melanogaster* PARG |
| DTT | dithiothreitol |
| GSH-Sepharose | Glutathione-Sepharose 4B |
| GST | glutathione-S transferase |
| hPARG | human PARG |
| HPLC | high pressure liquid chromatography |
| ICE | interleukin-1 b converting enzyme |
| IPTG | isopropyl-β-D-thiogalactoside |
| kb | kilobase pair(s) |
| MDBK | Madin-Darby bovine kidney cells |
| mPARG | murine PARG |

-continued

List of Abbreviations:

| | |
|---|---|
| NAD | nicotinamide adenine dinucloetide |
| NLS | nuclear location signal |
| PADPR DHB-Sepharose | poly(ADP-ribose)-dihydroxyboronyl-Sepharose |
| PAGE | polyacrylamide-gel electrophoresis |
| PARG | poly(ADP-ribose) glycohydrolase |
| PARP | poly(ADP-ribose) polymerase [EC 2.4.2.30] |
| PCR | polymerase chain reaction |
| PEG-6,000 | polyethylene glycol 6,000 |
| PEG | polyethylene glycol |
| PMSF | phenylmethylsulfonyl fluoride |
| PR-AMP | phosphoribosyl-adenosine monophosphate |
| RFLP | restriction fragment length polymorphism |
| SDS | sodium dodecyl sulfate |
| SSCP | single-strand conformation polymorphism |
| TPCK | Trypsin: L-1 tosylamido-2-phenylethyl chloromethyl ketone. |

An "agonist" as defined herein refers to a molecule which, when bound to PARG, increases or prolongs the effect of PARG. Agonist may include proteins, nucleic acid molecules, carbohydrates, or any other molecules that bind to and modulate the effect of PARG.

An "allele" or "allelic sequence", as defined herein refers to an alternative form of PARG. Alleles may result from at least one mutation in the nucleic acid molecule sequence and may result in altered mRNAs or polypeptides whose structure or function may or may not be altered. Any given natural or recombinant gene may have none, one, or many allelic forms. Common mutational changes which give rise to alleles, are generally ascribed to natural deletions, additions, or substitutions of nucleotides. Each of these types of changes may occur alone, or in combination with the others, one or more times in a given sequence.

An "ortholog" as defined herein refers to a nucleotide or amino acid sequence that is related to a reference nucleotide or amino acid sequence through speciation, and is therefore identical or structurally similar to the reference sequence.

A given nucleotide or amino acid sequence is said to be "substantially identical" with another sequence when the compared sequences have the same residues in the same order, excepting for any degeneracy (nucleotides) and conservative substitutions (amino acids).

A "regulatory sequence" of an expression vector is a DNA sequence necessary for inducing transcription of a gene, and includes a functional promoter and/or enhancer sequence. The term "operatively linked" as used herein means that a first nucleotide sequence, such as a regulatory element, is fused in flame with a second nucleotide sequence so as to afford a faithful transcription of the entire nucleotide sequence, which upon translation yields the desired protein.

The term "immunoreactivity" and related terms refers to the ability of antibodies and fragments thereof to bind to particular regions (antigens) presented by polypeptides and proteins, presented to the antibodies either as immunogens or targets. Typically, the binding affinity of the antibodies for their antigen is in the range $10^5$ to $10^{11}$, with higher affinities being preferred.

The term "specific immunoreactivity" refers to the ability of antibodies and fragments thereof to bind to particular regions (antigens) presented by polypeptides and proteins, presented to the antibodies either as immunogens or targets and not to unrelated antigens. For example, an antibody with specific immunoreactivity to actin will bind actin but would not bind another protein, such as a polymerase, which do not share epitopes with actin.

The term "nucleic acid molecule" refers to DNA, RNA and nucleic acid molecule analogs such as PNA and the like.

PNA or "Peptide Nucleic Acid" is a nucleic acid molecule analog that has a neutral "peptide-like" backbone with nucleobases that allow the molecule to hybridize to complementary RNA or DNA with higher affinity and specificity than corresponding oligonucleotides. PNA can be made to be more resistant to normal nucleases and are especially desirable, for example, in gene therapy. PNA is known to one of skill in the art and can be purchased or custom synthesized in numerous commercial laboratories including PerSeptive Biosystems, Inc. (Framingham, Mass.).

The term "modulate" means to activate or inhibit. For example, a PARG modulator may activate or inhibit PARG activity. "Modulation activity" means the amount of activation or inhibition. For example, a compound that increase PARG (or any other enzyme) activity by 10% will have a modulation activity of 10%. Conversely, a compound that decreases PARG activity by 10% will have a modulation activity of −10%.

As used herein, a given nucleotide or amino acid sequence is said to have a defined percentage of sequence similarity with another sequence when the two sequences differ by no more than the specified sequence similarity, including conservative substitutions, insertions, and deletions. Degenerate codons do not result in a change in amino acid upon translation, therefore, it is appreciated that identical amino acids can be encoded by several equivalent codons. The term "homology" and "sequence similarity" should have the same meaning for the purpose of this patent. Similarity parameters may be any generally acceptable parameter. For the purposes of this patent, percent similarity between two polymers such as nucleic acid molecules and polypeptides is preferably defined by Karlin and Altschul (11). The similarity algorithms of Karlin and Altschul are well known to those of skill in the art as exemplified by their adoption by the National Center for Biological Information. For nucleic acid molecule sequence searching, one desirable set of parameters would M (score for a pair of matching residues) at 5; N (score for mismatching residues) at −4; W (word length) at 11. For proteins, it is well known that some amino acids are similar and that substitution would be conservative. That is, for example, the replacement of an acidic amino acid with another acidic acid would be consider a conservative mismatch while the replacement of an acidic amino acid with a basic amino acid would be consider a more divergent mismatch. Preferably, the parameters for a desirable protein similarity determination are expressed in the sequence similarity matrix BLOSUM62 as described in Henikoff & Henikoff (12). Other similarity matrixes that are also preferred in the invention are PAM40, PAM 120 and PAM250 as described in Altschul (13).

The rapid synthesis of ADP-ribose polymers that occurs in response to DNA strand breaks is accompanied by very rapid polymer turnover, indicating that PARP and PARG activities are closely coordinated as cells respond to DNA damage. While PARP has been widely studied, information concerning structure and function relationships of PARG is much more limited. The present invention discloses the isolation of a cDNA encoding the bovine, human, murine and drosophila PARG and their deduced amino acid sequences.

The availability of PARP cDNA has allowed a number of molecular genetic approaches to study the function(s) of ADP-ribose polymer metabolism and the availability of PARG cDNA should allow the design of additional molecular genetic approaches for studying this metabolism. For example, disruption of the gene encoding PARG in mice containing a normal PARP gene will allow the determination of whether other cellular enzymes can replace PARG in the turnover of ADP-ribose polymers and/or whether development of animals will occur in the absence of PARG. Alternatively, disruption of the PARG gene in mice containing a disrupted PARP gene may provide insights for the coordinated function of PARP and PARG.

One embodiment of the invention is directed to a deoxyribonucleic acid (DNA) molecule that encodes a polypeptide having poly(ADP-ribose) glycohydrolase (PARG) activity. Preferably, the molecule is of mammalian origin, such as, for example, of human origin.

In a preferred embodiment, a DNA molecule of the invention comprises a nucleotide sequence with at least about 70% sequence similarity with a sequence shown in a sequence shown in SEQ ID NO: 1, SEQ ID NO: 3, SEQ ID NO: 5, SEQ ID NO: 7, and SEQ ID NO: 9. Higher degrees of sequence similarity, such as about 80%, about 90%, and about 100% are preferred. Most preferred is a DNA molecule comprising a nucleotide sequence substantially identical with any one of sequence shown in SEQ ID NO: 1, SEQ ID NO: 3, SEQ ID NO: 5, SEQ ID NO: 7, and SEQ ID NO: 9. It is preferred that a DNA molecule of the present invention comprises at least about 1000 nucleotides and has a nucleotide sequence with at least 80% sequence similarity with a sequence of SEQ ID NO: 1, SEQ ID NO: 3, SEQ ID NO: 5, SEQ ID NO: 7, and SEQ ID NO: 9. Most preferably, the DNA molecule consist of a nucleotide sequence selected from the group consisting of SEQ ID NO: 1, SEQ ID NO: 3, SEQ ID NO: 5, SEQ ID NO: 7, and SEQ ID NO: 9.

For a DNA molecule of the present invention based on a human PARG gene it is preferred that the molecule comprises a nucleotide sequence that shows similarity to the sequence shown in SEQ ID NO: 3 from about residue 2113 to about residue 3105. More preferably, the sequence similarity is from about residue 1240 to about residue 3105. Still more preferably, the DNA molecule comprises a nucleotide sequence similarity to the coding sequence for the full-length hPARG as shown in SEQ ID NO: 3 from about residue 175 to about residue 3105.

A DNA molecule of the present invention affords probes and primer molecules that can be used in hybridization assays and PCR amplification. An exemplary oligonucleotide is less than about 1000 residues in length and comprises a nucleotide sequence at least about 10 residues long to ensure hybridization. Preferably, the at least about 10 residue region of the oligonucleotide is complementary to a sequence shown in SEQ ID NO: 1, SEQ ID NO: 3, SEQ ID NO: 5, SEQ ID NO: 7, and SEQ ID NO: 9. Typically, the oligonucleotide will be a DNA molecule, which can be labeled by any method as desired, for example, with a radiolabel, a fluorescence label, or chemi-luminescent label.

Another embodiment of the invention is directed to a nucleic acid molecule that hybridizes to in a nucleic acid blot (Southern blot, Northern blot) to a sequence of SEQ ID NO: 1, SEQ ID NO: 3, SEQ ID NO: 5, SEQ ID NO: 7, or SEQ ID NO: 9 under stringent hybridization conditions. A nucleic acid blot may be made using techniques defined in Molecular Cloning, Second Edition, Sambrook et al., Cold Spring Harbor Press, Cold Spring Harbor, N.Y. DNA to be analyzed may be separated in agarose or acrylamide gels. The DNA may be transferred to nylon or nitrocellulose membrane using techniques known to those in the art. Stringent hybridization condition may be for example, prehybridizations 42° C. in 50% formamide, 0.25 M sodium phosphate buffer, pH 7.2, 0.25 M NaCl, 7% SDS, 1 mM EDTA for 10 hours, 100 ug denatured salmon sperm DNA, hybridization at 42° C. in 50% formamide, 0.25 M sodium phosphate buffer, 100 ug denatured salmon sperm DNA, pH 7.2, 0.25 M NaCl, 7% SDS, 1 mM EDTA, 1 ng/ml probe with a specific activity of $10^9$ cpm/ug DNA, for 16 hours. The probe may comprise any contiguous sequence from SEQ ID NO: 1, SEQ ID NO: 3, SEQ ID NO: 5, SEQ ID NO: 7, or SEQ ID NO: 9. Preferably, said contiguous sequence is at least about 50 bases long, more preferably, the contiguous sequence is at least about 75 bases long, such as at least about 100 bases, at least about 200 bases long or at least about 300 bases long. The complete sequence of SEQ ID NO: 1, SEQ ID NO: 3, SEQ ID NO: 5, SEQ ID NO: 7, or SEQ ID NO: 9. Methods of labeling probes to with radioactive labels are known to those of skill in the art.

Method of washing after stringent hybridization are known. A stringent washing may comprise, for example, two washes at in 2×SSC, 0.1% SDS for 15 minutes each at room temperature; two washes in 0.2×SSC, 0.1% SDS for 15 minutes each at room temperature; and a final three washes in 0.2×SSC, 0.1% SDS for 15 minutes each at 60° C. The final wash may be increased in temperature for reduced background. For example, the final wash may be a final three washes in 0.2×SSC, 0.1% SDS for 15 minutes each at 65° C. or a final three washes in 0.2×SSC, 0.1% SDS for 15 minutes each at 68° C.

If a radioactive probe is used, hybridization may be monitored using known techniques such as autoradiogram or a two dimensional measurement of radioactivity.

An anti-sense oligonucleotide is also afforded by the present invention. The anti-sense molecule is typically less than about 1000 residues in length to ensure ease of synthesis, and hybridizes to an RNA molecule, e.g., messenger RNA, which has at least 70% sequence Hilarity with a sequence of SEQ ID NO: 1, SEQ ID NO: 3, SEQ ID NO: 5, SEQ ID NO: 7, SEQ ID NO: 9. Preferably, the anti-sense molecule is at least about 10 nucleotides in length to ensure hybridization with mRNA. Even more preferably, the antisense molecule may be at least about 15 nucleotides in length such as, for example, at least about 20 nucleotides in length; at least about 30 nucleotides in length; at least about 50 nucleotides in length; at least about 75 nucleotides in length; at least about 100 nucleotides in length; at least about 150 nucleotides in length; at least about 200 nucleotides in length; at least about 500 nucleotides in length; at least about 1000 nucleotides in length; or at least about 1500 nucleotides in length. It is also preferred that the molecule has a ribozyme activity so that it can degrade the mRNA that it binds to.

An antisense oligonucleotide may be used therapeutically to inhibit translation of mRNA encoding PARG. Synthetic antisense oligonucleotides may be produced, for example, in a commercially available oligonucleotide synthesizer. This invention provides a means to therapeutically alter levels of expression of a human or other mammalian PARG by the use of a synthetic antisense oligonucleotide drug that inhibits translation of mRNA encoding PARG. Synthetic antisense oligonucleotides, or other antisense chemical structures designed to recognize and selectively bind to mRNA, are constructed to be complementary to portions of the nucleotide sequence shown in SEQ ID NO: 1, SEQ ID NO: 3, SEQ ID NO: 5, SEQ ID NO: 7 and SEQ ID NO: 9. An antisense oligonucleotide may be designed to be stable in the blood stream for administration to patients by injection, or in laboratory cell culture conditions, for administration to cells removed from the patient. The antisense may be designed to be capable of passing through cell membranes in order to enter the cytoplasm and nucleus of the cell by virtue of physical and chemical properties of the antisense oligonucleotide which render it capable of passing through cell membranes (e.g., by designing small, hydrophobic antisense oligonucleotide chemical structures) or by virtue of specific transport systems in the cell which recognize and transport the antisense oligonucleotide into the cell. In addition, the antisense oligonucleotide can be designed for administration only to certain selected cell populations by targeting the antisense oligonucleotide to be recognized by specific cellular uptake mechanisms which bind and take up the antisense oligonucleotide only within certain selected cell populations. For example, the antisense oligonucleotide may be designed to bind to transporter found only in a certain cell type, as discussed above. The antisense oligonucleotide may be designed to inactivate the PARG mRNA by (1) binding to the PARG mRNA and thus inducing degradation of the mRNA by intrinsic cellular mechanisms such as RNase I digestion, (2) by inhibiting translation of the mRNA target by interfering with the binding of translation-regulating factors or of ribosomes, or (3) by inclusion of other chemical structures, such as ribozyme sequences or reactive chemical groups, which either degrade or chemically modify the target mRNA. Synthetic antisense oligonucleotide drugs have been shown to be capable of the properties described above when directed against mRNA targets (14). In addition, coupling of ribozymes to antisense oligonucleotides is a promising strategy for inactivating target mRNA (15). In this manner, an antisense oligonucleotide directed to PARG may serve as a therapy to reduce PARG expression in particular target cells of a patient and in any clinical condition that may benefit from reduced expression of PARG.

It is known by those in the art that as a result of the degeneracy of the genetic code, a multitude of nucleotide sequences encoding PARG, some bearing minimal homology to the nucleotide sequences of any known and naturally occurring gene, may be produced. Thus, the invention contemplates a nucleic acid molecule that encodes a polypeptide consisting of an amino acid sequence selected from the group consisting of SEQ ID NO: 2, SEQ ID NO: 4, SEQ ID NO:6, SEQ ID NO: 8 and SEQ ID NO: 10. The invention contemplates each and every possible variation of nucleotide sequence that could be made by selecting combinations based on possible codon choices that would encode the oligopeptides disclosed herein. These combinations are made in accordance with the standard triplet genetic code as applied to the nucleotide sequence of naturally occurring PARG and all such variants are to be considered as being, specifically disclosed.

Although nucleic acid molecules which encode PARG and its variants preferably hybridizes under high stringency conditions to the nucleotide sequence of the naturally occurring PARG gene under appropriate conditions of stringency, it may be advantageous to produce nucleotide sequences encoding PARG or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding PARG and its derivatives and variants without altering the produced amino acid sequence include the production of RNA transcripts having more desirable properties, such as greater half-life, than transcripts produced from the naturally occurring sequence.

In order to express a biologically active or immunologically active PARG, the nucleic acid molecule encoding PARG or functional equivalents, may be inserted into appropriate expression vector, such as, for example a vector which contains the necessary elements for the transcription and translation of the inserted coding sequence. Thus, another aspect of the present invention is an expression vector comprising a regulatory sequence operatively linked to nucleic acid molecule comprising a nucleotide sequence disclosed herein. For example, an expression vector can contain a nucleotide sequence at least about 1000 base pairs in length, which has at least about 70%, about 80%, or higher, sequence similarity with a sequence shown in SEQ ID NO: 1, SEQ ID NO: 3, SEQ ID NO: 5, SEQ ID NO: 7, and SEQ ID NO: 9.

Methods that are known to those skilled in the art may be used to construct expression vectors containing sequences encoding PARG and appropriate transcriptional and translational control elements. These methods include in vitro recombinant DNA techniques, synthetic techniques, and in vivo genetic recombination.

A variety of expression vector/host systems may be utilized to contain and express sequences encoding PARG. These include, for example, microorganisms such as bacteria transformed with recombinant bacteriophage, plasmid, or cosmid DNA expression vectors; yeast transformed with yeast expression vectors; insect cell systems infected with virus expression vectors (e.g., baculovirus), insects infected with virus expression vectors (e.g., fall army worm infected with baculovirus); plant cell systems transformed with virus expression vectors (e.g., cauliflower mosaic virus, CaMV; tobacco mosaic virus; TMV) or with bacterial expression vectors (e.g., Ti or bacterial plasmids); or animal cell systems. The invention is not limited by the host cell employed.

Prokaryotic expression systems are commercially available from a number of suppliers worldwide. Prokaryotic expression vectors provide a convenient system to synthesize proteins. If it is desired to express a protein with characteristics such as immunogenic properties, 3D conformation, and other features exhibited by authentic PARG, the protein may be expressed in an eukaryotic protein expression system. The eukaryotic expression systems are numerous and include mammalian, amphibian, plant, insect, and yeast expression systems.

Yeast hosts that can be used for expression include *Saccharomyces cerevisiae, Schizosaccharomyces pombe, Pichia pastoris, Hansela polymorpha, Kluyveromyces lactis*, and *Yarrowia lipolytica*. Yeast hosts offer the advantages of rapid growth on inexpensive minimal media and ease in large-scale production using bioreactors. Another advantage of yeast is the ability to direct expression to cytoplasmic localization or for extracellular export.

Most yeast vectors for protein expression are derivatives of the *S. cerevisiae* 2μ (two micron) plasmid. Yeast vectors include pYES and pEST from Stratagene (La Jolla, Calif.). Constitutive gene expression by the yeast plasmid cassette can be mediated by well known promoters such as the glyceraldehyde-3-phosphate dehydrogenase promoter (TDH3); the triose phosphate isomerase promoter (TPI1); the phosphoglycerate isomerase promoter (PGK1); the alcohol dehydrogenase isozyme II (ADH2) gene promoter; GAL1 and GAL10 promoters; the metallothionein promoter from the CUP1 gene (induced by copper sulfate); and the PHO5 promoter (induced by phosphate limitation). Proper termination of yeast transcripts is known to those in the art. Termination signals may include the MF-alpha-1, TPI1, CYC1, and PGK1 genies. These termination signals may be spliced onto the 3' end of the insert to provide proper termination.

Insect expression systems include baculovirus based vectors designed to express foreign proteins in a number of insect hosts and insect cell line hosts. Insect and insect cell lines may be of Drosophila melanogaster, Aedes albopictus, Spodoptera frugiperda, and Bombyx mori origin. Numerous expression systems comprising cells, vectors, hosts and the like can be purchased from a variety of commercial sources.

The control elements or regulatory sequences necessary for the proper expression of the insert, in this case PARG, may comprises promoters, enhancers (including both proximal and distal control elements) which interact with the host proteins to carry out transcription and translation. Such elements may vary in their strength and specificity and are known to those in the art. Depending on the vectors system and host utilized, any number of suitable transcription and translation elements, including constitutive and inducible promoters, may be used. For example, the LacZ promoter may be used in a bacterial cell; the baculovirus polyhedrin promoter may be used in an insect cell; plant promoters such as heat shock promoters, and storage protein promoters, plant virus promoters and the like may be used in a plant cell. In a mammalian cell expression system, an SV40 promoter or EBV promoter may be used.

Methods and protocols for both prokaryotic and eukaryotic expression systems are generally known to those in the art. Further, the cells, vectors, growth medium may be purchased from commercial suppliers. The catalogs and product literature of commercial suppliers provide detailed protocols to enable the expression of proteins in prokaryotic and eukaryotic systems including bacterial, yeast, insect, insect cell, and mammalian cell systems. The product literature and catalogs of Clontech (Palo Alto, Calif.), Invitrogen (Carlsbad, Calif.), Life Technologies (Rockville, Md.), Novagen (Madison, Wis.), Pharmigen (San Diego, Calif.), Quantum Biotechnologies (Montreal, Quebec, Canada), and Stratagene (La Jolla, Calif.) are incorporated herein by reference.

A further aspect of the invention is isolated proteins and protein fragments having poly(ADP-ribose) glycohydrolase (PARG) activity. Such a protein can comprise an amino acid sequence with sequence similarity of at least about 70%, about 80% or higher to a sequence shown SEQ ID NO: 2, SEQ ID NO: 4, SEQ ID NO: 6, SEQ ID NO: 8, and SEQ ID NO: 10. For example, the full-length bovine PARG has a molecular weight greater than about 100 kDa, thereby distinguishing it from previously known PARGs. The protein may be purified, for example, from cell lysates using the antibodies of the invention. The purification may be through an antibody column.

PARG polypeptides are another aspect of the invention. Polypeptides of PARG may be used, for example, to generate antibodies in an immunogenic procedure. To be effective it is preferred that the polypeptides are at least about 6 amino acid residues in length, such as for example, at least about 10 amino acids in length, at least about 20 amino acids in length, at least about 30 amino acids in length, at least about 50 amino acids in length, at least about 75 amino acids in length, at least about 100 amino acids in length, at least about 150 amino acids in length, at least about 200 amino acids in length, or at least about 400 amino acids in length. In one embodiment, the polypeptide has a molecular weight less than about 65 kDa and with at least about 80% sequence similarity with a sequence shown in SEQ ID NO: 2, SEQ ID NO: 4, SEQ ID NO: 6, SEQ ID NO: 8, and SEQ ID NO: 10. The polypeptide may consist of the sequence set forth in SEQ ID NO: 2, SEQ ID NO: 4, SEQ ID NO: 6, SEQ ID NO: 8, or SEQ ID NO: 10.

The polypeptide of the invention may be conjugated to a larger molecule, such as, for example, keyhole lymphet hemocyanin (KLH), to increase the immunogenicity of the polypeptide. The increased immunogenicity of the polypeptide will, in turn, increase the yield of antibody. Preferably, the polypeptide has a molecular weight less than about 40 kDa and with at least about 90% sequence similarity with a sequence shown in SEQ ID NO: 2, SEQ ID NO: 4, SEQ ID NO: 6, SEQ ID NO: 8, and SEQ ID NO: 10. The polypeptide can also be used in a wide variety of assays, e.g., as a competitor of antigen in a liquid sample in an antibody-based assay. Therefore, it is preferred that the polypeptide has poly(ADP-ribose) glycohydrolase (PARG) activity. A particularly preferred polypeptide is of human origin and comprises an amino acid sequence substantially identical with SEQ ID NO: 4 from about residue 647 to about residue 977—the C terminus catalytic region of the enzyme. Longer sequences more inclusive of the natural molecule are of course also contemplated.

The invention also encompasses PARG variants and alleles. A preferred PARG variant is one having at least 80% and more preferably at least 90% amino acid similarity to the amino acid of SEQ ID NO: 2, SEQ ID NO: 4, SEQ ID NO: 6, SEQ ID NO: 8 and SEQ ID NO: 10 and which retains at least one biological, immunological or other functional characteristic or activity of PARG. A most preferred PARG variant is one having at least 95% amino sequence similarity or identity to human PARG (SEQ ID NO: 3).

Antibodies to PARG may be generated using numerous established methods that are well known in the art. One example of such a method is described in the Examples. Generated antibodies may include, for example, polyclonal, monoclonal, chimeric, single chain, Fab fragments, Fab' fragments, Fab' (2) fragments, and fragments produced by a FAB expression library. Humanized antibodies and single chain antibodies may also be produced after the amino acid sequence of effective antibodies are determined.

For the production of antibodies, various hosts including goats, rabbits, rats, mice, humans, and others, may be immunized by injection with PARG or any fragment or oligopeptide thereof which has immunogenic properties. Depending on the host species, various adjuvants may be used to increase immunological response. Such adjuvants include, for example, Freund's mineral gels such as aluminum hydroxide, and surface-active substances such as lysolecithin, pluronic polyols, polyanions, peptides, oil emulsions, keyhole limpet hemocyanin, and dinitrophenol. Among adjuvant used in humans, BCG (bacilli Calmette-Guerrin) and Corynebacterium parvum are especially preferable.

It is preferred that the oligopeptides, peptides, or fragments used to induce antibodies to PARG have an amino acid sequence consisting of at least five amino acids and more preferably at least about 10 amino acids, such as for example about 20 amino acids or about 40 amino acids. It is also preferable that they are identical to a portion of the amino acid sequence of the natural PARG. Short stretches of PARG amino acids may be fused with those of another protein such as keyhole limpet hemocyanin and antibodies may be produced against the chimeric molecule.

Antibodies may be produced by inducing in vivo production in the lymphocyte population of a living animal or by screening immunoglobulin libraries or panels of highly specific binding reagents as disclosed in published procedures (16).

Antibody fragments that contain specific binding sites for PARG may be generated. For example, such fragments include the F(ab')$_2$ fragment, Fab fragment, Fab' fragment which can be produced by enzymatic digestion of the antibody molecule. Alternatively, Fab expression libraries may be constructed to allow rapid and easy identification of monoclonal Fab fragments with the desired specificity (Huse, W. D. (1989) Science 254, 1275–1281).

Therapeutic Methods

A method of preventing, treating, or ameliorating a disease condition in a patient, which disease state is affected by the level of PARG expression is also contemplated. This method entails administering a therapeutically effective amount of a poly(ADP-ribose) glycohydrolase (PARG) inhibitor or activator to the individual. Particularly, implicated disease states are neoplastic disorder, myocardial infarction, vascular stroke and neurodegenerative disorders.

In one embodiment, antisense oligonucleotides for PARG may be used alone or in combination with other chemotherapeutic agents to treat neoplastic disorder. The antisense oligo is designed to hybridize in vivo to messenger RNA expressed by the organism. The use of anti-sense molecules in a therapeutic setting is described, for example, by S. Agrawal, *Antisense Therapeutics*, Humana Press. Currently favored protocols call for the oligo to have ribozyme activity in an effort to degrade the mRNA. These methods are described, for example, in *Therapeutic Application of Ribozymes*, K. Scanlon, ed., Humana Press. Therefore, in one embodiment, an antagonist of PARG may be administered to a subject to prevent or treat neoplastic disorder.

PARG levels may be enhanced to suppress DNA repair and increase a cell's susceptibility to chemotherapy drugs. Therefore, in another embodiment, an PARG enhancer is administered to a subject along with a chemotherapeutic drug as a treatment for neoplastic disorder.

Neoplastic disorders that can be treated by PARG elevation and chemotherapy include benign and malignant neoplasm such as, for example, adenocarcinoma, leukemia, lymphoma, melanoma, myeloma, sarcoma, teratocarcinoma, hyperplasia and hypertrophy. Neoplastic disorders may include, in particular, neoplastic disorders of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. For the purposes of this invention, a neoplastic disorder is any new and abnormal growth; specifically a new growth of tissue in which the growth is uncontrolled and progressive. Malignant cancer is a subset of neoplastic disorders which show a greater degree of anaplasia and have the properties of invasion and metastasis.

The synthesis of effective anti-sense inhibitors is known. Numerous approaches have been previously described and generally involve altering the backbone of the polynucleotide to increase its stability in-vivo. Exemplary oligonucleotides and methods of synthesis are described in U.S. Pat. Nos. 5,661,134; 5,635,488; and 5,599,797 (phosphorothioate linkages), U.S. Pat. Nos. 5,587,469 and 5,459,255 (N-2 substituted purines), U.S. Pat. No. 5,539,083 (peptide nucleic acids) and U.S. Pat. Nos. 5,629,152; 5,623,070; and 5,610,289 (miscellaneous approaches). The disclosures of each of these references are incorporated herein by reference.

Significantly, the present invention discloses a method of identifying an agent that inhibits or activates poly(ADP-ribose) glycohydrolase (PARG) activity. Such method comprises (i) providing a liquid medium that contains a polypeptide of the present invention; (ii) contacting the polypeptide with a candidate agent, in the presence of a reference compound having affinity for the polypeptide, under predetermined assay conditions; and (iii) determining the affinity of the candidate agent for the polypeptide relative to the reference compound, thereby determining the inhibition or activation activity of the candidate agent relative to the reference compound. These determinations can be facilitated by immobilizing the polypeptide on a solid support. Alternatively, the polypeptide can be generated in vitro by culturing a cell transformed with a PARG gene under conditions effective to express the polypeptide.

Combination therapies are also afforded by the present invention in which a PARG inhibitor or activator is administered in combination with a chemotherapeutic or a "clot-busting" drug. The clot-busting drug may be, for example, tissue plasminogen activator (t-PA) or streptokinase.

In some cases it may be desired to overexpress PARG in the cells of an organism in order to achieve the correct PARP/PARG balance. In this context of gene therapy, it is desired to stably transfect target cells with a vector, such as, for example, a viral or a DNA (nucleic acid) vector, so that the desired gene is overexpressed. Gene therapy vector systems and protocols are well known and are described, for example, in the *Internet Book of Gene Therapy* (17) Antisense and ribozyme approaches to cancer gene therapy are described in chapters 7–9 of the *Internet Book of Gene Therapy*, and are incorporated herein by reference. Another reference is *Gene Therapy Protocols*, P. Robbins, ed., Humana Press. Furthermore, gene therapy methods have advanced greatly and are well documented in numerous issued US patents. Gene therapy may be practiced, for example, by substituting a nucleic acid molecule of the invention with the nucleic acid molecule described in the methods referred to in any issued US patents directed to gene therapy (18).

Any of the therapeutic methods described above may be applied to any subject in need of such therapy, including, for example, mammals such as dogs, cats, cows, horses, rabbits, monkeys, and most preferably, humans.

Diagnostic Methods

Methods of genotyping an individual for a mutant PARG allele are also afforded by the present invention. A number of protocols are available for identifying a mutant allele as described herein once the nucleotide sequence encoding PARG is known. Some exemplary methods are restriction fragment length polymorphism (RFLP), allele-specific PCR (ASPCR) and single-strand conformation polymorphism (SSCP). Armed with this information, the genetic susceptibility of an individual to an above-mentioned disease condition can be assessed.

An allele-specific method for identifying point mutations by differential PCR amplication is described by (19). A non-electrophoretic method of genotyping with allele-specific PCR employs a dye specific for double-stranded DNA (20). A method of detecting mutations referred to as single-stranded conformation polymorphism (SSCP) is presently widely employed (21). A hybrid of SSCP and Sanger dideoxy sequencing, called dideoxy fingerprinting (ddF) has recently been described (22).

Other methods of identifying allelic mutations are known to the skilled artisan. Probably the most commonly used method of genotyping is restriction fragment length polymorphism (RFLP) (23), which is employs one or more restriction enzymes to identify mutant alleles occurring within a restriction site. This method has been used extensively in forensic applications and is employed commercially by such companies as Helix Biotech, Inc. Reliagene Technologies, Inc. and Gen Test Laboratories, Inc. Accordingly, an instant mutant PARG allele can be detected by RFLP methods, optionally by one of these commercial entities. The above methods are most effective in the detection of homozygotes for the defective allele.

An RFLP method of identifying a mutant PARG allele in an individual entails: (i) obtaining genomic material from the individual; (ii) digesting the genomic material with a restriction enzyme having a recognition site inclusive of the mutant allelic; (iii) fractionating the restriction fragments obtained from the digestion, e.g., by electrophoresis; and (iv) comparing the fractionation pattern with that obtained for a normal allele, thereby determining the presence or absence of the mutant allele.

An ASPCR method of identifying a mutant PARG allele in an individual entails: (i) hybridizing an oligonucleotide with genomic material from the individual; (ii) attempting to extend the oligonucleotide using PCR amplification; and (iii) determining the degree to which extension occurs, thereby determining the presence or absence of the mutant allele. In this method, it is preferred that the oligonucleotide hybridizes under predetermined hybridization conditions to a region immediately 5' of a predetermined mutation site in the PARG allele with the 3' terminus of the oligonucleotide complementary to an unmutated PARG allele. In these protocols, the PCR extension reaction is generally attempted at a temperature above about 50° C., more preferably above about 60° C.

A variety of protocols including ELISA, RIA and FACS for measuring PARG levels are known in the art and provide a basis for diagnosing altered or abnormal levels of PARG expression. Normal or standard values for PARG expression may be established by combining, body fluids and tissue biopsies from normal mammalian subjects, rupturing the cells or permeating the cells, combining the cells with antibody under conditions suitable for complex formation. The amount of standard complex formation may be quantified by various methods but preferably by photometric means. Quantities of PARG expressed in subject, control, and disease sample are compared to standard values to determine between normal, reduced or enhanced levels of PARG.

A still further aspect of the invention pertains to an antibody immunoreactive with a polypeptide of the present invention. Preferably the antibodies are specifically immunoreactive with the polypeptides of this invention such as, SEQ ID NO: 2, SEQ ID NO: 4, SEQ ID NO: 6, SEQ ID NO: 8, and SEQ ID NO: 10. Frequently it is desired to label the antibody, e.g., with a radiolabel, fluorescent or epitope label, to permit visualizing the antibody. Thus, antibodies immunoreactive with the PARG of this invention are afforded, which can be used to study features of PARG heterogeneity and possible modes of regulation. The high degree of sequence similarity between bovine PARG, human PARG and murine PARG permits eliciting antibodies to PARG of one species, which are found to be cross-reactive with PARGs from other organisms. These antibodies are valuable in characterizing PARG in-vivo under defined physiological conditions in many different organisms.

Accordingly, a method of detecting a polypeptide having PARG activity, for example, a diagnostic assay, entails: (i) contacting the polypeptide with an aforementioned antibody of the invention; and (ii) determining whether the antibody immunoreacts with the polypeptide. Binding can be ascertained in an sandwich assay, as is well known, due to the ability of the antibodies to immunoreact with an epitope of PARG. Preferably, monoclonal antibodies, such as those prepared by the method of Kohler and Milstein (24) and labeled antigens effective in competing with the polypeptide, are employed. Exemplary assays are disclosed in U.S. Pat. No. 4,375,110, the disclosure of which is incorporated herein by reference.

The present invention includes immunoreactive fragments of a PARG enzyme. Immunoreactive fragments can be fragments that can elicit an immune response that recognizes a PARG enzyme. Alternatively, immunoreactive fragments can be fragments that are specifically bound by an antibody that specifically binds a PARG enzyme. Any of variety of methods may be employed in order to identify contiguous peptide fragments of a PARG enzyme that comprise immunoreactive sequences. PARG enzymes may be fractionated by proteases, cyanogen bromide, etc. and the resultant fragments assessed for their capacity to specifically bind anti-PARG antibodies.

In an alternative embodiment, one or more synthetic peptides may be prepared in order to locate contiguous amino acid sequences that are immunoreactive. The peptides may have a sequence that includes a series of contiguous amino acids that are identical to a series of continuous amino acids of a PARG enzyme. The peptides may be of about six amino acids to about 500 amino acids in length. The peptide may also include sequences that are not identical to sequences of a PARG so long as it includes at least about six continuous amino acids that are identical to about six contiguous amino acids of a PARG enzyme. In a preferred embodiment, the peptide will be about 50 amino acids in length. In other preferred embodiments the length of the peptide may be from about six amino acids to about 30 amino acids.

The peptides of the present invention may comprise amino acid sequences that elicit antibodies that specifically bind to the peptide or to a PARG enzyme. Alternatively, the peptides may contain sequences that are specifically bound by anti-PARG, antibodies. Peptides that are bound by anti-PARG antibodies may identified through the use of Epitope Scanning™ strategy (Cambridge Research Biochemicals, Inc.). Thus, the linear sequence of amino acids of a particular PARG enzyme is used to construct a set of peptides of defined length which overlap other members of the set by one or more residues. The peptides may be any length; however, lengths of from about 6 to 25 amino acids are preferred. In selecting the length, a general consideration is that antibodies that recognize linear native epitopes constitute approximately 60–70% of the anti-protein antibody population (25).

The number of overlapping amino acids will generally be more than half of the length of the peptides. That is, if the peptides are about 20 amino acids long, the overlap may be 11 or more amino acids long. In preferred embodiments, each peptide will be selected such that the number of overlapping amino acid residues in adjacent peptides is from about (n−1) to (n−3), where "n" is the number of amino acids in the peptide. An overlap of (n−1) is particularly preferred. Thus, in a particularly preferred embodiment, a first peptide may have the amino acid sequence of residues 1–10 of a PARG enzyme, a second peptide may have the amino acid sequence of residues 2–11 of the same PARG enzyme, a third peptide may have the sequence of residues 3–12 of the same PARG enzyme and so on until the entire sequence of the PARG enzyme has been synthesized in fragments.

The peptides may be synthesized using any means known to those of skill in the art. In a preferred embodiment, the peptide will be synthesized using an automated synthesizer such as a multipin peptide synthesis system. Such systems or peptides synthesis services are commercially available from suitable providers known to those skilled in the art.

To identify suitable peptides, each peptide is introduced into a well of a microtiter plate, and assayed for its ability to bind to antibodies elicited by a PARG enzyme. Such assays may be conducted in various ways known to those skilled in the art. One suitable assay is conducted by immobilizing a peptide on the surface of a well and then contacting the peptide with a solution containing an anti-PARG antibody. After washing, the well is contacted with a labeled antibody that specifically binds to the anti-PARG antibody. Thus, the presence of label in the well indicates that the anti-PARG antibody bound to the immobilized peptide. Another preferred method of determining the ability of the peptide to be specifically recognized by anti-PARG antibodies is a competitive ELISA.

Once a particular peptide has been found to bind to anti-PARG antibodies, the peptide can be used to elicit mono specific antibodies. By immunizing an experimental animal with a single peptide containing a single antigenic determinant, the antibodies elicited will all specifically bind to the same antigenic determinant even though the antibodies are not monoclonal.

Where desired, the peptides can be modified to increase their immunogenicity. Thus, they may be modified to contain an amino-terminal and/or a carboxyl-terminal cysteine or lysine residue with or without spacer arms. The peptides may be conjugated to carriers such as bovine serum albumin, ovalbumin, human serum albumin, KLH (keyhole limpet hemocyanin) or tetanus toxoid. The use of human serum albumin is preferred over ovalbumin or bovine serum.

The peptides, alone or conjugated to a carrier, may be themselves capable of eliciting an antibody response when administered to an experimental animal. Alternatively, the peptides, alone or conjugated to a carrier, may be administered in conjunction with an adjuvant. Those skilled in the art will understand that a variety of materials may function as adjuvants. Examples of possible adjuvants include, but are not limited to, Freund's complete adjuvant, Freund's incomplete adjuvant, lipopolysaccharide (LPS) and the like. Any material that increases the immune response to a fragment of a PARG enzyme may be used as an adjuvant.

The ability to produce large amounts of active PARG enzyme permits, for the first time, the large scale screening of chemical libraries for molecules capable of inhibiting or activating PARG enzymatic activity. The screening may be conducted using any assay for PARG known to those skilled in the art. In a preferred embodiment, the screen may be conducted using the TLC based assay described by Ménard, et al. (26). A known amount of PARG will be incubated under standardized conditions with [$^{32}$P]-poly(ADPR) in the presence of inhibitor or activator. After an appropriate period of time, the reaction will be stopped and the reaction mixture separated on PEI-F cellulose TLC plates. The TLC plates may be developed in an appropriate solvent system such as methanol followed by 0.3N LiCl. The amount of ADPR released in the reaction will be quantified and the effect of the inhibitor or activator on enzymatic activity will be determined. Typical reaction conditions are 50 mM potassium phosphate (pH 7.5) at 37° C. in the presence of 25 $\mu$M [$^{32}$P]-poly(ADPR). The concentration of the inhibitor or activator can be varied as necessary to determine the $K_i$ value of the inhibitor or activator according to standard procedures.

Another embodiment of the invention is directed to a method of altering the response of the cell to a genotoxic stress by modulating the concentration of ADPR polymers. As discussed above, the metabolism of ADPR polymers is critical in determining the fate of cells subjected to genotoxic stress. The modulation can be either an increase or a decrease in the concentration of the polymers. In one embodiment of the present invention, the concentration of ADPR polymers can be decreased by the use of a gene therapy vector expressing a high level of PARG. In another embodiment of the present invention, the concentration of polymers can be increased by inhibiting the enzymatic activity of the PARG enzyme by the addition of inhibitors or activators identified as described above. Alternatively, the concentration of ADPR polymers can be increased by interfering with the endogenous expression of PARG enzymes using antisense oligonucleotide technology.

Knowledge of the nucleotide sequence of the PARG gene permits the preparation of antisense therapeutics containing sequences complimentary to the mRNA of PARG genie. The preparation and delivery of antisense therapeutics is well known to those skilled in the art. For example, antisense therapeutics have been used to treat neoplastic disorder as exemplified by Smith, U.S. Pat. No. 5,248,671, specifically incorporated herein by reference. Additional examples of antisense therapeutics are provided by Miller, U.S. Pat. Nos. 4,511,713 and 4,757,055, specifically incorporated herein by reference.

In the present invention, an oligonucleotide having a sequence complimentary to the mRNA of the PARG gene will be prepared. Such an oligonucleotide is said to be an antisense oligonucleotide with respect to the PARG gene. The oligonucleotide may be RNA or DNA or a may contain both RNA and DNA portions. The oligonucleotide may contain modified bonds so as to enhance the stability of the oligonucleotide and render it more resistant to the action of cellular nucleases. For example, the oligonucleotide may be constructed with phosphorothioate nucleotides, phosphonate nucleotides and other types of modified nucleotides known to those skilled in the art. The structure of the oligonucleotide may be altered so as to include other types of bonds that do not naturally occur in oligonucleotides. For example, adjacent nucleosides might be joined using linear alkyl chains, peptide bonds or other types of structures. The only limitation is that the resulting oligonucleotide remains capable of hybridizing to the target PARG mRNA.

The antisense oligonucleotides may be delivered by any means customarily used in the art. For example, the oligonucleotide may be delivered in neutral liposomes, cationic liposomes or by ballistic high speed injection. Alternatively the DNA sequence encoding the antisense oligonucleotide may be inserted into a gene vector and the vector may be introduced into target cells. The vector may be any type of gene therapy vector known to those skilled in the art. Preferred embodiments include, plasmid vectors and viral vectors. Viral vectors are seen to include those vectors customarily used for gene therapy applications including, but not limited to, retroviral vectors, vaccinia virus vectors, herpes virus vectors, adenovirus vectors and adeno-associated virus vectors. Upon introduction of the vector into target cells, the vector will direct expression of a nucleic acid molecule comprising the appropriate sequence to hybridize with the mRNA encoding a PARG enzyme. In a preferred embodiment, introduction of the vector into the target cell will result in the production of an RNA molecule that hybridizes with the mRNA of a PARG enzyme and also includes one or more additional RNA sequences capable of functioning as a ribozyme. The ribozyme portion of the molecule will cause the cleavage of the mRNA encoding the PARG enzyme thereby preventing the production of PARG.

Therapeutics of this type may be used to treat a wide variety of conditions. In one embodiment, an antisense therapeutic will be used to treat neoplastic disorder. In a preferred embodiment, an antisense therapeutic of the present invention will be delivered in combination with a currently known chemotherapeutic agent. In general, chemotherapeutic agents function by disrupting the integrity of DNA in target cells. Since the recovery of a cell from such DNA disruption is highly dependent upon the normal ADPR polymer metabolism, the presence of the antisense therapeutic will have the effect of chemosensitizing the neoplastic cells by disturbing the ratio PARG and PARP.

In another preferred embodiment, the antisense oligonucleotides of the present invention may be used to treat a variety of conditions caused by genotoxic oxidative stress. Examples include cardiac disorders, neuronal disorders, reperfusion injury, neurotoxicity, Alzheimer's disease, Huntigton's disease and Parkinson's disease. It has been shown that inhibition of ADPR polymer synthesis provides protection against cellular damage caused by nitric oxide injury. Zhang, et al,. U.S. Pat. No. 5,587,384, specifically incorporated herein by reference, teach that decreasing the amount of ADPR polymers formed can result in protection against nitric oxide induced neurotoxicity. As discussed above, decreasing the amount of ADPR polymers in the cell can be accomplished by the introduction of gene therapy vector expressing PARG, thus, the present invention can be used to treat neurodegenerative conditions resulting from oxidative stress.

CONCLUSION

The synthesis and rapid turnover of ADP-ribose polymers is an immediate cellular response to DNA damage. Reported here is the isolation and characterization of cDNAs encoding various poly(ADP-ribose) glycohydrolase (PARG) enzymes responsible for ADP-ribose polymer turnover. PARG was isolated from bovine thymus, yielding a protein of approximately 59 kDa. Based on the sequence of oligopeptides derived from the enzyme, polymerase chain reaction products and partial cDNA clones were isolated and used to construct a putative full-length cDNA. The cDNA of approximately 4.1 kb pairs predicts expression of a protein of approximately 111 kDa, nearly twice the size of the isolated protein. A single transcript of approximately 4.3 kb pairs is detected in bovine kidney poly(A)$^+$RNA, consistent with expression of a protein of 111 kDa. Expression of the cDNA in *Escherichia coli* results in an enzymatically active protein of 111 kDa and an active fragment of 59 kDa. Analysis of restriction endonuclease fragments from bovine DNA by Southern hybridization indicate that PARG is encoded by a single copy gene. Taken together, the results indicate that previous reports of multiple PARGs can be explained by proteolysis of an 111-kDa enzyme. The deduced amino acid sequence of the bovine PARG shares little or no sequence similarity with differing types of known proteins; however, it contains a putative bipartite nuclear location signal as would be predicted for a nuclear protein. The availability of cDNA clones for PARG should facilitate structure-function studies of the enzyme and its involvement in cellular responses to genomic damage.

Other embodiments and advantages of the invention are set forth, in part, in the description that follows and, in part, will be obvious from this description and may be learned from practice of the invention.

EXAMPLES

Example 1
Purification of bovine PARG.

PARG was purified from bovine thymus tissue (Pel-Freez, Rogers, AK) by modifications of previously published procedures (27). The enzyme was isolated up to the polyethylene glycol (PEG)-6,000 fractionation step as described previously (28). However, DNA-agarose and heparin-Sepharose chromatographic steps used previously were omitted, and the PEG-6,000 fraction was applied directly to an affinity matrix of poly(ADP-ribose)-dihydroxyboronyl-Sepharose (PADPR DHB-Sepharose). The active fractions eluted from PADPR DHB-Sepharose (25 ml) were pooled, placed in dialysis tubing, concentrated against dry PEG-20,000 to approximately 12 ml, and dialyzed against 2 liters of 20 mM potassium phosphate buffer, pH 8.0, 0.1% Triton X-100, 5 mM β-mercaptoethanol, 0.1 mM thioglycolic acid, 0.4 M KCl (buffer A). The sample was loaded onto a 1.0×11-cm Toyopearl AF-Red (Supelco) column, and PARG was eluted with an 80-ml linear gradient of 0.4–2 M KCl in buffer A. The active fractions, eluting at approximately 1.25 M KCl, were pooled, placed in dialysis tubing, concentrated against solid sucrose to approximately 9 ml, and dialyzed against 20 mM potassium phosphate buffer, pH 7.2, 0.75 M KCl, 0.1% Triton X-100, 10% glycerol, 5 mM β-mercaptoethanol, 0.1 mM thioglycolic acid. PARG activity was determined as described by Ménard and Poirier (29), and protein content was determined by the method of Bradford (30). The final preparation was quantified by SDS-PAGE (31) and Coomassie Blue staining to compare the intensity of the protein band with a known amount of bovine serum albumin (32).

Figure 2:
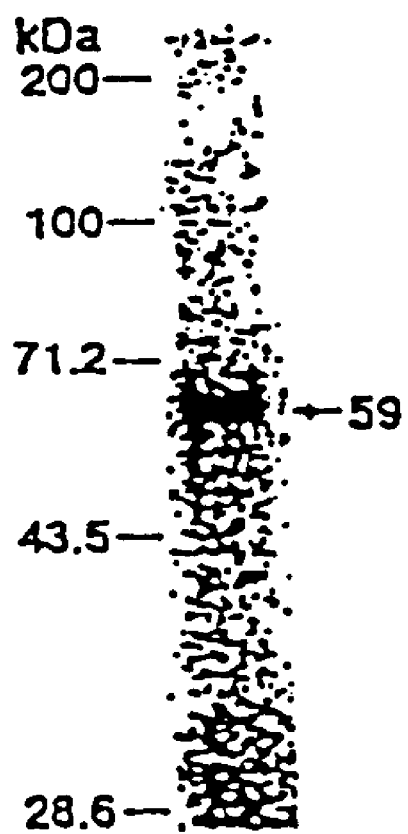
FIG. 2 depicts the SDS-PAGE analysis of purified bovine thymus PARG.

The purification procedure for the bovine thymus PARG summarized in Table 1 is typical for results obtained from six separate preparations of the enzyme. Purification from 500 g of bovine thymus achieved approximately 50,000-fold purification and yielded approximately 20 µg of purified protein. An aliquot of the purified enzyme was precipitated with trichloroacetic acid, washed with acetone, resuspended in SDS-PAGE sample buffer, separated on a 10% SDS-PAGE gel and stained with Coomassie Blue. Analysis of the final preparation of SDS-PAGE revealed that more than 95% of the protein migrated at an apparent molecular mass of approximately 59 kDa (FIG. 2). In FIG. 2, an aliquot of the purified enzyme was precipitated by TCA, washed with acetone, resuspended in SDS-PAGE sample buffer, separated on a 10% SDS-PAGE gel and stained with Coomassie blue. The positions of molecular weight marker proteins are shown.

TABLE 1

Purification of PARG from bovine thymus

| Step | Protein mg | Total activity units | Specific activity units/mg protein | Yield % | Purification -fold |
|---|---|---|---|---|---|
| Crude extract | 27,800 | 57,400 | 2.06 | 100 | 1.0 |
| Protamine sulfate | 12,500 | 58,000 | 4.64 | 101 | 2.3 |
| Ammonium sulfate | 4,480 | 30,000 | 6.70 | 52 | 3.3 |
| CM-Sepharose | 171 | 19,100 | 112 | 33 | 55 |
| PEG 6000 | 23.0 | 7,530 | 327 | 13 | 160 |
| PADPR-DHB-Sepharose | 1.30 | 6,730 | 5,180 | 12 | 2,500 |
| Toyopearl AF-Red | 0.023 | 2,260 | 98,300 | 4 | 48,000 |

Example 2
Peptide Sequencing.

Prior to proteolytic fragmentation, the purified bPARG (40 µg in 100 µl of 0.4 M ammonium bicarbonate buffer, pH 8.0, 8 M urea) was incubated in a final concentration of 2.2 mM dithiothreitol at 56° C. for 15 min. Iodoacetamide was added to a final concentration of 2.0 mM, and the sample was incubated at 25° C. for 15 min. After dilution with an equal volume of water, 1.5 units of immobilized L-1-tosylamido-2-phenylethyl chloromethyl ketone-treated trypsin (Pierce Chemical, Rockford, Ill.) was added, and the sample was incubated at 37° C. for 18 h with gentle rotary shaking. Finally, the mixture was subjected to centrifugation at 16,000×g for 5 min to separate the tryptic fragments from the immobilized trypsin. The tryptic fragments were adjusted to 0.05% in trifluoroacetic acid and separated on a 4.6 mm×25 cm, Microsorb MV, $C_4$ reversed-phase HPLC column (Rainin) eluted with an 80-min linear gradient from 4 to 44% acetonitrile in 0.05% trifluoroacetic acid. Four oligopeptide fractions, with approximate elution times of 61, 63, 68, and 75 mm, were selected for peptide sequence analysis by the Edman degradation method. Amino acid sequence data of four oligopeptides, designated by their approximate HPLC elution times from the reversed-phase column, are shown in Table II.

TABLE II

Amino acid sequence of oligopeptides derived from bPARG

| Oligopeptide | Amino Acid Sequence | | | SEQ ID NO: |
|---|---|---|---|---|
| | 10 | 20 | 30 | |
| 68 | LFTEVLDHNE | CLIITGTEQY | SEYTGYAETY R | SEQ ID NO: 11 |
| 63 | AYCGFLRPGV | SSENLSAVAT | GNXGCGAFG | SEQ ID NO: 12 |
| 61 | FLINPELIVS | R | | SEQ ID NO: 13 |
| 75 | IALXLPNIXT | QPIPLL | | SEQ ID NO: 14 |

Example 3 cDNA Cloning.

Figure 3:
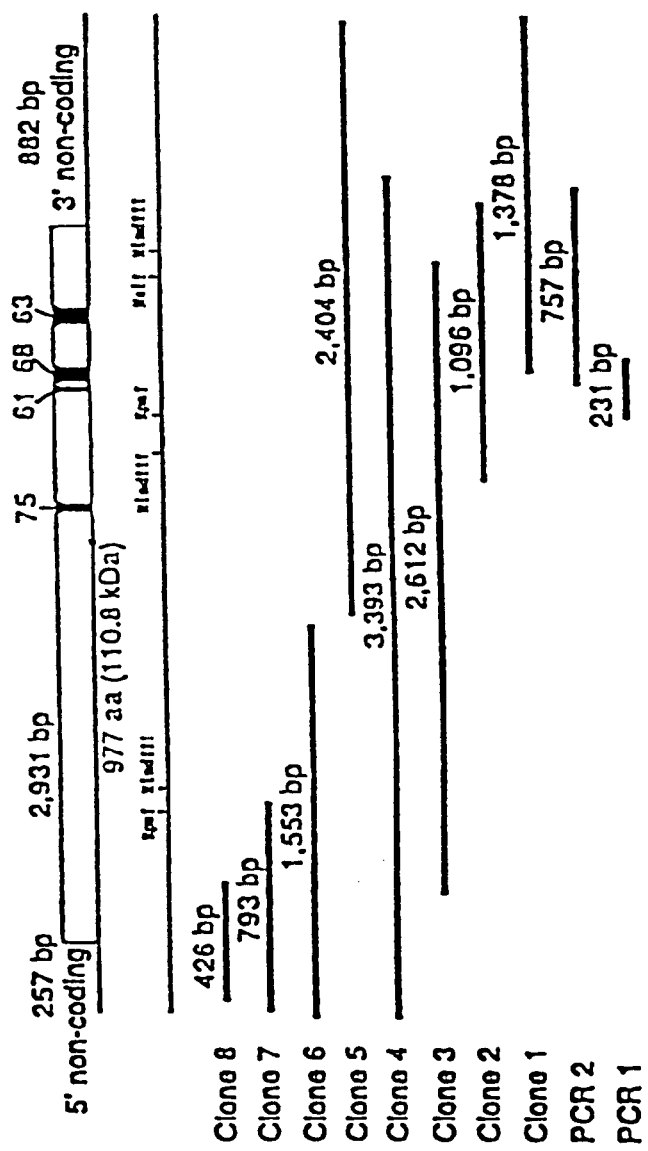
FIG. 3 depicts the alignment of the DNA sequences of two PCR products and eight λgt11 cDNA clones used to identify the cDNA coding for bovine PARG.

To obtain cDNA clones encoding bovine PARG, PCR amplification experiments were followed by the screening of two different bovine cDNA libraries. FIG. 3 depicts the alignment of the DNA sequences of two PCR products and eight λgt11 cDNA clones used to identify the cDNA coding for bovine PARG. The two PCR products and clones 1 and 2 were obtained from the bovine thymus cDNA library. Clones 3–8 were obtained from the bovine kidney cDNA library. The positions of restriction sites used in this study are shown, and the top diagram shows the consensus clone, denoting the relative location of the coding regions for oligopeptides, 75, 61, 68, and 63 as well as the open reading frame and noncoding regions. For each of the cDNA inserts characterized, the sequence of both strands was determined by the dideoxynucleotide chain termination method using Sequenase™ (U.S. Biochemical Corp., Cleveland, Ohio).

The first step leading to the isolation of cDNA clones was to synthesize two multi-degenerate 17-mer primers, GAY-CAYAAYGARTGYYT (SEQ ID NO: 15) and CKRTANG-TYTCNGCRTA (SEQ ID NO: 16) (where Y represents T/C, R is A/G, K is T/G, and N is A/T/C/G), based on two regions of the SEQ ID NO: 11; "DHNECL" (amino acids 7 to 12 of SEQ ID NO: 11) and "YAETYR" (amino acid 26 to amino acid 31 of SEQ ID NO: 11) (Table II). Using the multidegenerate primers and an oligo(dT)-primed bovine thymus cDNA λgt11 library BL1019b from Clontech (Palo Alto, Calif.), PCR amplification generated a 74-bp DNA fragment with a deduced amino acid sequence identical to the corresponding region of oligopeptide 68. Next, two specific 24-mer oligonucleotide primers, ATCATCACAGGTACT-GAGCAGTAC (SEQ ID NO: 17) and GCCTGTGTAT-TCACTGTACTGCTC (SEQ ID NO: 18), based on the sequence of this 74-bp DNA were used in combination with λgt11 forward and reverse primers to amplify PCR products 1 and 2 from the bovine thymus library. PCR product 1 contained 231 bp of sequence including the region encoding the N-terminal region of oligopeptide 68 (SEQ ID NO: 11) and the entire sequence of oligopeptide 61 (SEQ ID NO: 13). PCR product 2 contained 757 bp, which included a sequence encoding the C-terminal region of oligopeptide 68 (SEQ ID NO: 11) and the entire sequence of oligopeptide 63 (SEQ ID NO: 12).

The sequence information obtained from PCR products 1 and 2 was used to isolate cDNA clones obtained by the screening of bovine thymus and bovine kidney cDNA libraries. A 518-bp EcoRI-HindIII fragment from PCR product 2 was used as a probe to screen approximately 1×10⁶ independent clones from the bovine thymus library. Two positive cDNA clones (clones 1 and 2) were isolated, which overlapped PCR products 1 and 2. However, attempts to obtain clones from the bovine thymus library that contained sequence 5' to clone 2 were unsuccessful. Thus, a 231-bp EcoRI-KpnI fragment from clone 2 was used as a probe to screen approximately 5×10⁵ independent clones of the bovine kidney 5' stretch plus cDNA λgt11 library BL300 lb (Clontech, Palo Alto, Calif.). Three positive cDNA clones (clones 3–5) were obtained, all of which contained sequence 5' to clone 2. Each of these clones also contained a sequence encoding oligopeptide 75. Clones 1–5 provided multiple overlapping sequences in the 3'-terminal portion of a consensus cDNA, but additional clones were sought to obtain overlapping sequences for the 5'-terminal region. Thus, a 436-bp EcoRI-KpnI fragment located at the 5' end of clone 3 was used as a probe to screen approximately 6×10⁵ independent clones of the bovine kidney library. Clones 6–8 provided overlapping sequences for the 5'-terminal region. The full-length cDNA was constructed by ligating a 3.9-kb XbaI-NsiI fragment from pWL11 (clone 1 cDNA insert in pTZ18R (33)) and a 3.0-kb NsiI-XbaI fragment from pWL13 (clone 4 cDNA insert in pTZ18R). The resulting plasmid, termed pWL30, contained the 4,070-bp full-length cDNA.

FIG. 3 shows an alignment of the DNA sequences of two PCR products and eight λgt11 cDNA clones used to identify the cDNA coding for bovine PARG. The two PCR products and Clones 1 and 2 were obtained from the bovine thymus cDNA library. Clones 3 through 8 were obtained from the bovine kidney cDNA library. The position of restriction sites used in this study is shown and the top diagram shows the consensus clone, denoting the relative location of the coding regions for oligopeptides 75, 61, 68, and 63 as well as the open reading frame and non coding regions.

The nucleotide sequence of cDNA coding for bovine PARG is shown in the sequence listing as SEQ ID NO: 1. The deduced amino acid sequence of the enzyme is shown in the sequence listing as SEQ ID NO: 2. The four oligopeptides sequenced from purified enzyme is within SEQ ID NO:

2. They are IALCLPNICTQPIPLLK (amino acid 601 to 617, SEQ ID NO: 2); LINPELIVSR (amino acid 761 to 770, SEQ ID NO: 2); LFTEVLDHNECLIITGTEQYSEYTGYA-ETYR (amino acid 771 to 801, SEQ ID NO: 2) and AYCGFLRPGV PSENLSAVAT GNWGCGAFGGDAR (amino acid 849 to 880, SEQ ID NO: 2). The combined nucleotide sequence of Clones 1 through 8 predicted a full-length cDNA clone of 4,070 bp containing 257 bp of 5'-non-coding sequence, a single open reading frame of 2,931 bp (beginning at the ATG at position 258 of SEQ ID NO: 1) and a 3'-non-coding region of 882 bp. and the deduced amino acid sequence which predicts a protein of 977 amino acids and a molecular weight of 110.8 kDa.

Example 4

Analysis of the sequence of bovine PARG.

Figure 4:
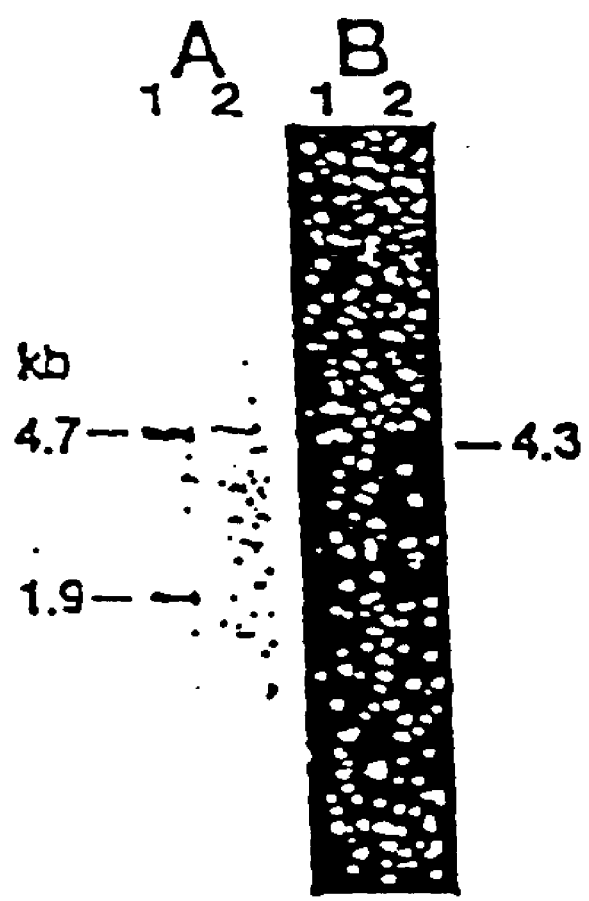
FIG. 4 depicts a northern blot analysis of bovine kidney cells mRNA transcripts.

The cDNA clone (SEQ ID NO: 1) has features typical of cDNAs that code for mammalian proteins. These include (i) an oligo A (putative poly(A)+) sequence at the 3'-end, (ii) a polyadenylation signal (AATAAA) 12 bp upstream from the oligo A sequence, (iii) a sequence of ATTTA in the 3'-untranslated region thought to play a role in selective mRNA degradation in mammalian cells (34), (iv) a single open reading frame, and (v) a nucleotide sequence around the first start codon commonly found at known sites of initiation of translation (35). The evidence that the cDNA clone constructed represents a full-length or nearly full-length clone for PARG is shown by the observation that hybridization of poly(A)+RNA from bovine kidney cells with the cDNA showed a single band of hybridization of approximately the same size as the cDNA under stringent hybridization conditions (set forth above) (FIG. 4).

The nucleotide sequence encoding bovine PARG indicates that PARG shares little or no sequence similarity with other known sequences. A search of sequence data banks has failed to reveal significant sequence similarity with any sequences coding for known proteins. A strong sequence similarity has been observed with human and rat cDNA clones that likely represent partial clones for PARG from these species. Examination of protein sequence databases such as Genbank and SwissPro also has shown that the deduced amino acid sequence of PARG lacks any sequence similarity with known proteins. However, the amino acid sequence shares a significant similarity with a protein sequence from *Caenorhabditis elegans* that may represent the PARG protein from this organism (36).

The deduced amino acid sequence of PARG has been examined for a number of structural motifs that can be predicted from the primary amino acid sequence. The expressed PARG protein was observed to be able to form dimers stable to SDS-PAGE conditions. In that regard, residues 871–907 show significant homologies to known leucine zipper dimerization sequences (37).

Another motif identified is a putative bipartite nuclear location signal (NLS) (38). It is interesting that PARP also contains a bipartite NLS (39). FIG. 5 compares deduced amino acid sequences in the NLS region of the bovine PARG, and regions of putative PARG sequences from human, mouse and *C. elegans*, with the NLS region of PARP from seven different organisms. Conserved residues are noted in bold and the amino acid distances are from the amino terminal methionine residue. Abbreviations and references for the sequences shown are as follows: bPARG, bovine PARG (SEQ ID NO: 19); hPARG, human PARG (SEQ ID NO: 20); mPARG, murine PARG (SEQ ID NO: 21); CePARG, *Caenorhabditis elegans* PARG (SEQ ID NO: 22); hPARP, human PARP (SEQ ID NO: 23; 40); mPARP, murine PARP (SEQ ID NO: 24; 41); bPARP, bovine PARP (SEQ ID NO: 25, 42); aPARP, chicken PARP (SEQ ID NO: 26; 43); V1PARP, *Xenopus laevis* PARP (SEQ ID NO: 27; 44); DmPARP, *Drosophila melanogaster* PARP (SEQ ID NO: 28; 45); SpPARP, *Sarcophaga peregrina* PARP (SEQ ID NO: 29; 46). In FIG. 5, conserved residues are noted in boldface type, and the amino acid distances are from the amino-terminal methionine residue. Sequence alignment of putative bipartite nuclear localization signal of bovine, human and murine PARG compared to the nuclear localization signal of PARP from different organisms. The putative NLS of PARG fulfills the criteria for bipartite NLS in that it contains conserved acidic and basic amino acid residues at two different locations each within the region of sequence similarity to the NLS of PARP (47).

Figure 6:
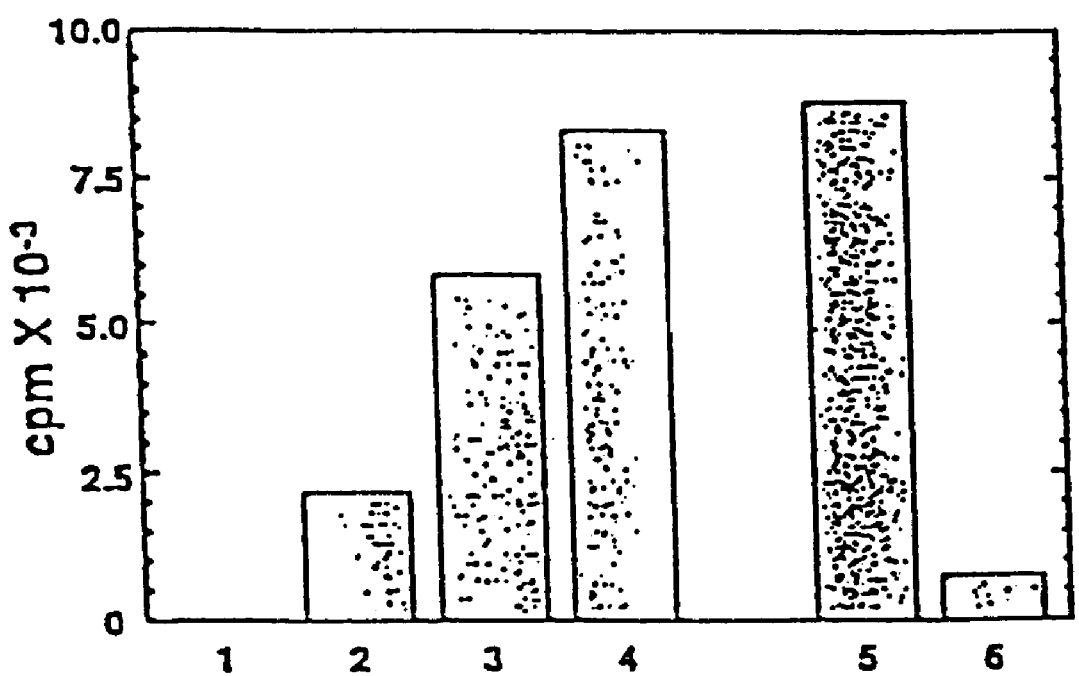
FIG. 6 depicts expression of bPARG enzyme activity in *E. coli* (10).

A surprising finding was that the bovine PARG cDNA clone codes for a protein of approximately 111 kDa, which is nearly twice the size of the PARG protein isolated from bovine thymus (FIG. 2). It indicates that PARG contains a protease sensitive site that, following proteolysis, yields a protein fragment of approximately 59 kDa that still retains enzymatic activity. Several pieces of evidence favor this possibility. (i) Expression of the carboxyl terminal portion of the cDNA resulted in enzymatic activity (FIG. 6, bar 5). (ii) All of the oligopeptides sequenced were located in the carboxyl terminal half of the protein (FIG. 3, FIG. 6 and Table 2). (iii) The only protein, other than 59 kDa protein detected in the thymus preparation was approximately 111 kD (FIG. 2). (iv) The PARG activity expressed in bacteria was sensitive to proteolysis, yielding a protein of approximately 56 kD (FIG. 6). (v) The cleavage site in PARG is in the region of the putative NLS and the PARP NLS is located in a protease sensitive site (48). Taken together with the data suggesting that bovine PARG appears to be coded for by a single copy gene (FIG. 7), proteolysis seems likely to explain the presence of PARG activity of molecular weight of approximately 74 kDa and 59 kDa in bovine thymus preparations (49). Likewise, a similar mechanism could explain previous reports of a PARG of 74 kDa isolated from nuclear fractions of guinea pig liver and human placenta (50) and a PARG of 59 kDa isolated from postnuclear fractions of guinea pig liver (51).

While proteolysis of a larger protein to yield smaller proteins retaining PARG activity seems likely to explain the size heterogeneity of PARG previously reported, it remains to be determined if proteolysis normally occurs in vivo or whether it occurs during purification of the enzyme. While the results presented here show that a full-length protein can be expressed containing PARG activity (FIG. 8), the molecular size of PARG in vivo also remains to be determined. If PARG occurs as a larger protein, an interesting possibility is that the amino terminal region may be involved in the regulation of enzymatic activity.

Example 5

Expression of bPARG in Escherichia coli.

To determine whether the isolated cDNA encoded PARG, bPARG was express using two different bacterial expression systems, the pTrcHis Xpress System™ (Invitrogen, Carlsbad, Calif.), in which the expressed protein contains a leader polyhistidinie sequence, and the glutathione S-transferase (GST) gene fusion system (Pharmacia Biotech Inc., Piscataway, N.J.). For expression in the pTrcHis Xpress system, three different DNA fragments were amplified and inserted into the pTrcHis expression plasmid. Constructs A and B contained the entire opening reading frame of 110.8 kDa, which together with the fusion partner predicted a protein of about 115 kDa. Construct B also contained the 3'-untranslated region of the clone. Construct A, containing the cDNA sequence-3 to 2,946, was prepared by subcloning a 2.9 kb XhoI-EcoRI DNA fragment amplified from pWL30 with primers WIN34 (GCTGCGGGTCTCGACGATG AGTGCGGGC) (SEQ ID NO: 30) and WIN15 (GCGTCTAGAATTCACTTGGCTCCTCAGGC) (SEQ ID NO: 31). Construct B, containing the cDNA sequence-3 to 3,813, was prepared by subcloning a 3.8-kb XhoI-EcoRI DNA fragment amplified from pWL30 with primers WIN34 (SEQ ID NO: 30) and WIN33 (CCGGAATTC GGGTTTTTTGTTAATGAAAATTTATTAAC) (SEQ ID NO: 32). Construct C, containing cDNA sequence 964–2, 946, was prepared by subcloning a 2.0-kb DNA fragment amplified from pWL13 with primers WIN14 (TCAGAGCAGATGAACTCGAGCAGTCCAGG) (SEQ ID NO: 33) and WIN15 (SEQ ID NO: 31). Since the isolated PARG of approximately 59 kDa contained enzymatic activity, construct C contained only the 75-kDa carboxyl-terminal region of the PARG, which predicted a fusion protein of approximately 79 kDa.

For expression experiments of bPARG as a GST fusion protein, an insert containing the cDNA sequence from position 1138 to 2946 was prepared by subcloning, a 1.8-kb EcoRI-EcoRI fragment amplified from pWL30 with the oligonucleotide CCAATTTGAAGGAGGAA TTCCCGC-CGCCACCATGAATGATGTGAATGC-CAAACGACCTGGA (SEQ ID NO: 34) and WIN15 (SEQ ID NO: 31) as primers. The resulting DNA fragment was inserted into the EcoRI site of the pGEX-2T expression vector, and the plasmid was used to transform E. coli NM522 cells.

For expression experiments, bacterial cultures were grown at 37° C. in 1% Bacto-tryptone, 0.5% yeast extract, and 0.5% NaCl to a density of approximately 0.6 $A_{600}$/ml and were induced with 1 mM isopropyl-β-D-thiogalactoside (IPTG). Cells were collected by centrifugation, and crude extracts were prepared by sonication (10 $A_{600}$/ml) in 10 mM sodium phosphate buffer, pH 7.2, 150 mM NaCl, 0.5 mg/ml lysozyme, 0.1 mg/ml phenylmethylsulfonyl fluoride, 1 mM EDTA, 0.7 µg/ml pepstatin A, 0.5 µg/ml leupeptin, and 1 µg/ml aprotinin. Cell extracts were subjected to centrifugation, and the supernatant fraction was used for assay. PARG assay conditions were as described previously (52). Following incubations, portions of reaction mixture were analyzed by thin layer chromatography or subjected to anion exchange HPLC.

Using a thin layer chromatography assay that measures release of [$^{32}$P]ADP-ribose from [$^{32}$P]ADP-ribose polymers (53), PARG activity was detected in extracts from cells transformed by each of the constructs. FIG. 6 shows results obtained with constructs B and C. Reaction mixtures contained approximately 15,000 cpm of [$^{32}$P]ADP-ribose polymers, and the cpm shown represent ADP-ribose released from the ADP-ribose polymers. Bar 1, a strain transformed by pTrcHis without an insert but induced with 1 mM IPTG for 5 h at 37° C. A strain containing construct B is shown without the addition of IPTG (bar 2) or after the addition of 1 mM IPTG for 1.5 h (bar 3) or 5 h (bar 4). A strain containing construct C 5 h after induction by IPTG is shown in the absence (bar 5) and presence (bar 6) of 167 µm ADP-hydroxymethylpyrrolidine diol (54). No activity was detected in cells transformed with the empty vector, but activity was detectable without induction by IPTG, indicating a leaky lac promoter. The addition of IPTG resulted in a time-dependent increase of up to approximately 4.5-fold in enzymatic activity. FIG. 6 also shows that the enzymatic activity was strongly inhibited by the presence of ADP-hydroxymethylpyrrolidine diol, a specific inhibitor of PARG (55).

Figure 9:
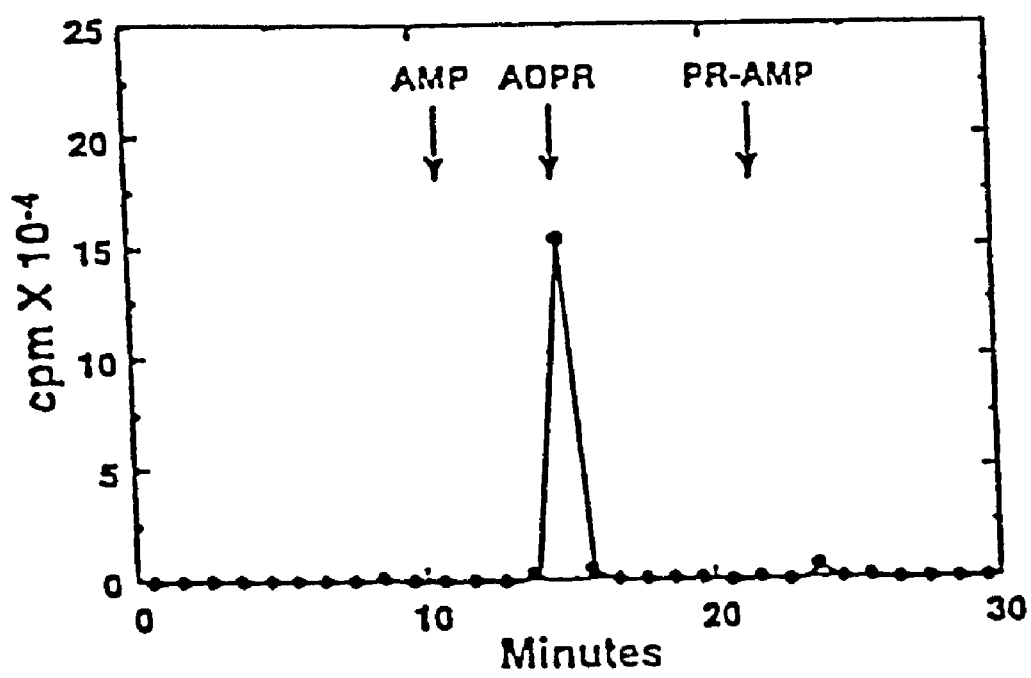
FIG. 9 depicts the analysis by anion exchange HPLC of material released from ADP-ribose polymers by PARG action.

In FIG. 9, material released from ADP-ribose polymers by anion exchange HPLC was analyzed. Extracts from a strain containing construct B were incubated with [$^{32}$P]ADP-ribose polymers (56), and a portion was analyzed by anion exchange HPLC as described. The elution times for AMP, ADPR, and PR-AMP are indicated by arrows. The material analyzed was PARG expressed in E. coli. The results indicated that the material released from ADP-ribose polymers is exclusively ADP-ribose by strong anion exchange HPLC (FIG. 9), demonstrating that the cell extracts did not contain any other ADP-ribose polymer-degrading enzymes such as phosphodiesterase, which catalyzes the formation of AMP and phosphoribosyl-AMP (57).

Anion exchange HPLC utilized a Whatman Partisil SAX column equilibrated with 7 mM potassium phosphate buffer pH 4.0, at a flow rate of 1 ml/min. The sample was diluted in the same buffer, applied to the column, and eluted with a 30-min linear gradient from 7 mM potassium phosphate buffer, pH 4.0 to 250 mM potassium phosphate buffer, 0.5 M KCl, pH 4.0.

Figure 8:
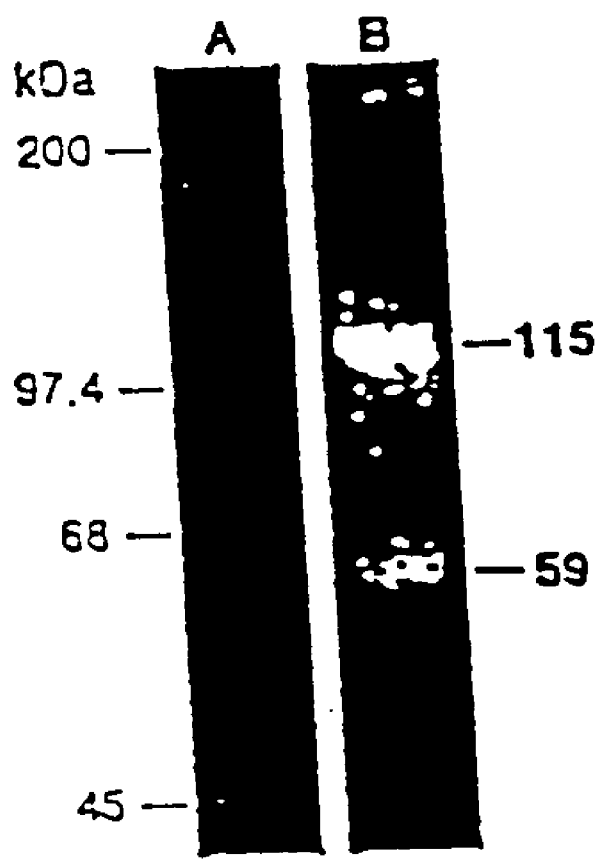
FIG. 8 depicts activity gel autoradiogram of *E. coli* expressed bovine PARG.

To determine the size of the expressed enzymatic activity, an activity gel assay (58) was used. Activity gel assays for bPARG were done by casting polyacrylamide gels with auto modified PARP containing [$^{32}$P]ADP-ribose polymers as described previously (59). Following electrophoresis, PARG was renatured by incubating the gels at 25° C. in 5 volumes of 50 mM sodium phosphate buffer, pH 7.5, 50 mM NaCl, 10% glycerol, 1% Triton X-100, 10 mM β-mercaptoethanol, changing the buffer every 3 h for a total of five changes. After an additional incubation at 37° C. for 3 h, gels were dried, and PARG activity was detected following autoradiography as a clear band on a black background. Cell extracts containing PARG fused to GST were examined for binding to glutathione-Sepharose 4B (GSH-Sepharose) (Pharmacia Biotech Inc.) according to the specifications of the manufacturer. No bands were produced from extracts from the IPTG-induced pTrcHisB vector that did not contain an insert. Extracts from cells transformed with a construct containing a PARG insert showed bands at approximately 115 and 59 kDa (FIG. 8). During storage at 4° C., cell extracts lost activity migrating at the higher molecular weight, while the activity at approximately 59 kDa increased.

Figure 10:
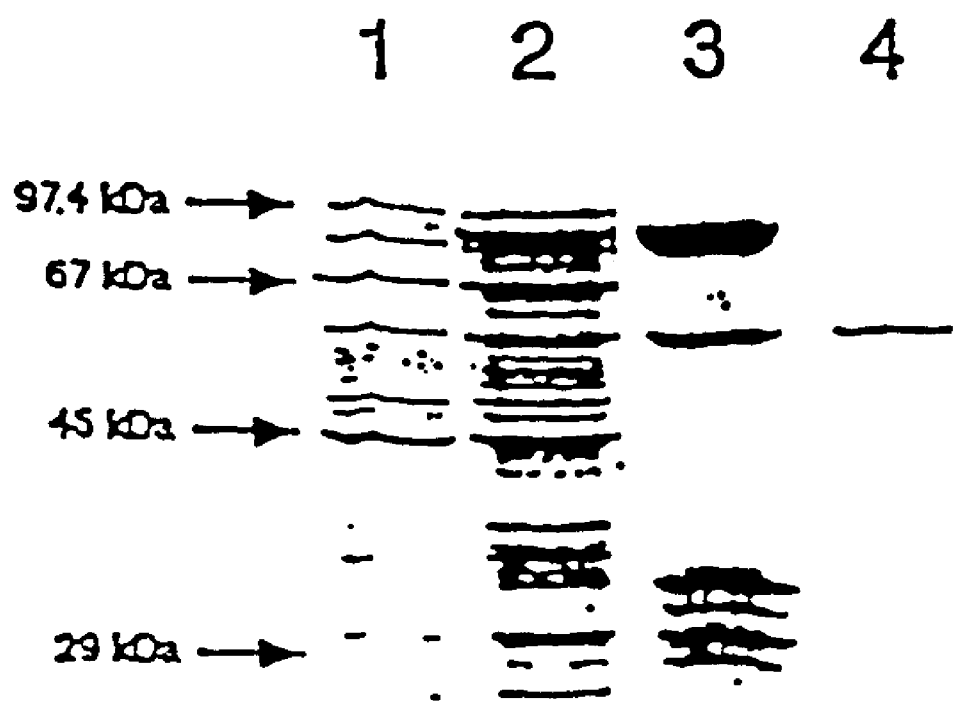
FIG. 10 depicts the SDS-PAGE analysis of the purification of *E. coli* expressed GST-PARG.

Expression of bPARG in the pTrcHisB expression vector did not result in detectable amounts of protein by staining the Coomassie Blue. Thus, another construction was designed to overexpress a 69-kDa carboxyl-terminal region of the PARG as a fusion with GST, which allows convenient protein purification by affinity chromatography on a GSH-Sepharose column. Two hours after induction with IPTG, strong expression of a protein migrating at approximately 90 kDa was observed. This protein bound to GSH-Sepharose and was eluted by GSH. The construct contained a thrombin cleavage site between the GST and the 69-kDa region of PARG, and the treatment of the material bound to GSH-Sepharose with thrombin resulted in the release of a protein that migrated at approximately 59 kDa. This result suggests that the protein purified from the bovine thymus may be larger than suggested by its migration on SDS-PAGE. The result of this experiment is presented in FIG. 10. Lane 1 shows extract from uninduced cells; lane 2 shows extract from cells induced with 1 mM IPTG for 2 hours; lane 3 shows proteins in extracts from cells shown in lane 2 that bound to GSH-Sepharose; lane 4 shows material released from GSH-Sepharose by treatment with thrombin.

Figure 11:
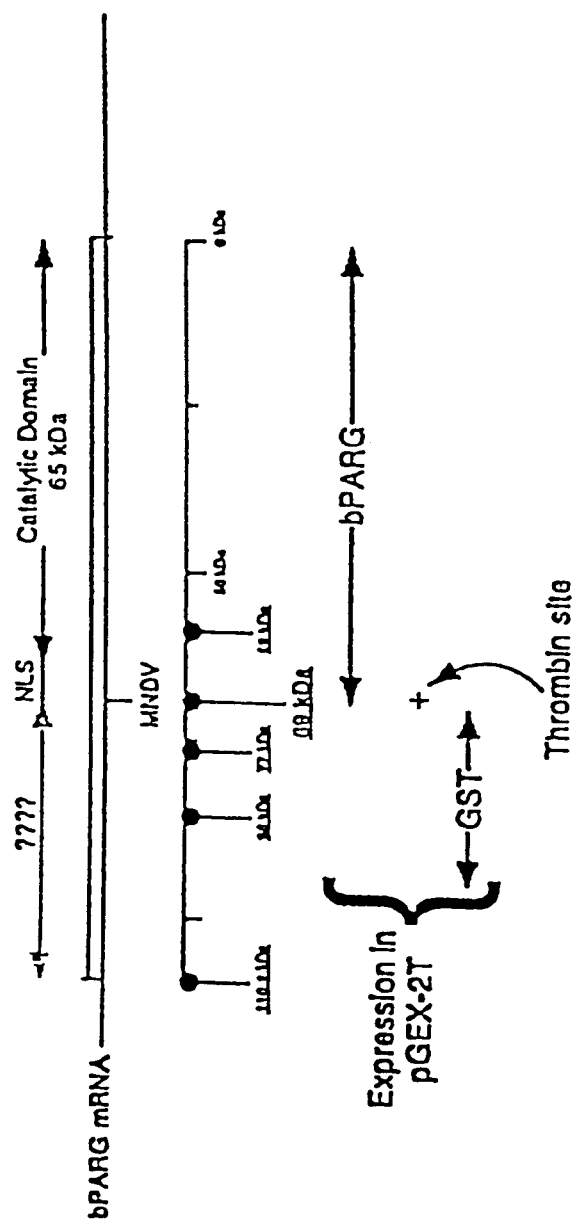
FIG. 11 depicts a schematic representation of the portions of the bovine PARG cDNA expressed as GST fusion constructs.
Figure 12:
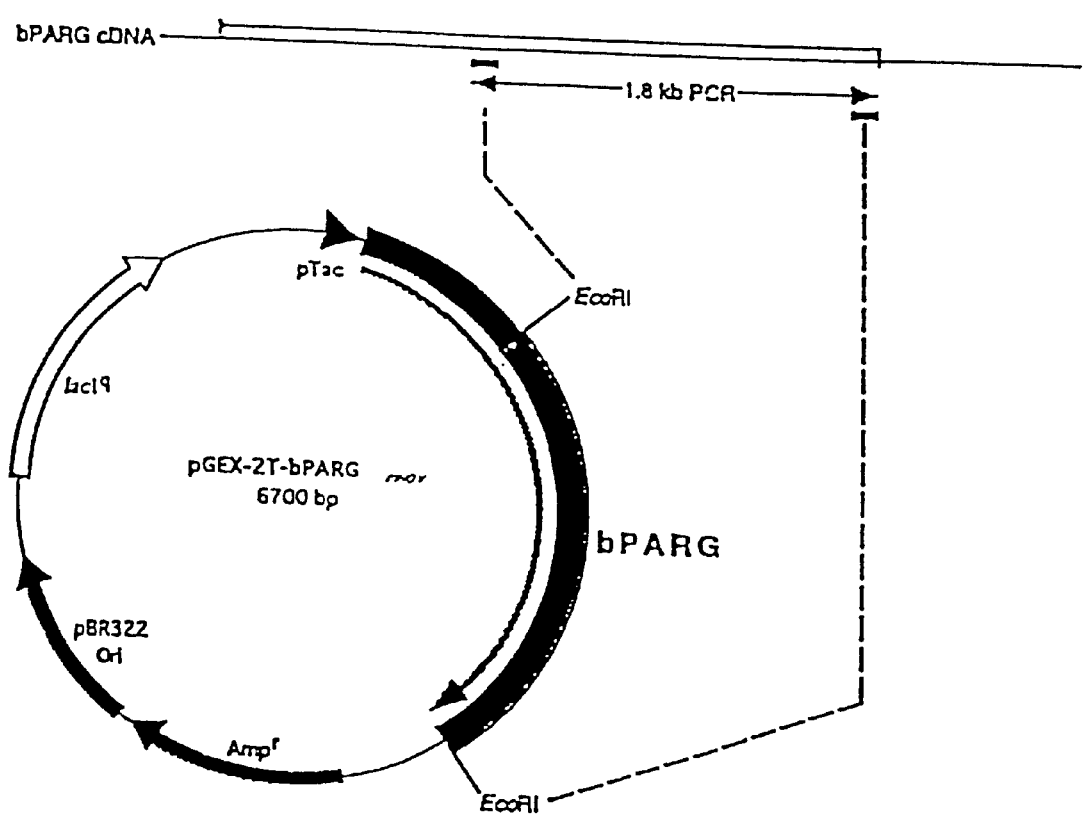
FIG. 12 depicts the cloning of the 1.8 kb PCR EcoRI fragment encoding for the 65 kDa catalytic domain of PARG.

In addition to the GST fusion construct described above, several other GST fusion proteins have been made. FIG. 11 shows the portions of the bovine PARG gene that have been expressed. The top line represents the structure of bovine PARG mRNA containing the open reading frame encoding the 111 kDa PARG protein. The different parts of PARG that have been cloned in expression vectors are represented with the size of the resulting expressed recombinant proteins. The expression of the 65 kDa catalytic domain of PARG (starting at the amino acid MNDV) in pGEX-2T as a fusion protein with glutathione-S-transferase (29 kDa) is detailed. Among the constructs, only the clone designed to express a protein of 69 kDa starting at amino acid+380 from the sequence of bovine PARG (bPARG$_{MNDV}$) allowed high level expression as a fusion protein with glutathione-S transferase (GST). A 1.8 kb PCR EcoRI fragment encoding for the 65 kDa catalytic domain of PARG was cloned into the EcoRI site of pGEX-2T giving pGEX-2T-bPARG$_{MNDV}$. This construction results in the expression of a fused polypeptide consisting of the sequence of GST. Amino acids derived from the polylinker and thrombin site and the 65 kDa domain (FIG. 12).

Figure 13:
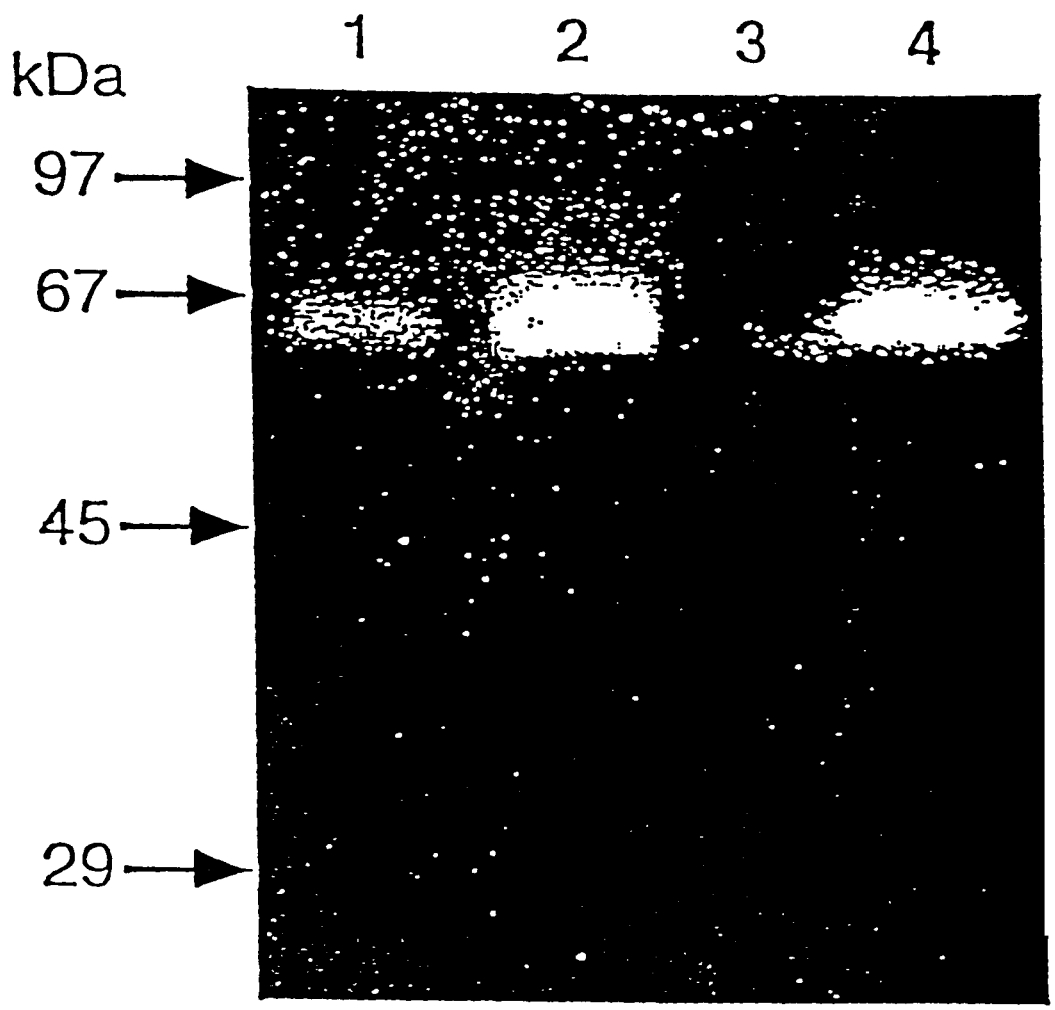
FIG. 13 depicts an autoradiogram of an activity gel of GST-PARG fusion constructs expressed in *E. Coli* and PARG expressed in baculovirus.

In addition to various constructs designed to express PARG in *E. Coli*, a recombinant baculovirus expressing a functional PARG has been constructed using the methodology of Summers and Smith as set out in U.S. Pat. No. 4,879,236 which is specifically incorporated herein by reference.

bPARG$_{MNDV}$ was cloned in baculovirus transfer vector pVL1393 using the EcoRI site. The recombinant vector was constructed as follows. An insert containing the cDNA sequence from position 1138–2946 of bovine PARG was prepared by subcloning a 1.8 kb EcoRI fragment amplified from pWL30 using oligonucleotides CCAATTTGAAG-GAGGAATTCCCGCCGCCACCATGAAT-GATGTGAATGCCAAACG ACCTGGA (SEQ ID NO: 34) and GCGTCTAGAATTCACTTGGCTCCTCAGGC (SEQ ID NO: 31, WIN15). The resulting fragment was inserted into the EcoRI site of the pVL1393 baculovirus transfer vector. The amplification introduced a Kozak consensus sequence (gaattcccgccgccaccATGAA SEQ ID NO: 35) at the start site of translation to enhance expression of the recombinant protein. The resulting recombinant plasmid was cotransfected with linearize Baculogold™ baculovirus DNA (Pharmingen, San Diego, Calif.) into SF9 cells according to the manufacturers instructions. Recombinant viruses isolated using standard techniques. Overexpression of the recombinant protein was confirmed by Western blot and the results displayed in FIG. 13 demonstrate that the 65 kDa domain expressed in *E. coli* contained enzymatic activity (lane 2) migrating with the same apparent molecular weight as the enzyme purified from bovine thymus (lane 1). Likewise, a construct expressing bPARG$_{MNDV}$ domain in SF9 insect cells infected with recombinant baculovirus showed activity (lane 4) migrating with the same apparent molecular weight.

Example 6

Northern Blot Analysis.

An surprising feature of the consensus full-length cDNA clone was that it predicted expression of a protein of approximately 111 kDa (FIG. 3, SEQ ID NO: 1, and SEQ ID NO: 2), while the enzymatically active PARG from thymus had a molecular weight of approximately 59 kDa (FIG. 2). To determine the size of the RNA transcript for PARG, total RNA and poly(A)+RNA were isolated from bovine kidney (MDBK) cells and annealed using Clone 4 as the hybridization probe.

Total cytoplasmic RNA and poly(A)+RNA were isolated from bovine kidney MDBK cells (ATCC #CCL22) using TRIzol reagent (Gibco/BRL) following the manufacturer's recommendations. After the RNA was fractionated, it was then transferred to nylon membranes and hybridized with Clone 4 (FIG. 3) radiolabeled by a random hexamer priming method (21). The results are presented in FIG. 4. Total RNA (5 µg, lanes 1A and 1B) and poly(A)+RNA (4 µg, lanes 2A and 2B) were separated on a denaturing agarose gel (60). Panel A shows the ethidium bromide stained gel and panel B shows the autoradiogram of a Northern blot analysis using a random primed, $^{32}$P-labeled DNA probe constructed from Clone 4 (FIG. 3). A single transcript of approximately 4.3 kb was detected in the poly(A)+RNA (FIG. 4, lane 2). Thus, the transcript size was consistent with the expression of a 111 kDa PARG protein.

Example 7

Southern Blot Analysis of PARG Genomic Complexity.

Previous studies have reported that PARG isolated from nuclear fractions had a molecular weight of approximately 75 kDa (61), while PARG isolated from whole cell homogenates or postnuclear supernatant fractions had a molecular weight of approximately 59 kDa (62). These results suggest that either two or more genes may code for PARG or that proteolysis generates lower molecular weight forms from higher molecular weight forms. The cDNA isolated encoded a protein considerably larger than any PARG proteins previously described, consistent with the possibility that the different forms of PARG are derived from a single form by proteolytic cleavage. To test the hypothesis that PARG is encoded by a single copy gene, the genomic complexity of the PARG gene was analyzed by a Southern hybridization experiment.

Total genomic DNA was prepared from bovine thymus tissue as described previously (63) and DNA (10 µg) was digested with EcoRI, BglII, XbaI or PstI, fractionated on a 1% agarose gel, transferred to a nylon membrane (Hybond N+, Amersham), and hybridized using an 828 bp HindIII fragment of Clone 1 radiolabeled as described for clone 4 above (64). Pre-hybridizations and hybridizations were carried out at 42° C. in 50% formamide, 0.25 M sodium phosphate buffer, pH 7.2, 0.25 M NaCl, 7% SDS, 1 mM EDTA. The blot was annealed with a $^{32}$P-labeled DNA probe corresponding to the carboxyl terminal region of the PARG protein.

Figure 7:
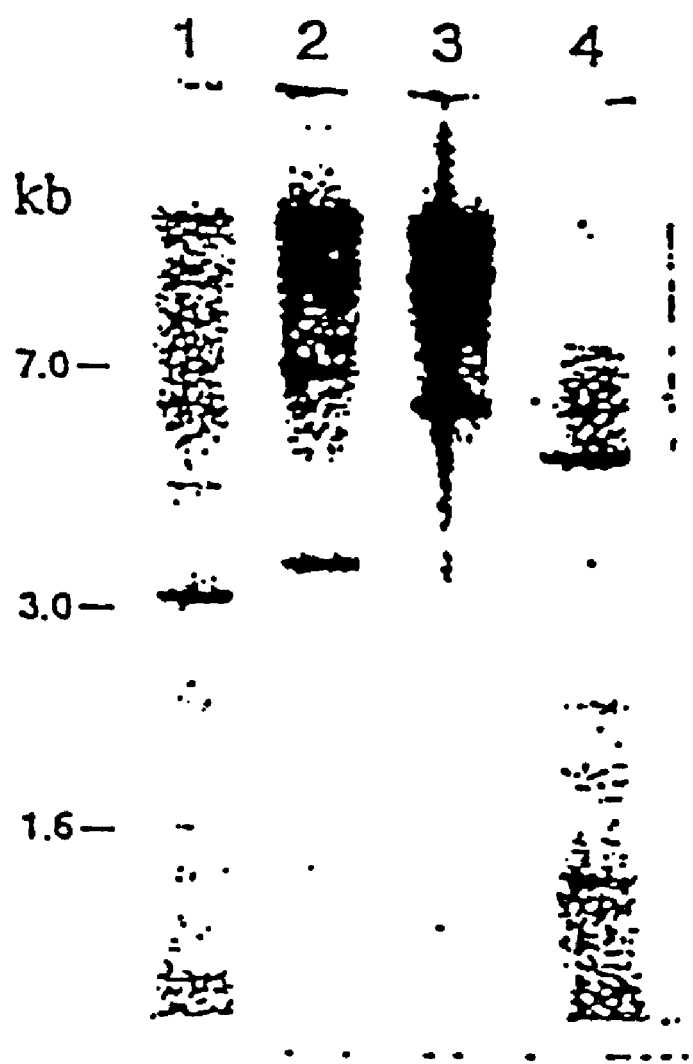
FIG. 7 depicts a Southern blot analysis of bovine DNA probed with PARG cDNA.

The results of the Southern blot analysis are presented in FIG. 7. Genomic DNA was digested with four different restriction enzymes, EcoRI (lane 1), BglII (lane 2), XbaI (lane 3) and PstI (lane 4), none of which cleave within the carboxyl terminal region of the PARG cDNA. Following electrophoresis, the restriction digests were subjected to hybridization with a probe that corresponded to the carboxyl terminal region of the PARG cDNA. The analysis displayed in FIG. 7 shows that, in each restriction digest, the probe hybridized primarily with a single restriction fragment. The fainter signals likely reflect the presence of introns in the PARG gene. This result indicates that PARG is encoded by a single copy gene in the bovine genome.

Example 8

Isolation and Characterization of PARGs from Other Species.

The isolation and characterization of bovine cDNA encoding poly(ADP-ribose) glycohydrolase (PARG) has been described above. Using the information provided by the sequencing of bovine PARG, various tools were used, including public sequence databases searches and screening of cDNA libraries using PARG specific probes, to clone and sequence the cDNA and determine the primary structure of PARG from human, mouse, Drosophila and *Caenorhabditis elegans*. Mammalian sequences newly obtained using this combined strategy show high sequence similarity to bovine PARG (bPARG), whereas the sequences of Drosophila and *C. elegans* only display significant homologies in the region responsible of the catalytic activity of the protein.

Figure 14:
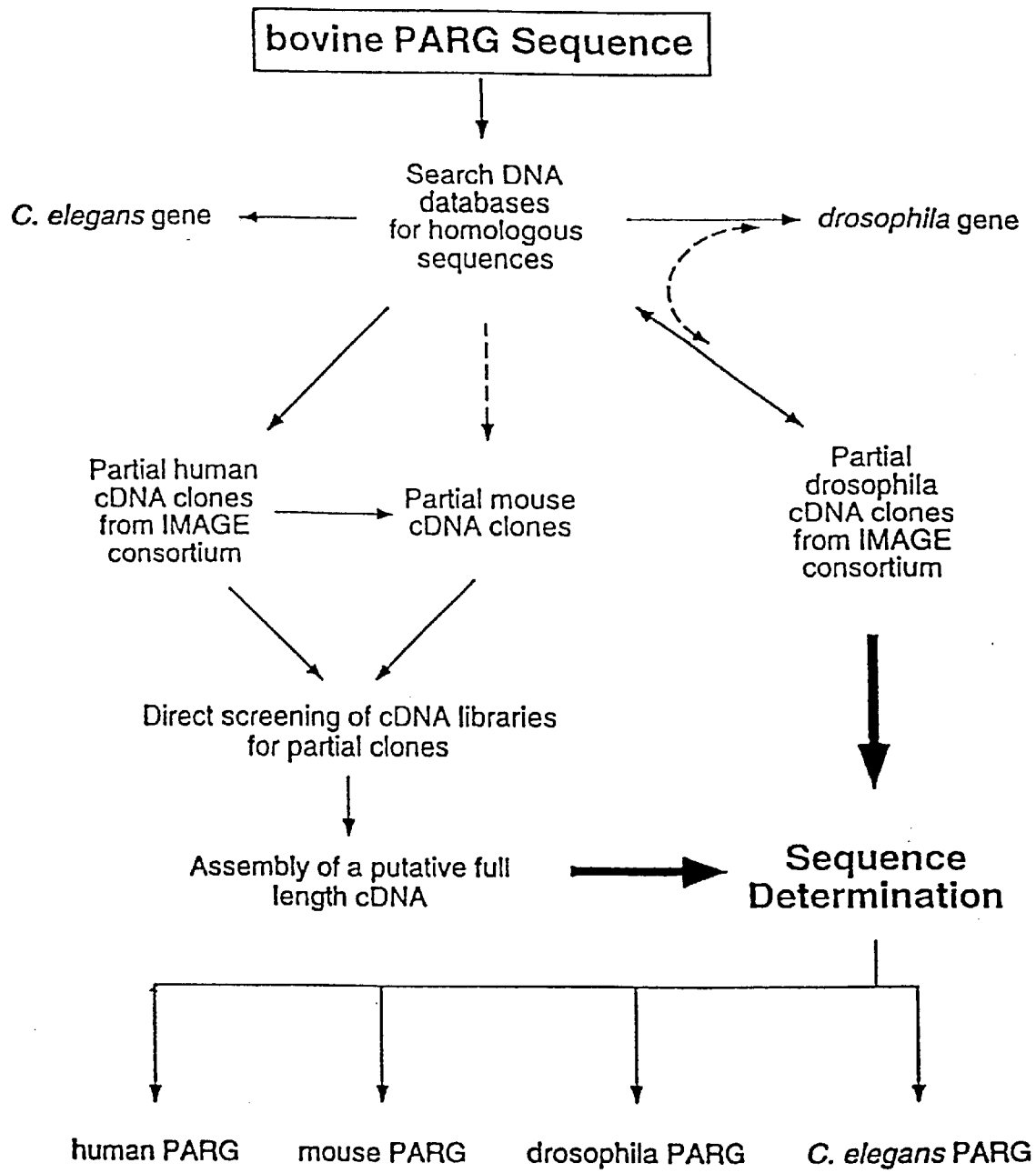
FIG. 14 depicts a schematic representation of the strategy used to isolate cDNA molecules encoding PARG from various organisms.

The strategy followed to obtain cDNAs coding for proteins with sequence similarity to bovine PARG is summarized in FIG. 14. dBEST, GenBank, SwissProt and PIR databases were searched for PARG like sequences at the nucleotide or amino acid level using the programs BLASTn, TBLASTn (Altschul et al., 1990) respectively, available at the NIH site on the Worldwide Web, and also included in the sequence analysis package from the Genetic Computer Group, Inc. (GCG) (Madison, Wis.), version 91. Both programs perform pair-wise sequence comparisons on multiple nucleotide or amino acid sequences. PARG multiple sequence comparisons obtained with these programs are very similar. Box-shading of the amino acids in the multi-sequence alignment was obtained using the program BOX-SHADE (K. Hofmann and M. D. Baron). The first step involved extensive searching for sequences with bPARG similarity in various databases. As a result of this search several partial nucleotide sequences sharing extensive homologies with bPARG cDNA were obtained from the dBEST database (65). These sequences were the result of random cloning and sequencing of partial cDNAs clones obtained from mRNAs expressed in various tissues and organisms. Among them, partial cDNAs coding for PARG from human and mouse were available. One of these human clones was particularly interesting as its sequence (2500 bp long) overlapped the coding sequence of bovine PARG from aa470 to aa977 (Carboxy terminus end) and contained all the 3' untranslated region of the human PARG cDNA. This clone (No. 50859; GenBank accession number: H 17209) was requested and freely obtained from the IMAGE Consortium (in collaboration with Washington University School of Medicine in St. Louis, Mo. and Merck & Co., info@image.llnl.gov). The sequence of the clone was then completed. This partial cDNA permitted design of a radio-labeled probe (fragment HindIII—KpnI of 677 bp) specific to human PARG (SEQ ID NO: 36).

Example 9

Cloning and sequencing.

The cloning procedures used in this work generally known and are also described in details in the book, *Molecular Cloning: A laboratory Manual* (Maniatis et al., 1982). DNA sequencing was performed using the dideoxynucleotide method of Sanger (Sanger et al., 1977). Chemical reagents were purchased from Sigma (St. Louis, Mo.). Restriction enzymes, T4 DNA ligase were from New England Biolabs, Inc. (Beverly, Mass.), T7 DNA polymerase Sequenase from US Biochemical (Cleveland, Ohio), Calf Intestine Phosphatase from Boehringer, Mannheim (Indianapolis, Ind.). The phagemid pTZ18/19R is from Pharmacia (Piscataway, N.J.). The labeled nucleotides α-[$^{35}$S]-dATP and α-[$^{32}$P]-dCTP were purchased from ICN (Costa Mesa, Calif.). Human thymus and murine liver 5'-stretch cDNA libraries cloned in the vector λgt 10 were from Clontech (Palo Alto, Calif.).

A single, isolated colony of C600Hfl *E. coli* strain was picked and grown in 5 ml of Luria-Bertani medium (LB)+10 mM MgSO$_4$+0.2% maltose overnight at 37° C. in a shaker. The bovine library lysate was diluted 1:250,000 and incubated with the C(600Hfl bacterial overnight culture and 1×lambda dilution buffer. Next, LB soft top agar+10 mM MgSO$_4$ was added, and the entire mixture was quickly poured onto 90 mm LB agar+10 mM MgSO$_4$ plates. The plates were cooled briefly at room temperature to allow the inoculum to soak into the agar before they were incubated at 37° C. for 6–7 hr. The number of clear plaques was counted to determine the titer.

Plaques containing the entire library that had been plated were transferred to nitrocellulose or nylon membranes. The filters were then washed in a 1.5 M NaCl/0.5 M NaOH solution to lyse the cells. This was followed by a 5 min wash in neutralizing solution (1.5 M NaCl/1 M Tris buffer pH 8). Finally, the filters were rinsed in 0.2×SSPE (30 mM NaCl/2 mM sodium phosphate buffer pH 7.2/0.2 mM EDTA) (Sambrook et al., 1992). The filters were then dried and baked in a 80° C. oven for 2 hr to fix the lysed plaques onto the filters.

Radioactive probes were prepared using a random hexamer priming method. Pre-hybridizations and hybridizations were carried out at 42° C. in 50% formamide, 0.25 M sodium phosphate buffer, pH 7.2, 0.25 M NaCl, 7% SDS, 1 mM EDTA.

Example 10

Specific Methods used for Library Screening.

All the cloning procedures used in obtaining the additional PARG cDNAs and determining their sequences were performed essentially as described for the bovine PARG cDNA and sequence. Human thymus and murine liver 5'-stretch cDNA libraries cloned in the vector λgt 10 were from Clontech (Palo Alto, Calif.).

Library plating and titering: A single, isolated colony of C600Hfl *E. coli* strain was picked and grown in 5 ml of Luria-Bertani medium (LB)+10 mM MgSO4+0.2% maltose overnight at 37° C. in a shaker. The library lysate was diluted 1:250000 and incubated with the C600Nfl bacterial overnight culture and 1×lambda dilution buffer. Next, LB soft top agar+10 mM MgSO4 was added, and the entire mixture was quickly poured onto 90 mm LB agar+10 mM MgSO4 plates. The plates were cooled briefly at room temperature to allow the inoculum to soak into the agar before they were incubated at 37° C. for 6–7 hr. The number of clear plaques was counted to determine the titer.

Plaque lifts: Plaques containing the entire library that have been plated are transferred to nitrocellulose or nylon membranes. The filters are then washed in a 1.5 M NaCl/0.5 M NaOH solution to lyse the cells. This is followed by a 5 mm wash in neutralizing solution (1.5 M NaCl/1 M Tris buffer pH 8). Finally, the filters are rinsed in 0.2×SSPE (30 mM NaCl/2 mM sodium phosphate buffer pH 7.2/0.2 mM EDTA) (66). The filters are then dried and baked in a 80° C. oven for 2 hr to fix the lysed plaques onto the filters.

Making a radioactive probe and Hybridizations: Radioactive probes were prepared using a random hexamer priming method. Pre-hybridizations and hybridizations were carried out at 42° C. in 50% formamide, 0.25 M sodium phosphate buffer, pH 7.2, 0.25 M NaCl, 7% SDS, 1 mM EDTA. This partial cDNA allowed to design a radiolabeled probe (fragment HindIII—KpnI of 750 bp long) specific to human PARG.

Example 11

Screening of a human thymus 5'-stretch cDNA libraries.

Multiple screenings of a human thymus 5'-stretch cDNA library were performed to complete the cloning of human PARG cDNA. For each screening a new probe was designed and used to screen approximately one million recombinants of the library. During each round of screening, overlapping clones were isolated at high stringency conditions and subcloned into the EcoRI site of pTZ18/19R phagemid using standard techniques. The different positive clones (J5, C, E1, E2, M, M', M", P', P", Of, 02) were characterized by restriction analysis, subcloned into the appropriate restriction sites of pTZ18/19R as necessary and sequenced in both strand using the dideoxynucleotide method. The probe used to complete the cloning of the human cDNA library is shown is SEQ ID NO: 37. Finally, a full-length cDNA sequence was assembled which encodes the human PARG. The sequence of the cDNA encoding human PARG is presented in the sequence listing as SEQ ID NO: 3 and the amino acid sequence of human PARG is presented in the sequence listing as SEQ ID NO: 4.

The human PARG sequence shares extensive amino acid sequence homologies with bovine PARG with more than 89% identity. The sequence similarity is also high at the nucleotide level particularly in the region coding for the protein (174ATG-TGA3104). Surprisingly the 5'-untranslated region of the human sequence displays a completely different sequence with an extensive sequence similarity with highly repeated polymorphic DNA sequences found in the human genome such as Alu repetitive elements or variable number of tandem repeats (VNTR).

Example 12
Screening of Mouse Liver 5'-stretch cDNA Libraries.

To isolate a PARG cDNA from the mouse liver cDNA library, a probe was designed from the human cDNA clone coding for PARG. Analysis of the bovine and human sequences revealed that PARG was highly conserved between these two species, suggesting that it might also be conserved in the mouse. Based on the restriction map of the human cDNA clone, a region in the human clone was selected, located where the active site of the protein is encoded, that exhibited near identity to its counterpart in the bovine clone. This region, consisting of approximately 800 bases, was excised from the entire human clone by digestion with the restriction endonuclease, HindIII, then purified by agarose gel separation and radiolabeled by random priming.

This probe was used to screen a mouse liver 5'-stretch cDNA library. One clone consistently hybridized with the probe. After two rounds of screening to ensure the purity of the clone the 2.5 kb insert was subcloned into the plasmid pTZ19R and sequenced. Comparison with the sequence of bovine and human PARG showed that this clone had the partial sequence that has extensive similarities to the two other mammalian sequences covering almost entirely the coding region from nucleotide—10 to a few nucleotides from the end of the coding region. A second screen was performed to obtain the missing part of the cDNA using a radioactive probe specifically designed to hybridize with the region the most 3' of the previous clone to increase the chance to get the missing part of the cDNA.

With this new probe, the same mouse liver cDNA library was screened to obtain a second clone, containing an insert that was about 3 kb. This clone was purified, subcloned and sequenced. The sequence showed that this second clone starts at amino acids 634, extends toward the stop codon to approximately 900 nucleotides into the 3' non-coding region.

A search of the dBEST database turned up one significant match to a 400 bp fragment cloned from mouse muscularis. This fragment had an exact match to the very tail end of the second clone and exceeded it by 34 bases. This extra extension contained the oligo A sequence as well as the polyadenylation signal. Because there was an exact match, the cDNA sequence was completed using this information coming from the database. The complete cDNA sequence of murine PARG is presented in the Sequence Listing as SEQ ID NO: 5 and SEQ ID NO: 6.

Example 13
Obtaining the Drosophila PARG cDNA.

Figure 15:
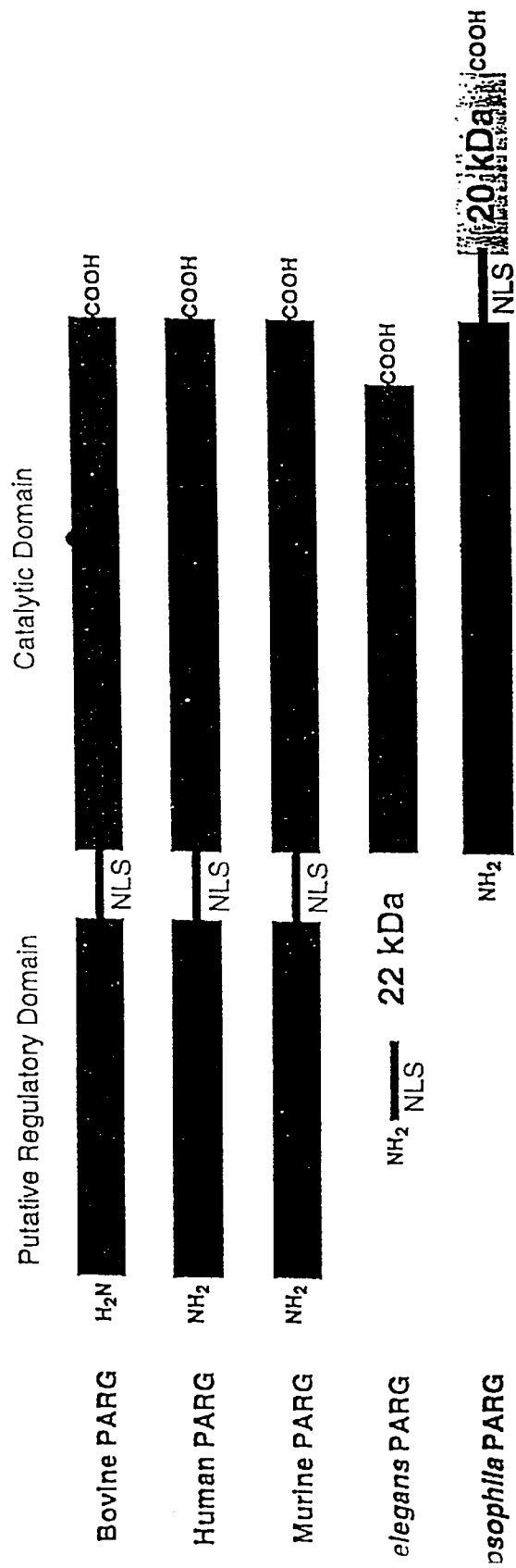
FIG. 15 depicts the domain organization of PARGs from different organisms.

Among the clones obtained from DNA databases searches were several clones from the Drosophila genome sequencing project (European Drosophila Genome Sequencing Consortium) as well as the Drosophila expression sequence TAG sequencing project (67). The EST clone was requested from the University of California Berkeley and obtained. Because the sequence published in the dBEST database was only partial, its sequence was completed in our laboratory and compared to a genomic sequence, part of the distal X chromosome of Drosophila melanogaster submitted by Murphy et al., August 1997 which presumably contains the gene of Drosophila PARG. The 768 aa shares less homologies with only 40% identity (48% similarity) mainly located in the catalytic domain of the protein. The domain organization of the protein is also very different with an unknown domain of 20 kDa located Carboxy terminus of the highly conserved active domain. (See FIG. 15). The sequence of the cDNA encoding the Drosophila PARG is presented in the Sequence Listing as SEQ ID NO: 7 and the amino acid sequence of the Drosophila PARG is presented in the Sequence Listing as SEQ ID NO: 8.

Example 14
Obtaining the C. elegans PARG Sequence.

This sequence has been obtained by searching the GenBank database with the mammalian PARG protein sequence. A sequence with PARG similarity was found in the cosmid F20C5 (Accession number: Z68161, SEQ ID NO: 38) derived from the C. elegans genomic DNA (68). The overall sequence conservation (726aa, MW 83129 Da) with the other PARG sequences is as follows: 32% similarity and 22% identity with the mammalian PARG and 39% similarity and 30% identity with the Drosophila PARG. The sequence is presented in the Sequence Listing as SEQ ID NO: 38 (Genbank accession number CEF20C5). SEQ ID NO: 38 contains 12 exons as follows: exon 1 from 3591 to 3635; exon 2 from 3681 to 4121; exon 3 from 5065 to 5235; exon 4 from 5930 to 6152; exon 5 from 6200 to 6267; exon 6 from 7246 to 7338; exon 7 from 7686 to 7553; exon 8 from 7738 to 7853; exon 9 from 8153 to 8435; exon 10 from 8487 to: 8610; exon 11 from 8662 to 8952; and exon 12 from 9383 to: 9540. The coding sequence of the CePARG protein, which is publicly available from Accession number: Z68161, is referred to in the Sequence Listing as SEQ ID NO: 9. Its corresponding amino acid sequence is referred to in the Sequence Listing as SEQ ID NO: 10. The amino acid sequence of the C. Elegans PARG is presented on the alignment (FIG. 16)

Example 15
Cloning and Overproduction of the Carboxyl-terminus 69 kDa Domain of Bovine PARG (bPARG) in E. coli.

As described, above, bovine PARG is encoded by a messenger of 4 kb predicting a protein of 110 kDa, almost twice the size of the purified enzyme (65 kDa). It is also demonstrated that bPARG can be expressed in E. coli as an active enzyme either as a 110 kDa or a 65 kDa protein. This result combined with other evidence implies that the active site of PARG is located in the carboxyl-terminal part of the protein. FIG. 11 is a schematic representation of the different clones we have expressed in bacteria. Among them, only the clone designed to express a protein of 69 kDa starting at the amino acid +380 from the sequence of bovine PARG ($bPARG_{MNDV}$) allowed high level expression as a fusion protein with glutathione-S transferase (GST).

The heterologous expression of $bPARG_{MNDV}$ was conducted as represented in FIG. 12. The 1.8 kb cDNA encoding the 69 kDa carboxyl-terminal part of bovine PARG was amplified by PCR and cloned in the EcoRI site of pGEX-2T vector (Pharmacia) in fusion with GST giving the pGEX-2T-$bPARG_{MNDV}$ plasmid. E. coli NM522 cells transformed with the pGEX-2T-$bPARG_{MNDV}$ were induced by addition of IPTG, resulting in expression of a 90 kDa fusion protein. The fusion protein can be conveniently purified using Glutathione-Sepharose and the bPARG$_{MNDV}$ can be released by treatment with thrombin while the GST protein remains bound to the beads of GSH-Sepharose. In this manner milligram amounts of protein can be routinely obtained.

Example 16

Characterization of the purified 65 kDa Domain and the Generation of Antibodies.

The purified bPARG$_{MNDV}$ was characterized by activity gel assays (69) by casting polyacrylamide gels with auto modified PARP containing [$^{32}$P]ADP-ribose polymers. The results demonstrate that the 65 kDa domain expressed in E. Coli contained enzymatic activity migrating with the same apparent molecular weight as the enzyme purified from bovine thymus. Likewise, a construction expressing bPARG$_{MNDV}$ domain in SF9 insect cells infected with recombinant baculovirus showed activity migrating with the same apparent molecular weight.

The availability of PARG cDNA allows the development of new molecular tools to study this enzyme in its cellular context. Until this work, it was not possible to obtain PARG in sufficient quantities to produce antibodies against the protein. The antibody raised against bovine PARG is able to recognize PARG from other organisms and, thus, will be valuable in characterizing PARG in vivo under defined physiological conditions in many different organisms.

Antibodies against bPARG$_{MNDV}$ overexpressed in E. coli were raised in rabbits using the procedure described by Vaitukaitis (70). Specific high affinity antibodies are generated by administration of small doses of immunogens intradermally over a wide anatomic area of the animal. Rabbits were immunized by three injections of 10–50 μg of the Mr 65,000 protein band excised from a preparative SDS polyacrylamide gel. Titer and affinity of sera harvested weekly were followed by conventional methods. Peak affinity was attained in 8 to 10 weeks after primary immunization. For each animal, a preimmune serum was retained as a control.

Figure 17:
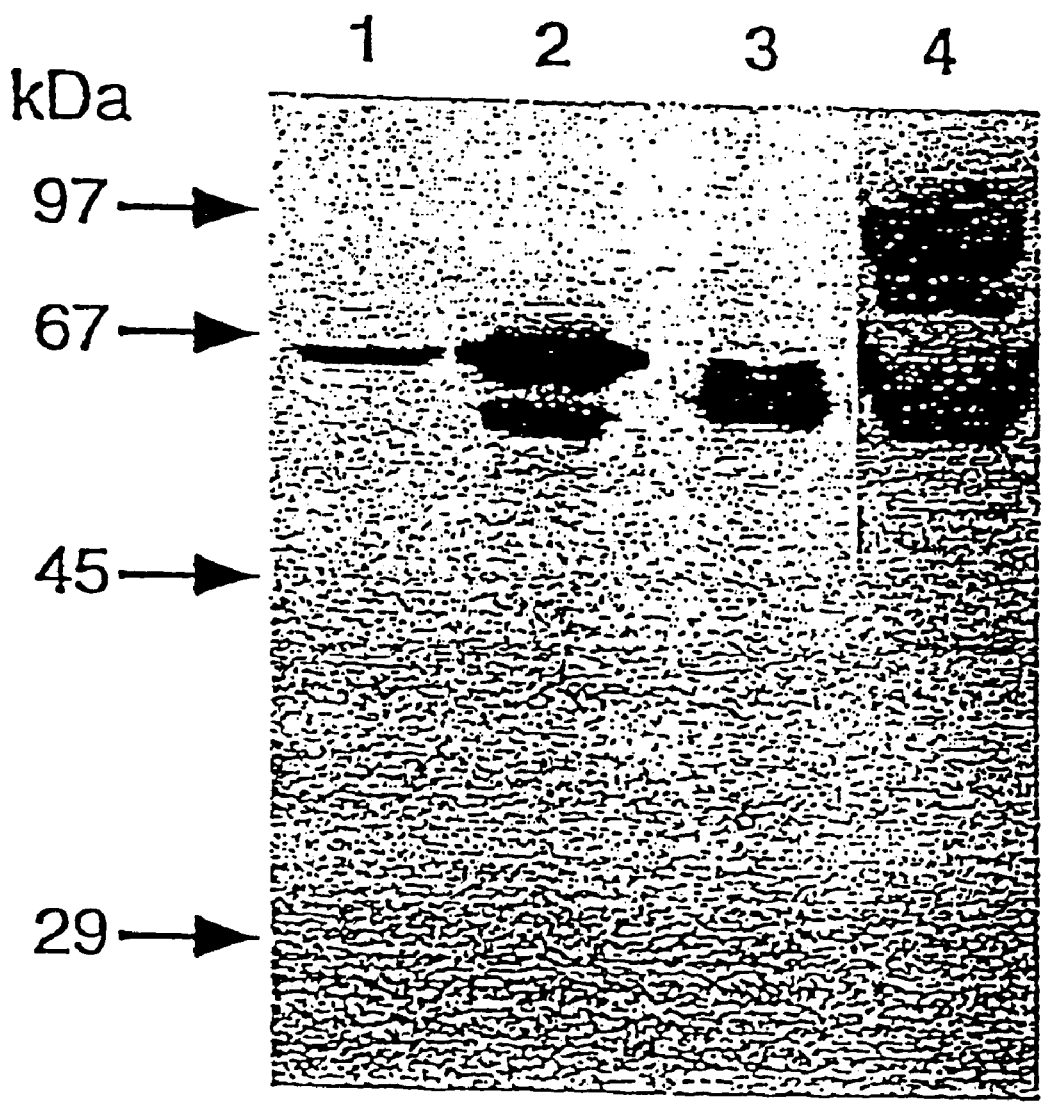
FIG. 17 depicts a western blot of recombinant PARGs.

FIG. 17 shows a Western blot experiment demonstrating the specificity of the resulting PARG anti-serum against the purified bPARG from thymus (lane 1), SF9 protein extract expressing 65 kDa-bPARG$_{MNDV}$ in recombinant baculovirus (lane 2), recombinant 65 kDa-PARG$_{MNDV}$ purified by treatment with thrombin from GSH-Sepharose (lane 3), and an E. coli crude extract expressing the fusion protein GST-65 kDa-PARG$_{MNDV}$ (lane 4). The pre-immune serum did not show reactivity against any of these fractions even at a low dilution (1/250).

Antibodies directed against the 45 kDa -terminal have also been generated using the same strategy used to generate antibodies against the catalytic domain. This involved the overexpression of the 45 kDa protein domain in E. coli in a construct designed for easy purification, followed by injection of the purified protein into rabbits. The heterologous expression of PARG45 was conducted by cloning a part (1.1 kb) of the coding region of the cDNA, generated by PCR amplification of the region located between the ATG(267) codon and nucleotide 1400 in the bovine sequence, into the Eco RI site of the bacterial expression vector pGEX-2T (Pharmacia) in fusion with glutathione-S-transferase. E. Coli NM522 cells transformed with this construct were induced by addition of IPTG, resulting in expression of a 72 kDa fusion protein. The fusion protein was purified using glutathione Sepharose and the PARG45 was released by treatment with thrombin, while the GST protein remained bound to the GSH Sepharose beads. In this manner milligram amounts of protein were obtained. Antibodies against PARG45 overexpressed in E. coli were raised in rabbits using the procedure described (71). Specific high affinity antibodies were generated by administration of small doses of immunogens subcutaneously over a wide area of the animal. Rabbits were immunized by three injections of 10–50 μg of the 45 kDa protein band excised from a preparative SDS-polyacrylamide gel. Titer and affinity of sera harvested weekly were followed by conventional methods. Peak affinity was attained in 8 to 10 weeks after primary immunization. For each animal, a preimmune serum was retained as a control.

Example 17

Conservation of PARG in Tissues and Organisms.

Tissue and cell extracts from different origins were homogenized in a cold hypotonic lysis buffer containing a cocktail of protease inhibitors and sonicated. SDS and β-mercaptoethanol were added to insure inactivation of any remaining active proteases. Thirty μg of protein from each extract was analyzed by Western-blot using the anti-PARG antibody (FIG. 18). In all of the fractions from bovine tissues, PARG was observed as a major band at 65 kDa. However, less intense, discrete proteins of higher molecular weight were also detected. These proteins may correspond to different forms of PARG; the band of highest molecular weight (about 115 kDa) found in thymus extract likely corresponds to the full-length of PARG (111 kDa) as deduced from the cDNA. Multiple species were detected in cell extracts from mouse fibroblasts, rat PC 12 cells, and SF9 insect cells. This result shows that the sequence of PARG is well conserved phylogenetically. Moreover, the conservation includes multiple molecular forms of the protein.

Example 18

Regulation of the expression of PARG.

In the metabolism of ADP-ribose polymers, the activities of PARP and PARG are closely related. Soon after polymer has been synthesized by PARP following DNA damage, it is extensively degraded by PARG. The net result is that the polymer has a very short half life. The close relationship between the two proteins suggests a possible mode of regulation in which PARG expression depends on the presence of PARP. In order to test if the presence or the absence of PARP influences the expression of PARG, a Western Blot experiment was performed with cell extracts from mouse fibroblasts of different PARP genotypes (72).

Figure 19:
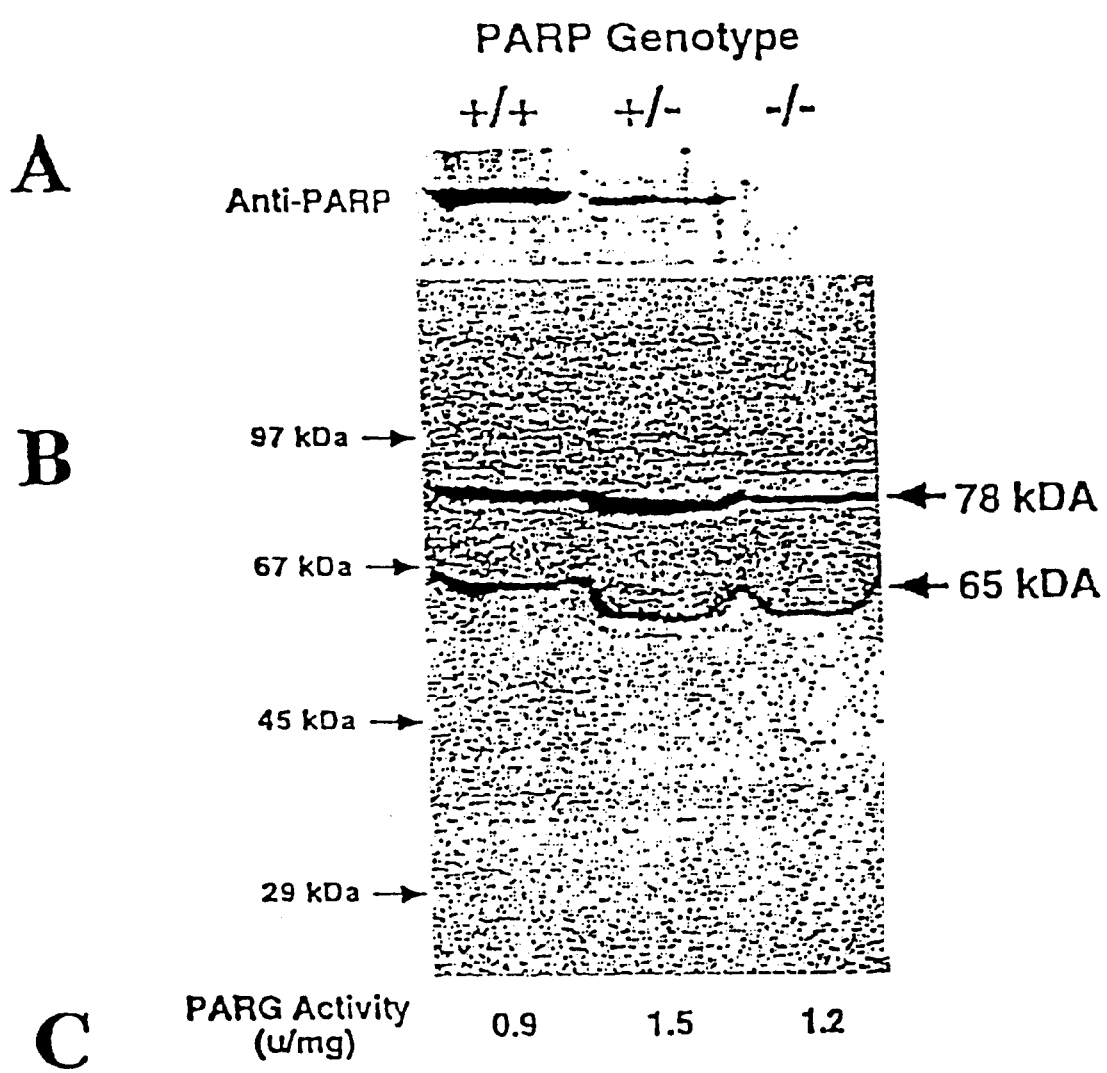
FIG. 19(A–C) depicts the characterization of PARG by Western Blot in mouse cells of different PARP genotypes.

Cell extract (30 μg) from mouse cells with PARP +/+, PARP+/− and PARP−/−genotypes were separated by SDS-PAGE, transferred to a membrane and probed with the antibodies indicated. The results are shown in FIG. 19. In FIG. 19, purified PARG (50 ng) from bovine thymus (lane 1), 30 μg of protein of a total extract from PARG recombinant baculovirus infected SF9 cells (lane 2), 150 ng of purified recombinant PARG produced in the bacteria (lane 3) and 30 μg of protein of acrude extract from E. coli NM522 transformed with pGEX-2T-bPARG$_{MNDV}$ 2 h after induction by IPTG (lane 4) were separated on a 0.1% SDS–12% polyacrylamide gel, then transferred on nitrocellulose, and incubated with a 1/5000 dilution of the rabbit polyclonal antiserum raised against the 65 kDa domain of bPARG. Proteins were revealed by immunofluorescence with the ECL detection kit (Amersham) and autoradiography. Panel A is a western blot of PARP in cells of varying PARP genotype showing the results of the analysis using anti-PARP antibodies. The amount of PARP expressed varies as expected dependant upon the genotype of the cell line with the PARP−/−cell line producing no detectable amount of PARP. Panel B is western blot of PARG from various tissues using an anti-PARG antibody. It shows that the level of PARP is variable. The amount of PARG present in the cell extracts was not dependent upon the PARG genotype of the cell. Further support for this view is provided by the results of the PARG activity assay presented in panel C. The specific activity of PARG detected in the extracts showed no significant difference among the three genotypes.

Example 19
Preparation PARG Gene Ablation (Knockout) Animals.

One embodiment of the present invention is experimental animals with targeted mutations in the PARG gene. These animals may be constructed using standard techniques and the cDNA sequence of the PARG. In the following example, a mouse containing a targeted mutation in the PARG gene is constructed. Those skilled in the art will readily appreciate that other experimental animals, including but not limited to rats, guinea pigs, hamsters and the like, may be constructed using similar techniques. The construction of animals with disrupted genes may be accomplished using standard techniques such as those described by Moreadith (73). Further, cells lines, construction kits, and protocols for knockout mice are available from commercial suppliers such as Stratagene (Stratagene 1999 catalog, La Jolla, Calif.). Commercial services such as Lexicon Genetics (The Woodlands, Tex.) and Chrysalis DNX Transgenic Sciences (Princeton, N.J.) also offer complete ES cell knockout mice production services.

Figure 20:
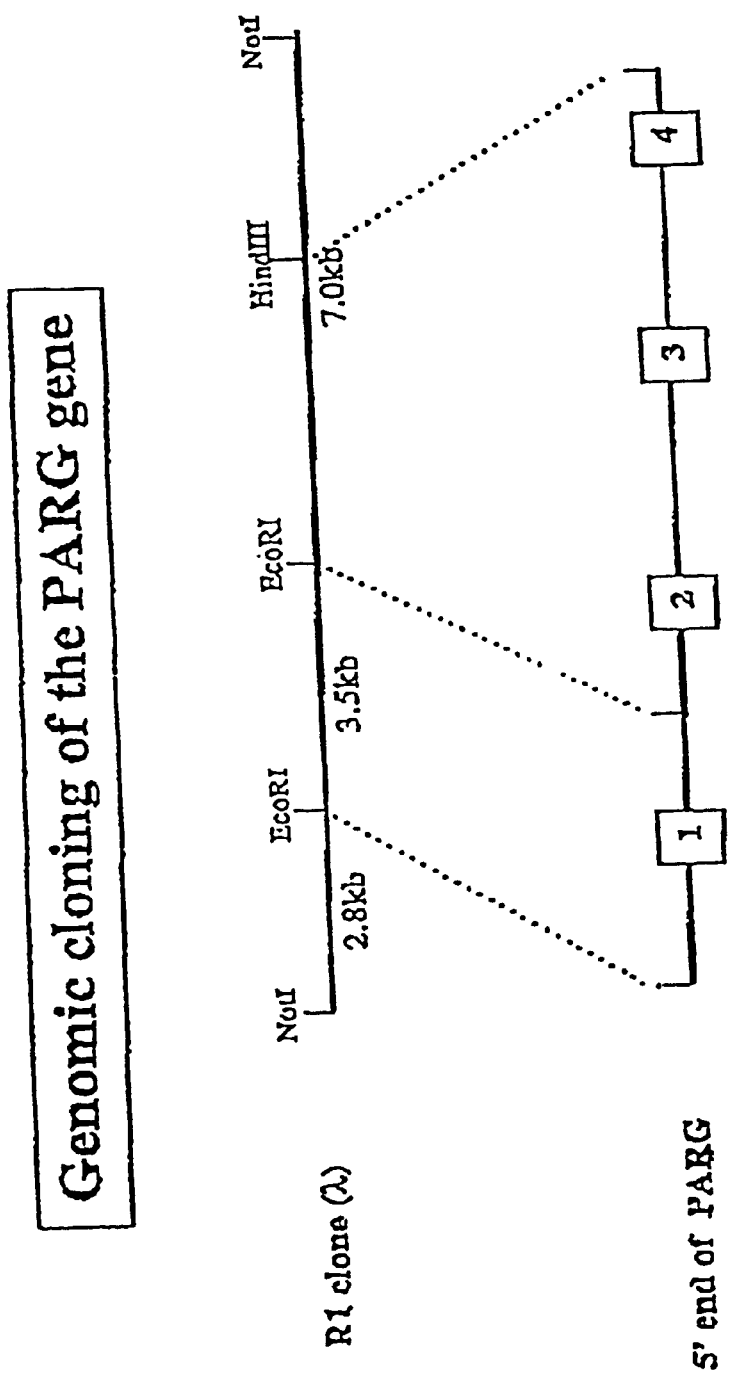
FIG. 20 depicts a partial restriction map of the mouse PARG locus.

A genomic clone of the murine PARG enzyme may be isolated from a genomic library by screening with a probe derived from the cDNA sequence of PARG. A mouse 129/SV genomic library (Stratagene) containing mouse genomic sequences in λ phage was screened using a 2.49 kb fragment of the mouse PARG cDNA as a probe. A partial restriction map of one positive clone thus isolated, R1, is provided in FIG. 20. The R1 clone contains the genomic sequence corresponding to the 5'-most end of the murine cDNA. The clone was subcloned into pBluescript as three fragments. The plasmid containing the 5'-end contained a 2.8 kb NotI-EcoRI fragment and was designated p2.8R. The fragment containing the central portion contained a 3.5 kb EcoRI fragment and was designated p3.5R. The plasmid containing the 3'-end of the gene contained a 7,0 kb EcoRI-NotI fragment and was designated 7.0R. Sequencing the resulting plasmids revealed that p2.8R contained no sequences corresponding to the cDNA, p3.5R contains a 1.5 kb promoter region and/or untranslated region and exon 1 coding for 72 amino acids including the initiation ATG codon and p7.0R contains at least 4 additional exons. Gene targeting vectors may be constructed using both p3.5R and p7.0R.

Figure 21:
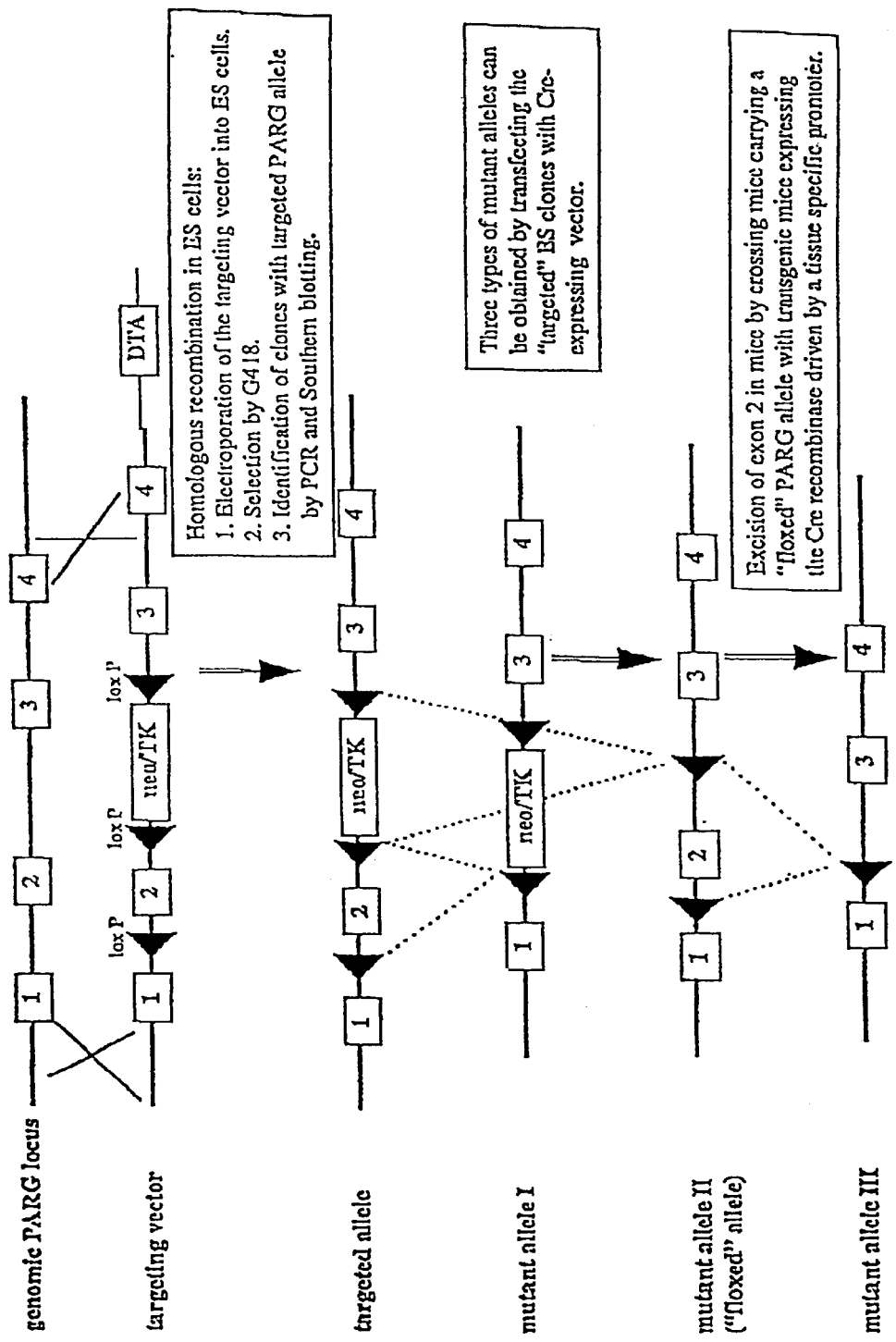
FIG. 21 depicts a schematic representation of the strategy used to create PARG knockout mice.

A gene targeting vector may contain one or more selection genes flanked by genomic sequences. The targeting vector is introduced into the genome by homologous recombination resulting in the incorporation of the selection gene into the geneome of the cell. The mouse PARG gene was targeted using a "conditional" inactivation procedure outlined in FIG. 21. This approach allows the production of viable animals even if the disrupted gene results in a lethal phenotype since the gene is not disrupted until a second "conditional" recombination event is induced.

A lox-P sequence may be inserted into the first intron. A cassette expressing the neomycin resistance gene (neo) and the thymidine kinase gene (TK) flanked by two additional lox-P sites may be placed in intron 2. In the presence of Cre recombinase, recombination will occur between two lox-P sites thereby deleting the genomic sequences present between the sites. A MC1-DTA cassette is ligated at the 3'-end of the vector to reduce random integration of the vector into the genome.

The targeting vector may be introduced into embryonic stem cells by any method known to those skilled in the art such as transfection, lipofection or electroporation. In a preferred embodiment, the targeting vector will be introduced into embryonic stem cells by electroporation. After homologous recombination, cells containing the neo gene will be selected for using G418. Selected cells will then be analyzed by PCR and Southern blot.

To generate mutant alleles of PARG, the positive embryonic stem cell clones identified will be transfected with a plasmid expressing Cre recombinase. The action of Cre recombinase will result in three different mutant alleles. Mutant allele I contains a deletion in exon 2 but still maintains the selection genes neo and TK. Mutant allele II contains the genomic sequence for exon 2 flanked by two lox-P sites (exon 2 is said to be "floxed") and does not contain the selection genes. Mutant allele III has a deletion of the genomic sequences and does not contain the selection genes.

Mice containing each of the three mutant alleles may be constructed by microinjecting embryonic stem cells containing the mutant allele into blastocytes resulting in the production of chimeric and mutant mice. Mice homozygous in mutant allele I or III will be null mutants in that they will be unable to express a functional PARG enzyme due to the loss of required genomic sequences. In the absence of Cre recombinase, mice containing mutant allele II will express a wild type protein. In the presence of the Cre recombinase, the PARG will lose exon 2, thus producing an inactive protein. To inactivate the gene, these mice will be bred to mice expressing Cre recombinase under the control of a tissue specific promoter. This will result in mice expressing PARG in some tissues and not expressing PARG in others. Mice homozygous in mutant allele II, will be valuable for evaluating the role of PARG in specific tissues.

Although the present invention has been described with reference to certain examples for purposes of clarification and illustration. It should be appreciated that certain obvious improvements and modifications can be practiced within the scope of the appended claims and their equivalents. Other embodiments and uses of the invention will be apparent to those skilled in the art from consideration of the specification and practice of the invention disclosed herein. All U.S. Patents GenBank sequence listings, and other references noted herein for whatever reason are specifically incorporated by reference. The specification and examples should be considered exemplary only with the true scope and spirit of the invention indicated by the following claims.

1. Miwa, M. et al. (1971) J. Biol. Chem. 246, 6362–6364; Ueda, K. et al. (1972) Biochem. Biophys. Res. Commun. 46, 516–523
2. Oka, J. et al. (1984) J Biol. Chem. 259, 986–995.
3. Gaal, J. et al. (1987) Trends in Biol. Sci., 12, 129.
4. Nudka, N. et al. (1980) Eur. J. Biochem. 105, 525–530; Jacobson, E. et al. (1985) carcinogenesis 6, 715–718; K upper, J. et al. (1990) J. Biol. Chem. 265, 18721–18724; Ding, R. et al. (1992) J Biol. Chem. 267, 12804–12812.
5. Jacobson, E. et al. (1985) in ADP-ribosylation of Proteins (Althaus, F. R., Hilz, H., and Shall, S., eds) pp. 277–283, Springer-Verlag, Berlin; Lubet, R. et al. (1986) Carcinogenesis 7, 71–75; Kasid, U. et al. (1986) Carcinogenesis 7, 327–330.
6. Berger, N. (1985) Radiat. Res. 101, 4–15.
7. Kaufmann, S. et al. (1993) Cancer res. 53, 3976–3985; Lazebnik, Y. et al. (1994)Nature 371, 346–347.
8. de Murcia, G. et al. (1994) Trends Biochem. Sci. 19, 172–176.
9. BioWorld Today, Apr. 29, 1994, p. 3.
10. Thomassin, H. et al. (1990) Nucleic Acids Res. 18, 4691–4694.
11. Karlin, Samuel and Stephen F. Altschul (1993). Proc. Natl. Acad. Sci. USA 90:5873–7
12. Henikoff and Henikoff Proc. Natl. Acad. Sci. USA 89:10915–19, 1992
13. Altschul, Stephen F. (1991). J. Mol. Biol. 219:555–65.
14. Cohen, J. S., 1989; Weintraub, H. M., 1990
15. N. Sarver et al., 1990
16. Orlandi, R. et al., (1989) Proc. Natl. Acad. Sci. 86, 3833–3837; Winter, G et al., (1991) Nature 349, 293–299
17. R. Sobol and K. Scanlon eds., available at www.appleton-lange.com.

18. e.g., at least, but not limited to U.S. Pat. No. 5,797,870, U.S. Pat. No. 5,804,383, U.S. Pat. No. 5,670,161, U.S. Pat. No. 5,645,829, U.S. Pat. No. 5,741,486, U.S. Pat. No. 5,836,905, U.S. Pat. No. 5,843,069, U.S. Pat. No. 5,827,216, U.S. Pat. No. 5,871,464, U.S. Pat. No. 5,702,384, U.S. Pat. No. 5,810,888, U.S. Pat. No. 5,787,900, U.S. Pat. No. 5,752,515, U.S. Pat. No. 5,674,192, U.S. Pat. No. 5,658,955, U.S. Pat. No. 5,656,465, U.S. Pat. No. 5,547,932, U.S. Pat. No. 5,873,904, U.S. Pat. No. 5,792,651, U.S. Pat. No. 5,772,888, U.S. Pat. No. 5,641,750, U.S. Pat. No. 5,641,749, and U.S. Pat. No. 5,626,561
19. Kaltenbock, B. et al. (1998) *Biotechniques*, 24, 202–206.
20. Moran, P. et al. (1998) *Biotechniques*, 24, 206–212.
21. Orita, M. et al. (1989) *PNAS USA*, 86, 2766–2770.
22. Liu, Q. et al. (1998) *Biotechniques*, 24, 140–147.
23. *Proceeding from the Sixth International Symposium on Human Identificiation* 1995 (ISBN 1-882274-55-5).
24. Kohler and Milstein, *Nature*, 256:495–497 (1975).
25. Geysen, et al. (1984) *Proc. Natl. Acad. Sci. U S A* 81:3998–4002.
26. Ménard, et al. (1987) *Biochem. Cell Biol.* 65, 668–673.
27. Hatakeyama, K. et al. (1986) *J. Biol. Chem.* 261, 14902–14911.
28. Thomassin, H. et al. (1990) *Nucleic Acids Res.* 18, 4691–4694.
29. Ménard, L. et al. (1987) *Biochem. Cell Biol.* 65, 668–673.
30. Bradford, M. (1976) *Anal. Biochem.* 72, 248–254.
31. Laemmli, U. (1970) *Nature* 227, 680–685.
32. Althaus, F. et al. (1987) *MolecularBiology, Biochemistry and Biophysics*, Vol. 37, Springer-Verlag, Berlin.
33. Mead, D. et al. (1986) *Protein Eng.* 1, 67–74.
34. Shaw, et al. (1986) *Cell* 46, 659–667.
35. Kozak (1987) *Nucleic Acids Res.* 15, 8125–8148.
36. Wilson, et al. (1994) *Nature (London)* 368, 32–38.
37. Brendel, et al . (1992) *Proc. Natl. Acad. Sci. USA* 89, 2002–2006.
38. Robbins, et al. (1991) *Cell* 64, 615–623.
39. Schreiber, et al. (1992) *EMBO J.* 11, 3263–3269.
40. Uchida, K. et al. (1987) *Biochem. Biophys. Res. Commun.* 148, 617–622; Cherney, B. et al. (1987) *Proc. Natl. Acad. Sci. U.S.A.* 84, 8370–8374; Kurosaki, T. et al. (1987) *J. Biol. Chem.* 262, 15990–15997.
41. Huppi, K. et al. (1989) *Nucleic Acids Res.* 17, 3387–3401.
42. Saito, I. et al. (1990) *Gene (Amst.)* 90, 249–254.
43. Ittel, M.-E. et al. (1991) *Gene (Amst.)* 102, 157–164.
44. Saulier-Le Dream, B. (1992) Poly(ADP-ribose) Polymerase in Xenopus lae-vis, Ph.D. thesis, Université De Rennes, France.
45. Uchida, K. et al. (1993) *Proc. Natl. Acad. Sci. U.S.A.* 90, 3481–3485.
46. Masutani, M. et al. (1994) *Eur. J Biochem.* 220, 607–614.
47. Schreiber, et al. (1992) *EMBO J.* 11, 3263–3269.
48. Lazebnik, et al. (1994) *Nature (london)* 371, 346–347.
49. Brochu, et al. (1 994) *Biochem. Biophys. Acta* 1219, 342–350.
50. Tanuma, et al. (1986) *J. Biol. Chem.* 261, 965–969; Uchida, et al . (1993) *J. Biol. Chem.* 268, 3194–3200.
51. Maruta, et al. (1991) *Biochemistry* 30, 5907–5912.
52. Ménard, L. et al. (1987) *Biochem. Cell Biol.* 65, 668–673.
53. Ménard, L. et al. (1987) *Biochem. Cell Biol.* 65, 668–673.
54. Slama, J. et al. (1995) *J. Med. Chem.* 38, 389–393; Slama, J. et al. (1995) *J. Med. Chem.* 38, 4332–4336.
55. Slama, J. et al. (1995) *J. Med. Chem.* 38, 389–393; Slamna, J. et al. (1995) *J. Med. Chem.* 38, 4332–4336.
56. Ménard, L. et al. (1987) *Biochem. Cell Biol.* 65, 668–673.
57. Althaus, F. et al. (1987) *Molecular Biology, Biochemistry and Biophysics*, Vol. 37, Springer-Verlag, Berlin.
58. Brochu, G. et al. (1994) *Anal. Biochem.* 218, 265–272.
59. Brochu, G. et al. (1994) *Anal. Biochem.* 218, 265–272.
60. Moreadith, et al. (1997) *J Mol. Med.* 75, 208–216.
61. Tanuma, et al. (1986) *J. Biol. Chem.* 261, 965–969 and Uchida, et al. (1993) *J Biol. Chem.* 268, 3194–3200.
62. Hatakeyama, et al. (1986) *J. Biol. Chem.* 261, 14902–14911; Thomassin, et al. (1990) *Nucleic Acids Res.* 18, 4691–4694; and Maruta, et al. (1991) *Biochemistry* 30, 5907–5912.
63. Sambrook, et al. (1992) *MOLECULAR CLONING*: A LABORATORY MANUAL, Cold Spring Harbor Laboratory Cold Spring harbor, N.Y.
64. Feinberg, et al. (1983) *Anal. Biochem.* 132, 6–13.
65. Boguski, 1995
66. Sambrook, et al. (1992) *MOLECULAR CLONING*: A LABORATORY MANUAL, Cold Spring Harbor Laboratory Cold Spring Harbor, N.Y.
67. BDGP/HHMI Drosophila EST Project, University of California Berkeley, EST@fruitfly.berkeley.edu
68. Nematode Sequencing Project, Sanger Centre, Hinzton, Cambridge CB101RQ, England and Department of Genetics, Washington University, St. Louis, Mo. 63110, USA. E-mail: jes169 sanger.ac.uk
69. Brochu G. et al. (1994) *Anal. Biochem.* 218, 265–272.
70. Vaitukaitis (1981) *Methods in Enzymology* 73, 46–52.
71. Vaitukaitis (1981) *Methods in Enzymology* 73, 46–52.
72. Wang, et al. (1995) *Genes & Dev.* 9, 509–520.
73. Moreadith, et al. (1997) *J. Mol. Med.* 75, 208–216.

We claim:

1. A method for screening a molecule to determine if it modulates enzymatic activity of an enzyme which hydrolyzes an ADP ribose molecule from an ADP ribose, comprising:
   (i) transforming or transfecting a cell with an isolated nucleic acid molecule which is at least 80% homologous to the nucleotide sequence set forth at SEQ ID NO: 1;
   (ii) culturing the transformed or transfected cell of (i) to produce said enzyme;
   (iii) isolating and purifying said enzyme;
   (iv) combining said enzyme, said molecule and an ADP ribose polymer;
   (v) determining degree of hydrolysis in (iv), and
   (vi) comparing degree of hydrolysis of (v) to degree of hydrolysis obtained by combining said enzyme and said ADP ribose polymer in the absence of said molecule, difference there between indicating said molecule modulates activity of said enzyme.

2. The method of claim 1, wherein said enzyme has a molecular weight greater than about 100 kilodaltons as determined by SDS-PAGE.

3. The method of claim 1, wherein said enzyme has the amino acid sequence set forth in SEQ ID NO: 2, SEQ ID NO: 4, or SEQ ID NO: 6.

4. The method of claim 1, wherein the amino acid sequence of said enzyme comprises SEQ ID NO: 11, SEQ ID NO: 12, SEQ ID NO: 13, and SEQ ID NO: 14.

5. The method of claim 1, wherein said enzyme comprises amino acids 697 to 977 of SEQ ID NO: 4.

6. The method of claim 1, wherein the complementary sequence of said nucleic acid molecule hybridizes, under stringent conditions to the nucleotide sequence set forth in SEQ ID NO: 1.

7. The method of claim 1, wherein said nucleic acid molecule comprises the nucleotide sequence set forth in SEQ ID NO: 1, 3 or 5.

8. A method for screening a molecule to determine if it modulates enzymatic activity of an enzyme which hydrolyzes an ADP-ribose molecule from an ADP ribose polymer, wherein said enzyme comprises the amino acid sequences set forth in SEQ ID NOS: 11, 12, 13 and 14 and has a molecular weight greater than about 100 kilodaltors as determined by SDS-PAGE comprising contacting said molecule, said enzyme and an ADP ribose polymer, determining degree of hydrolysis of said ADP-ribose polymer, and comparing said degree of hydrolysis to the degree of hydrolysis obtained by combining said enzyme and said ADP-ribose polymer in the absence of said molecule, difference there between indicating said molecule modulates activity of said enzyme.

* * * * *